(12) United States Patent
Bozik et al.

(10) Patent No.: US 10,285,981 B2
(45) Date of Patent: *May 14, 2019

(54) COMPOSITIONS AND METHODS FOR TREATING AMYOTROPHIC LATERAL SCLEROSIS IN RESPONDERS

(71) Applicant: KNOPP BIOSCIENCES LLC, Pittsburgh, PA (US)

(72) Inventors: Michael E. Bozik, Pittsburgh, PA (US); Thomas Petzinger, Jr., Pittsburgh, PA (US); James L. Mather, Clairton, PA (US); Donald Archibald, Cheshire, CT (US)

(73) Assignee: Knopp Biosciences LLC, Pittsburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/926,812

(22) Filed: Mar. 20, 2018

(65) Prior Publication Data

US 2018/0271840 A1  Sep. 27, 2018

Related U.S. Application Data

(63) Continuation of application No. 15/492,832, filed on Apr. 20, 2017, now Pat. No. 9,956,206, which is a continuation of application No. 14/194,558, filed on Feb. 28, 2014, now Pat. No. 9,662,313.

(60) Provisional application No. 61/771,032, filed on Feb. 28, 2013, provisional application No. 61/772,328, filed on Mar. 4, 2013, provisional application No. 61/786,236, filed on Mar. 14, 2013, provisional application No. 61/911,984, filed on Dec. 4, 2013.

(51) Int. Cl.
  *A61K 31/428* (2006.01)
(52) U.S. Cl.
  CPC .................................. *A61K 31/428* (2013.01)
(58) Field of Classification Search
  CPC .................................................. A61K 31/428
  USPC ......................................................... 514/367
  See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 4,031,894 A | 6/1977 | Urquhart et al. |
| 4,144,317 A | 3/1979 | Higuchi et al. |
| 4,201,211 A | 5/1980 | Chandrasekaran et al. |
| 4,286,592 A | 9/1981 | Chandrasekaran |
| 4,314,557 A | 2/1982 | Chandrasekaran |
| 4,327,725 A | 5/1982 | Cortese et al. |
| 4,379,454 A | 4/1983 | Campbell et al. |
| 4,395,859 A | 8/1983 | Rohrer |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Chen et al. |
| 4,588,580 A | 5/1986 | Gale et al. |
| 4,612,008 A | 9/1986 | Wong et al. |
| 4,626,539 A | 12/1986 | Aungst et al. |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,731,374 A | 3/1988 | Griss et al. |
| 4,781,924 A | 11/1988 | Lee et al. |
| 4,783,337 A | 11/1988 | Wong et al. |
| 4,788,062 A | 11/1988 | Gale et al. |
| 4,806,341 A | 2/1989 | Chien et al. |
| 4,816,258 A | 3/1989 | Nedberge et al. |
| 4,843,086 A | 6/1989 | Griss et al. |
| 4,849,226 A | 7/1989 | Gale |
| 4,886,812 A | 12/1989 | Griss et al. |
| 4,904,475 A | 2/1990 | Gale et al. |
| 4,908,027 A | 3/1990 | Enscore et al. |
| 4,917,895 A | 4/1990 | Lee et al. |
| 4,938,759 A | 7/1990 | Enscore et al. |
| 4,943,435 A | 7/1990 | Baker et al. |
| 5,004,610 A | 4/1991 | Osborne et al. |
| 5,024,843 A | 6/1991 | Kuczynski et al. |
| 5,069,909 A | 12/1991 | Sharma et al. |

(Continued)

FOREIGN PATENT DOCUMENTS

| | | |
|---|---|---|
| AU | 2006279643 A1 | 2/2007 |
| AU | 2002360600 B2 | 11/2007 |

(Continued)

OTHER PUBLICATIONS

Abrahamson et al. "Structure and expression of the human cystatin C gene" 1990, Biochem J. 268(2):287-294.
Abramova et al. "Inhibition by R(+) or S(−) Pramipexole of Caspase Activation and Cell Death Induced by Methylpyridinium Ion or Beta Amyloid Peptide in SH-SY5Y Neuroblastoma" 2002, J. Neurosc. Res. 67(4):494-500. XP009075274.
Agardh et al. "Expression of antioxidant enzymes in rat retinal ischemia followed by reperfusion" Jul. 2006, Metabolism 55(7):892-898 (Abstract).
Aguila et al. "Prognosis in Amyotrophic Lateral Sclerosis: A population based study" 2003, Neurology 60:813-819.
Akintola-Ogunremi et al., "Chronic lymphocytic leukemia presenting with symptomatic centeral nervous system involvement," Ann. Hematol. (2002), (81) pp. 402-404.

(Continued)

*Primary Examiner* — Kristin A Vajda
(74) *Attorney, Agent, or Firm* — Pepper Hamilton LLP

(57) ABSTRACT

A method for treating amyotrophic lateral sclerosis (ALS) in a subject in need thereof comprising administering to said subject an effective amount of (6R)-2-amino-4,5,6,7-tetrahydro-6-(propylamino)benzothiazole or pharmaceutically acceptable salt thereof, wherein said subject is a treatment responder. In certain embodiments, said subject is a subject with definite amyotrophic lateral sclerosis, a subject with amyotrophic lateral sclerosis symptom onset duration of less than about 18 months, a subject with a high level of serum creatinine, a subject with concomitant riluzole administration and combinations thereof.

21 Claims, 67 Drawing Sheets

(56) References Cited

U.S. PATENT DOCUMENTS

| | | |
|---|---|---|
| 5,071,656 A | 12/1991 | Lee et al. |
| 5,082,668 A | 1/1992 | Wong et al. |
| 5,091,190 A | 2/1992 | Kuczynski et al. |
| 5,112,842 A | 5/1992 | Zierenberg et al. |
| 5,122,382 A | 6/1992 | Gale et al. |
| 5,141,750 A | 8/1992 | Lee et al. |
| 5,284,660 A | 2/1994 | Lee et al. |
| 5,314,694 A | 5/1994 | Gale et al. |
| 5,342,623 A | 8/1994 | Enscore et al. |
| 5,411,740 A | 5/1995 | Lee et al. |
| 5,442,117 A | 8/1995 | Stahly et al. |
| 5,545,413 A | 8/1996 | Kuczynski et al. |
| 5,591,454 A | 1/1997 | Kuczynski et al. |
| 5,635,203 A | 6/1997 | Gale et al. |
| 5,650,420 A | 7/1997 | Hall et al. |
| 5,674,895 A | 10/1997 | Guittard et al. |
| 5,719,060 A | 2/1998 | Hutchens et al. |
| 5,792,664 A | 8/1998 | Chait et al. |
| 5,804,215 A | 9/1998 | Cubbage et al. |
| 5,830,497 A | 11/1998 | Yamanaka et al. |
| 5,840,754 A | 11/1998 | Guittard et al. |
| 5,912,268 A | 6/1999 | Guittard et al. |
| 6,043,251 A | 3/2000 | Douillet et al. |
| 6,156,777 A | 12/2000 | Hall et al. |
| 6,187,802 B1 | 2/2001 | Cheetham et al. |
| 6,197,339 B1 | 3/2001 | Ju |
| 6,228,398 B1 | 5/2001 | Devane et al. |
| 6,255,329 B1 | 7/2001 | Maj |
| 6,262,115 B1 | 7/2001 | Guittard et al. |
| 6,284,774 B1 | 9/2001 | Wright et al. |
| 6,294,790 B1 | 9/2001 | Weinberger |
| 6,443,976 B1 | 9/2002 | Flower et al. |
| 6,458,820 B1 | 10/2002 | Hall et al. |
| 6,480,820 B1 | 11/2002 | Clopton et al. |
| 6,541,486 B1 | 4/2003 | Bitler et al. |
| 6,618,138 B2 | 9/2003 | Khoury |
| 6,667,329 B1 | 12/2003 | Maj |
| 6,675,104 B2 | 1/2004 | Paulse et al. |
| 6,727,367 B2 | 4/2004 | Pospisilik |
| 6,730,325 B2 | 5/2004 | Devane et al. |
| 6,750,235 B1 | 6/2004 | Rosenbaum |
| 6,776,984 B1 | 8/2004 | Schwartz |
| 6,793,936 B2 | 9/2004 | Devane et al. |
| 6,902,742 B2 | 6/2005 | Devane et al. |
| 6,919,092 B2 | 7/2005 | Guittard et al. |
| 6,919,373 B1 | 7/2005 | Lam et al. |
| 6,927,036 B2 | 8/2005 | Gallop et al. |
| 6,929,801 B2 | 8/2005 | Klose et al. |
| 6,930,129 B2 | 8/2005 | Lam et al. |
| 7,005,255 B2 | 2/2006 | Kaddurah-Daouk et al. |
| 7,157,480 B2 | 1/2007 | Bennett, Jr. |
| 7,285,669 B2 | 10/2007 | Rao et al. |
| 7,344,733 B2 | 3/2008 | Beier et al. |
| 7,572,596 B2 | 8/2009 | Bowser |
| 7,741,490 B2 | 6/2010 | Castaldi et al. |
| 8,017,598 B2 | 9/2011 | Bozik et al. |
| 8,186,890 B2 | 5/2012 | Lu |
| 8,192,091 B2 | 6/2012 | Hsu et al. |
| 8,408,815 B2 | 4/2013 | Lin et al. |
| 8,445,474 B2 | 5/2013 | Bozik et al. |
| 8,518,926 B2 | 8/2013 | Bozik et al. |
| 8,519,148 B2 | 8/2013 | Raje et al. |
| 8,524,695 B2 | 9/2013 | Bozik et al. |
| 9,468,630 B2 | 10/2016 | Bozik et al. |
| 9,642,840 B2 | 5/2017 | Bozik et al. |
| 9,662,313 B2* | 5/2017 | Bozik .................. A61K 31/428 |
| 9,956,206 B2* | 5/2018 | Bozik .................. A61K 31/428 |
| 2002/0004058 A1 | 1/2002 | Yoshii et al. |
| 2002/0103240 A1 | 8/2002 | Pospisilik |
| 2002/0106731 A1 | 8/2002 | Ruben et al. |
| 2002/0151526 A1 | 10/2002 | Gallop et al. |
| 2002/0177626 A1 | 11/2002 | Cook et al. |
| 2003/0013120 A1 | 1/2003 | Patz et al. |
| 2003/0049318 A1 | 3/2003 | Davis et al. |
| 2003/0166696 A1 | 9/2003 | Warsinsky et al. |
| 2003/0203055 A1 | 10/2003 | Rao et al. |
| 2004/0014721 A1 | 1/2004 | Hensley et al. |
| 2004/0031667 A1 | 2/2004 | Dinkel et al. |
| 2004/0033530 A1 | 2/2004 | Awrey et al. |
| 2004/0067991 A1 | 4/2004 | Greig et al. |
| 2004/0097540 A1 | 5/2004 | Peters et al. |
| 2004/0122104 A1 | 6/2004 | Hirsh et al. |
| 2004/0132788 A1 | 7/2004 | Chabrier De Lassauniere et al. |
| 2004/0132826 A1 | 7/2004 | Hirsh et al. |
| 2004/0219213 A1 | 11/2004 | Burnside et al. |
| 2004/0247656 A1 | 12/2004 | Beier et al. |
| 2004/0265370 A1 | 12/2004 | Odidi et al. |
| 2005/0031667 A1 | 2/2005 | Patel et al. |
| 2005/0032856 A1 | 2/2005 | Bennett |
| 2005/0053649 A1 | 3/2005 | Chalmers |
| 2005/0059717 A1 | 3/2005 | van Eupen et al. |
| 2005/0070715 A1 | 3/2005 | Bhat et al. |
| 2005/0074865 A1 | 4/2005 | Afeyan et al. |
| 2005/0089575 A1 | 4/2005 | Friedl et al. |
| 2005/0148026 A1 | 7/2005 | Bowser et al. |
| 2005/0208156 A1 | 9/2005 | Ploch et al. |
| 2005/0220877 A1 | 10/2005 | Patel et al. |
| 2005/0226926 A1 | 10/2005 | Amidon et al. |
| 2005/0265379 A1 | 12/2005 | Rao |
| 2006/0009659 A1 | 1/2006 | Maywald et al. |
| 2006/0046967 A1 | 3/2006 | Satyam |
| 2006/0051419 A1 | 3/2006 | Friedl et al. |
| 2006/0069263 A1 | 3/2006 | Gribun et al. |
| 2006/0099257 A1 | 5/2006 | Langridge et al. |
| 2006/0106224 A1 | 5/2006 | Gupta et al. |
| 2006/0110450 A1 | 5/2006 | Eisenreich |
| 2006/0121619 A1 | 6/2006 | Bowser |
| 2006/0128643 A1 | 6/2006 | Kaddurah-Daouk et al. |
| 2006/0141037 A1 | 6/2006 | Mehta et al. |
| 2006/0148866 A1 | 7/2006 | Xia et al. |
| 2006/0281797 A1 | 12/2006 | Bennett |
| 2006/0286167 A1 | 12/2006 | Staunton et al. |
| 2007/0087410 A1 | 4/2007 | Lanahan et al. |
| 2007/0105918 A1 | 5/2007 | Bennett, Jr. |
| 2007/0203209 A1 | 8/2007 | Bartolini et al. |
| 2007/0259930 A1 | 11/2007 | Bozik et al. |
| 2008/0014259 A1 | 1/2008 | Bozik et al. |
| 2008/0020028 A1 | 1/2008 | Shevchuk et al. |
| 2008/0026043 A1 | 1/2008 | Mueller et al. |
| 2008/0081041 A1 | 4/2008 | Nemeth |
| 2008/0096939 A1 | 4/2008 | Keil et al. |
| 2008/0194832 A1 | 8/2008 | Silva Guisasola et al. |
| 2008/0227985 A1 | 9/2008 | Raje et al. |
| 2008/0234338 A1 | 9/2008 | Bennett, Jr. |
| 2009/0042956 A1 | 2/2009 | Bozik et al. |
| 2009/0054504 A1 | 2/2009 | Bozik et al. |
| 2009/0105483 A1 | 4/2009 | Balicki et al. |
| 2009/0149518 A1 | 6/2009 | Nishii et al. |
| 2010/0291073 A1 | 11/2010 | Koike et al. |
| 2010/0292149 A1 | 11/2010 | Bowser |
| 2011/0009460 A1 | 1/2011 | Gribkoff et al. |
| 2011/0020339 A1 | 1/2011 | Hargreave et al. |
| 2011/0190356 A1 | 8/2011 | Bozik et al. |
| 2011/0218222 A1 | 9/2011 | Bennett, Jr. |
| 2011/0224268 A1 | 9/2011 | Bozik et al. |
| 2011/0293718 A1 | 12/2011 | Bozik et al. |
| 2011/0301210 A1 | 12/2011 | Bennett, Jr. |
| 2012/0134929 A1 | 5/2012 | McGrath et al. |
| 2012/0142715 A1 | 6/2012 | Kim |
| 2012/0148575 A1 | 6/2012 | Koike et al. |
| 2012/0225915 A1 | 9/2012 | Bozik et al. |
| 2012/0253047 A1 | 10/2012 | Allegrini et al. |
| 2012/0258994 A1 | 10/2012 | McKinney et al. |
| 2013/0059801 A1 | 3/2013 | Milne et al. |
| 2013/0079526 A1 | 3/2013 | Greenfield et al. |
| 2013/0116292 A1 | 5/2013 | Bennett, Jr. |
| 2013/0123312 A1 | 5/2013 | Bozik et al. |
| 2013/0172394 A1 | 7/2013 | Bennett, Jr. |
| 2013/0230569 A1 | 9/2013 | Bozik et al. |
| 2013/0245081 A1 | 9/2013 | Gribkoff et al. |
| 2013/0273557 A1 | 10/2013 | Gribkoff et al. |
| 2013/0310430 A1 | 11/2013 | Bozik et al. |
| 2014/0018343 A1 | 1/2014 | Romero et al. |
| 2014/0031401 A1 | 1/2014 | Bozik et al. |

(56) References Cited

U.S. PATENT DOCUMENTS

| | | |
|---|---|---|
| 2014/0100372 A1 | 4/2014 | Raje et al. |
| 2014/0329869 A1 | 11/2014 | Bozik et al. |
| 2015/0018397 A1 | 1/2015 | Bozik et al. |
| 2015/0126745 A1 | 5/2015 | Chen et al. |
| 2016/0022647 A1 | 1/2016 | Bozik et al. |
| 2016/0030397 A1 | 2/2016 | Bozik et al. |
| 2016/0158205 A1 | 6/2016 | Bozik et al. |
| 2016/0193186 A1 | 7/2016 | Bozik et al. |
| 2016/0193187 A1 | 7/2016 | Bozik et al. |
| 2017/0158648 A1 | 6/2017 | Chen et al. |
| 2017/0281604 A1 | 10/2017 | Bozik et al. |
| 2017/0281605 A1 | 10/2017 | Bozik et al. |

FOREIGN PATENT DOCUMENTS

| | | |
|---|---|---|
| AU | 2007333050 B2 | 8/2013 |
| CA | 2619217 A1 | 2/2007 |
| CA | 2605078 C | 1/2013 |
| CN | 1617720 A | 5/2005 |
| CN | 1735604 A | 2/2006 |
| CN | 1308533 C | 4/2007 |
| CN | 101641096 A | 2/2010 |
| CN | 101677564 A | 3/2010 |
| CN | 102160865 A | 8/2011 |
| CN | 102772404 A | 11/2012 |
| CN | 102802418 A | 11/2012 |
| EP | 0186087 B1 | 8/1989 |
| EP | 0558861 A1 | 9/1993 |
| EP | 1453505 A4 | 1/2007 |
| EP | 2156833 A4 | 11/2010 |
| EP | 2305252 A1 | 4/2011 |
| EP | 2465500 A1 | 6/2012 |
| EP | 2497472 A1 | 9/2012 |
| EP | 2497473 A1 | 9/2012 |
| EP | 2497474 A1 | 9/2012 |
| EP | 2542541 A1 | 1/2013 |
| EP | 2442655 A4 | 4/2013 |
| EP | 2246053 B1 | 9/2013 |
| HK | 1156238 A | 6/2012 |
| HK | 1156239 A | 8/2012 |
| JP | H07504655 A | 5/1995 |
| JP | 10510809 | 10/1998 |
| JP | 2003511416 A | 3/2003 |
| JP | 2005516911 A | 6/2005 |
| JP | 2005525345 A | 8/2005 |
| JP | 2005527540 A | 9/2005 |
| JP | 2006502188 A | 1/2006 |
| JP | 2006143708 A | 6/2006 |
| JP | 2006516549 A | 7/2006 |
| JP | 2008502609 A | 1/2008 |
| JP | 2008527002 A | 7/2008 |
| JP | 2009504748 A | 2/2009 |
| JP | 2010031059 A | 2/2010 |
| JP | 2010513316 A | 4/2010 |
| JP | 4500543 B2 | 7/2010 |
| JP | 11515012 | 5/2011 |
| JP | 2012500283 A | 1/2012 |
| JP | 2012530723 A | 12/2012 |
| JP | 2013014629 A | 1/2013 |
| JP | 6155377 B2 | 6/2017 |
| RU | 2009126742 A | 1/2011 |
| RU | 2491068 C2 | 8/2013 |
| WO | 199317683 A1 | 9/1993 |
| WO | 1993024834 A1 | 12/1993 |
| WO | 1996018395 A1 | 6/1996 |
| WO | 1997015304 A1 | 5/1997 |
| WO | 1998059360 A9 | 4/1999 |
| WO | 2001013902 A2 | 3/2001 |
| WO | 2001022820 A1 | 4/2001 |
| WO | 2001062249 A1 | 8/2001 |
| WO | 2003049705 A3 | 1/2004 |
| WO | 2004002520 A1 | 1/2004 |
| WO | 2003070188 A3 | 2/2004 |
| WO | 2004010999 A1 | 2/2004 |
| WO | 2004041797 A1 | 5/2004 |
| WO | 2004026246 A3 | 7/2004 |
| WO | 2004058163 A3 | 10/2004 |
| WO | 2005011687 A1 | 2/2005 |
| WO | 2004050034 A3 | 4/2005 |
| WO | 2005092871 A3 | 12/2005 |
| WO | 2005123193 A3 | 3/2006 |
| WO | 2006043532 A1 | 4/2006 |
| WO | 2006012277 A3 | 8/2006 |
| WO | 2006003471 A3 | 9/2006 |
| WO | 2006015943 A3 | 2/2007 |
| WO | 2006015944 A3 | 2/2007 |
| WO | 2007022182 A1 | 2/2007 |
| WO | 2007045620 A1 | 4/2007 |
| WO | 2007046347 A1 | 4/2007 |
| WO | 2006076681 A3 | 6/2007 |
| WO | 2007075095 A1 | 7/2007 |
| WO | 2007076062 A | 7/2007 |
| WO | 2006116369 A3 | 8/2007 |
| WO | 2007137071 A1 | 11/2007 |
| WO | 2007090882 A3 | 12/2007 |
| WO | 2008023027 A1 | 2/2008 |
| WO | 2008041240 A1 | 4/2008 |
| WO | 2008052953 A1 | 5/2008 |
| WO | 2008074033 A1 | 6/2008 |
| WO | 2008113003 A2 | 9/2008 |
| WO | 2008113056 A | 9/2008 |
| WO | 2007121188 A3 | 11/2008 |
| WO | 2008104847 A3 | 2/2009 |
| WO | 2010022140 A2 | 2/2010 |
| WO | 2010148409 A1 | 12/2010 |
| WO | 2011109596 A1 | 9/2011 |
| WO | 2011150221 A3 | 2/2012 |
| WO | 2012019015 A3 | 5/2012 |
| WO | 2013034550 A1 | 3/2013 |
| WO | 2013096816 A1 | 6/2013 |
| WO | 2013096870 A1 | 6/2013 |
| WO | 2014134569 A1 | 9/2014 |
| WO | 2015006708 A1 | 1/2015 |
| WO | 2015023786 A1 | 2/2015 |
| WO | 2015023790 A1 | 2/2015 |
| WO | 2015061777 A1 | 4/2015 |

OTHER PUBLICATIONS

Anonymous "Variant of Parkinson's Drug Tested in ALS" Jul. 19, 2006 (printed from www.als-mda.org/research/news/060719als.sub.-pramipexole.html on Feb. 21, 2008) (Abstract).
Anosova et al. "Antigenecity and Immunogenicity of Allogeneic Retinal Transplants" Oct. 2001, J. Clin. Invest. 108(8):1175-1183.
Ansel et al. "Pharmaceutical Dosage Forms and Drug Delivery Systems, 6.sup.th.ed." 1995, Williams and Wilkins Media, Malvern, PA (TOC).
Anthony et al. "Protective Immune Mechanisms in Helminth Infection" Dec. 2007, Nat Rev Immunol. 7(12):975-987.
Arico et al., Restless Legs Syndrome as the Presenting Symptom of Multiple Myeloma, Journal of Clinical Sleep Medicine (2013), 9(4) pp. 383-385.
Brooks, et al., "El Escorial revisited: Revised criteria for the diagnosis of amyotrophic lateral sclerosis", 2000, ALS and other motor neuron disorders, vol. 1, pp. 293-299.
Asgeirsson, et al., "Hereditary cystatin C amyloid angiopathy: monitoring the presence of the Leu-68 --> Gln cystatin C variant in cerebrospinal fluids and monocyte cultures by MS", Biochem. J., 329 (Pt 3):497-503 (1998).
Ashcroft et al. "An Efficient and Scalable Synthesis of the Endothelin Antagonists UK-350,926 and UK-349,862 Using a Dynamic Resolution Process" 2005, Organic Proc. Res. & Dev. 9:663-669.
B.R. Brooks, "El Escorial World Federation of Neurology Criteria for the Diagnosis of Amyotrophic Lateral Sclerosis", 1994, Journal of the Neurological Sciences, vol. 124, Suppl., pp. 96-107.
Balicki et al. "A New, Efficient and Economic Method for Preparation of Pramipexole" May 16, 2006, Book of Abstracts: The Fifth Multidisciplinary conference on Drug Research, Pielaszek Research (Warszawa, Poland) Poster No. 1-19, p. 30 (EnglishAbstract).
Balicki et al., "New Method for Preparing Pramipexole Dihydrochloride Monohydrate", Przemsl Chemiczny, 85(6), 344-346, 2006. (Abstract only, ChemicalAbstracts, 146500932, 2006.

(56) References Cited

OTHER PUBLICATIONS

Banker et al. "Modern Pharmaceutics" 1979, Marcel Dekker, Inc. (TOC).
Beal "Oxidative Metabolism" 2000, Ann. N.Y. Acad. Sci. 924:164-169.
Beatty et al. "The Role of Oxidative Stress in the Pathogenesis of Age-Related Macular Degeneration" 2000, Surv. Opthalmol 45(2):115-134.
Benson et al., "Identification of Carriers of a Variant Plasma Prealbumin (Transthyretin) Associated With Familial Amyloidotic Polyneuropathy Type I," The Journal of Clinical Investigation, 75: 71-75 (1985).
Berge et al., Pharmaceutical Salts, 1977, J. Pharm. Sciences 66(1):1-19.
Bergen et al., "Identification of Transthyretin Variants by Sequential Proteomic and Genomic Analysis," Clinical Chemistry, 50(9): 1544-1552 (2004).
Bernstein et al., "Transthyretin: Its Response to Malnutrition and Stress Injury" Clin Chem Lab Med, 40(12): 1344-1348 (2002).
Biglan et al. "A Review of Pramipexole and its Clinical Utility in Parkinson's Disease" 2002, Expert Opinion Pharmacotherapy 3(2):197-210.
Borchelt et al., "Superoxide Dismutase 1 With Mutations Linked to Familial Amyotrophic Lateral Sclerosis Possesses Significant Activity," Proc. Natl. Acad. Sci. USA, 91(17): 8292-8296 (Aug. 16, 1994).
Bozik et al. "Safety, Tolerability, and Pharmacokinetics of KNS-760704 (Dexpramipexole) in Healthy Adult Subjects" 2011, J. Clin. Pharmacol. 51:1177-1185.
Bozik et al. "Phase 2 Study of the Safety Tolerability and Clinical Effects of KNS 760704 in ALS Subjects" Dec. 20, 2009 International Symposium on ALSMND Abstract C40.
Carvey, et al. "Attenuation of levodopa-induced toxicity in mesencephalic cultures by pramipexole" 1997, J. Neural. Transm. 209-228.
Cassarino et al. "An evaluation of the role of mitochondria in neurodegenerative diseases: mitochondrial mutations and oxidative pathology, protective nuclear responses, and cell death in neurodegeneration" 1999, Brain Res. Rev. 29:1-25.
Cassarino et al. "Cyclosporin a increases resting mitochondrial membrane potential in SY5Y cells and reverses the depressed mitochondrial membrane potential of Alzheimer's disease cybrids" May 13, 1998, Biochem. and Biophysical Research Comm.248:168-173.
Cassarino et al. "Pramipexole reduces reactive oxygen species production in vivo and in vitro and inhibits the mitochondrial permeability transition produced by the parkinsonian neurotoxin methylpyridinium ion" 1998, J. Neurochem. 71(1):295-301.
Cassarino, et al. "Interaction among mitochondria, mitogen-activated protein kinases, and nuclear factor-kappaB in cellular models of Parkinson's disease" Apr. 2000, J Neurochem 74(4):1384-92. PubMed PMID: 10737593.
Cleveland et al. "From Charcot to Lou Gehrig: deciphering selective motor neuron death in ALS" 2001, Nat. Rev. Neurosci. 2:806-819.
Corcoran et al. "Absence of retinoids can induce motoneuron disease in the adult rat and a retinoid defect is present in motoneuron disease patients" 2002, J. Cell. Sci. 115:4735-4741.
Corrigan et al. "Comparison of Pramipexole, Fluoxetine, and Placebo in Patients with Major Depression" 2000, Depression and Anxiety 11:58-65.
Cudkowicz et al. "Dexpramipexole versus placebo for patients with amyotrophic lateral sclerosis (EMPOWER): a ramdomised double-blind, phase 3 trial" Lancet Neurol. (2013), (12) pp. 1059-1067.
Cudkowicz et al. "Measures and Markers in Amyotrophic Lateral Sclerosis" 2004, NeuroRx: The Journal of the American Society for Experimental Neuro Therapeutics 1(2):273-283.
Cudkowicz et al., "The effects of dexpramipexole (KNS-760704) in individuals with amyotrophic lateral sclerosis", Dec. 2011, Nature Medicine, vol. 17, No. 12, pp. 1652-1656; Supplemental Materials included with total of 27 pages.
Danseizen at al., Targeted Antioxidative and Neuroprotective Properties of the Dopamine Agonist Pramipexole and its Nondopaminergic Enantiomer SND919CL2x [(+)2-Amino-4, 5, 6, 7-tetrahydro-6-L-propylamino-benzathiazole Dihydrochloride], 2006, J.Pharmacol. Exp. Ther. 316:189-199.
Davis et al. "Eosinophils and Cancer" Aug. 20, 2014, Cancer Immunol Res. 2(1):1-8-p. 5.
Declaration of James P. Bennett Under 37 C.F.R. 1.132 dated Dec. 15, 2009.
Deigner et al. "Apoptosis Modulators in the Therapy of Neurodegenerative Diseases" Apr. 2000, Ex. Opin. Investigational Drugs 9(4):747-764 XP001012423.
Deng et al. "Elevation of cystatin C in susceptible neurons in Alzheimer's disease" 2001, Am. J. Pathol. 159(3):1061-1068.
Dooley et al. "Pramipexole. A Review of its Use in the Managemetn of Early and Advanced Parkinson's Disease" Jun. 1998, Drugs Aging 12(6):495-514.
Drobny et al. "Possible Extrapyramidal System Degradation in Parkinson's Disease" 2000, Brain Research Bulletin 53(4):425-430.
Email correspondence from James P. Bennett to Michael Bozik dated Apr. 6, 2007 with a draft manuscript entitled "R(+) Pramipexole as a Neuroprotectant I: Effects of R(+) Pramipexole Treatment of ALS on ALSFRSr, Forced Vital Capacity andNeurophysiological Index".
Email correspondence from James P. Bennett to Michael Bozik dated Apr. 6 2007 with a draft manuscript entitled "R(+) Pramipexole as a Neuroprotectant II: Tolerability and Pharmacokinetics in ALS of Esclating Doses to 300mgday".
Email correspondence from James P. Bennett to Michael Bozik dated May 11, 2006 with a presentation entitled "ALS: An Investigator's View of the Disease and its Treatment".
Email correspondence from James P. Bennett to Michael Bozik dated Oct. 9, 2006 with a draft grant application.
European Seach Report and Opinion dated Aug. 1, 2012 for EP 12163888.
Schmidt et al. "Neurodegenerative diseases of the retina and potential for protection and recovery" Jun. 2008 (printed from http://www.nncbi.nim,nih.gov/pubmed/19305795?dopt.sub.-Abstract) Curr. Neuropharmacol. 6(2) (Abstract, 1 page).
Schneider et al. "Dopamine Autoreceptor Agonists: Resolution and Pharmacological Activity of 2,6-Diaminotetrahydrobenzothiazole and an Aminothiazole Analogue of Apomorphine" 1987, J. Med. Chem. 30:494-498.
Schuelke et al. "Myostatin Mutation Associated With Gross Muscle Hypertrophy in a Child" 2004, N. Engl. J. Med. 350:2682-2688 (Para.1).
Shannon et al. "Efficacy of Pramipexole, a Novel Dopamine Agonist, as Monotherapy in Mild to Moderate Parkinson's Disease" 1997, Neurology 49(3)a;724-728.
Sousa et al. "Deposition of transthyretin in early stages of familial amyloidotic polyneuropathy: evidence for toxicity of nonfibrillar aggregates" Dec. 2001, Am J Pathol. 159(6):1993-2000.
Sousa et al. "Evidence for early cytotoxic aggregates in transgenic mice for human transthyretin Leu55Pro" Nov. 2002, Am. J. of Pathol. 161(5):1935-1948.
Stein et al. "Neutralization of transthyretin reverses the neuroprotective effects of secreted amyloid precursor protein (APP) in APPsw mice resulting in tau phosphorylation and loss of hippocampal neurons: Support for the amyloid hypothesis" Sep. 1, 2004, J. Neurosci. 24(35):7707-7717.
The Foundation Fighting Blindness "Animal Models for Studying Inherited Degenerative Retinal Disease" 2000 (printed from www.retina-intemational.org/sci-news/animmod.doc on Jan. 11, 2009) The Foundation Fighting Blindness (23 pages).
Tobran-Tink et al. "Neuroprotection in Macular Degeneration" 2005, Age-Related Macular Degeneration: A Comprehensive Textbook (Lippincott Williams & Wilkins), 29:335-336.
Tsuzuki et al. "Structure of the Human Prealbumin Gene" Oct. 5, 1984, J. Biol. Chem. 260(22):12224-12227.
U.S. Dept. of HHS FDA CDER (Guidance for Industry), Jul. 2005, 30 pp.

(56) References Cited

OTHER PUBLICATIONS

Uemichi et al. "A New Mutant Transthyretin (Arg 10) Associated with Familial Amyloid Polyneuropathy" 1992, J. Med. Genet. 29:888-891.
Voskoglou-Nomikos et al., "Clinical Predictive Value of the in Vitro Cell Line, Human Xenograft, and Mouse Allograft Preclinical Cancer Models", Clinical Cancer Research (Sep. 15, 2003), 9:4227-4239.
Wang et al. "R+ pramipexole as a mitochondrially focused neuroprotectant: initial early phase studies in ALS" Feb. 2008, Amyotroph Lateral Scler. 9(1):50-58. PubMed PMID: 18270879.
Wedi et al. "Chronic urticarial serum induces histamine release, leukotriene production, and basophil CD63 surface expression-inhibitory effects of anti-inflammatory drugs" Journal of allegery and clinical immunology, Mar. 2000, 105(3):552-560.
Weller, The Idiopathic Hypereosinophilic Syndrome, 1994, Blood, 83(10), pp. 2759-2779.
Winkler et al. "Oxidative damage and age-related macular degeneration" Nov. 3, 1999, Mol. Vis. 5:32 (Abstract).
Wong "A 384-well cell-based phosphor-ERK assay for dopamine D2 and D3 receptors" 2004, Analytical Biochem. 333:265-272.
Wong et al. "Activation of Extracellular Signal-Regulated Kinase by Dopamine D2 and D3 Receptors" 2003, Society for Neuroscience Abstracts (retrieved on line at sfn.scholarone.com/itin2003/main.html?new.sub.-page.sub.-id=126&abstrac-t.sub.--id=3866&p.sub.-num=363.4&is.sub.-tech= on Jun. 23, 2008).
Worker "Novel Therapeutic Strategies" 1999, IDRUGS, Current Drugs Ltd. GB 2(9):848-852 (XP000972503).
Wright et al. "Influence of Probenecid (PR) and Cimetidine (C) on Pramipexole (PX) Pharmacokinetics" Feb. 1995, Clin. Pharmacol. & Ther. 59(2):p. II-99 (abstract).
Written Opinion of International Search Authority dated Aug. 15, 2005 for PCT/US2006/031831 (1802).
Zheng et al. "Purification and identification of an estrogen binding protein from rat brain: oligomycin sensitivity-conferring protein (OSCP), a subunit of mitochondrial F0F1-ATP synthase/ATPase" Jan. 1999, J. Ster. Biochem. Mol. Biol.68(1-2):65-75.
PDF regarding ALS from Florida Hospital, retrieved on Jul. 12, 2018.
Petit et al. "Oxygen consumption by cultured human cells is impaired by a nucleoside analogue cocktail that inhibits mitochondrial DNA synthesis" 2005, Mitochondrion 5:154-161.
Fernandez et al. "Thyroid hormone administration enhances remyelination in chronic demyelinating inflammatory disease" Nov. 16, 2004 PNAS USA 101(46):16363-16368.
European Search Report and Opinion dated Aug. 2, 2012 for EP 12164060.
European Search Report and Opinion dated May 10, 2012 for EP 11186875.
European Search Report dated Feb. 18, 2011 for EP 10009931.
European Search Report dated Mar. 2, 2011 for EP 10075571.9.
European Supplemental Search Report dated Apr. 8, 2010 for EP 08743922 (903).
European Supplemental Search Report dated Apr. 9, 2010 for EP 08732306.9 (503).
European Supplemental Search Report dated Nov. 23, 2006 for EP02795869.
European Supplemental Search Report dated Oct. 4, 2010 for EP 10008579.4.
Extended European Search Report and Written Opinion dated Sep. 11, 2012 for EP 12164067.
Extended European Supplemental Search Report and Written Opinion dated Feb. 18, 2011 for EP10075571.
Feher et al. "Mitochondrial alternations of retinal pigment epithelium in age-related macular degeneration" Jun. 2006 (Printed from http://www.neurobiologyofaging.org/article/PIISO1974580005001545 on Dec. 11, 2009) Neurobiology of Aging 27(7)(Abstract, 2 pages).
Ferger et al. "The dopamine agonist pramipexole scavenges hydroxyl free radicals induced by striatal application of 6-hydroxydopamine in rats: an in vivo microdialysis study" Aug. 29, 2000, Brain Research 883:216-223.
Gennaro "Remington: The Science and Practice of Pharmacy, 20.sup.th Ed." Lippincott Williams & Wilkins, Baltimore, MD, 2000, Ch. 38:704-720.
Golebiewski et al. "Application of GC/MS for Identyfication of the Sideproducts in a Process of Preparation of Pramipexole" May 16, 2006, Book of Abstracts: The Fifth Multidisciplinary conference on Drug Research, Pielaszek Research (Warszawa,Poland) Poster No. 1-57, p. 49.
Goodall et al. "Association of the H63D polymorphism in the hemochromatosis gene with sporadic ALS" 2005, Neurology 65(6):934-937.
Goodman et al. "The Pharmaceutical Basis of Therapeutics, 6.sup.th Ed." 1980, MacMillan Publishing Co., New York (TOC).
Graves et al. "Inflammation in amyotrophic lateral sclerosis spinal cord and brain is mediated by activated macrophages mast cells and T cells" Amyotrophic Lateral Sclerosis and Other Motor Neuron Disorders Official Publication of the rld Federation of Neurology Research Group on Motor Neuron Diseases Dec. 5, 2004(4):213-219.
Gu et al., Pramipexole protects against apoptotic cell death by non-dopaminergic mechanisms, 2004, J. Neurochem. 91:1075-1081.
Gurney et al. "Motor Neuron Degeneration in Mice That Express a Human Cu, Zn Superoxide Dismutase Mutation" 1994, Science 264:1772-1775.
Haghikia et al. "Therapies for multiple sclerosis: translation achievements and outstanding needs" May 2013 Trends in Moleecular Medicine 19(5):309-319.
Halestrap "The Role of Mitochondria in Cell Death" Mar. 24, 2003, Endocrine Abstracts 5:513 (Abstract).
Hall et al. "Brain hydroxyl radical generation in acute experimental head injury" Feb. 1993, J. Neurochem. 60(2):588-594.
Hall et al. "Neuroprotective effects of the dopamine D.sub.2 / D.sub.3 agonist pramipexole against postischemic or methamphetamine-induced degeneration of nigrostriatal neurons" Aug. 6, 1996, Brain Research 742:80-88 (abstract).
Hansen et al. "First Generation Process for the Preparation of the DPP-IV Inhibitor Sitagliptin" 2005, Organic Proc. Res. & Dev. 9:634-639.
Hardy et al. "Genetic Classification of Primary Neurodegenerative Disease" Nov. 6, 1998, Science 282(5391):1075-1079.
Hasegawa et al. "A New Process for Synthesis of the Astrcyte Activation Suppressor, ONO-2506" 2005, Organic Proc. Res. & Dev. 9:774-781.
Hubble Pre-clinical Studies of Pramipexole: Clinical Relevance May 2000 Eur. J. Neurol. 7(Supp 1):15-20.
Initial Scientific Discussion for the Approval of Mirapex from the European Agency for the Evaluation of Medicinal Products (EMEA) 2005 www.emea.europa.eu/humandocs/PDFS/EPAR/Mirapexin/059097en6.pdf.
International Search Report and Written Opinion for PCT/US2008/057158 dated Jun. 29, 2009.
International Search Report and Written Opinion for PCT/US2010/39379 dated Aug. 25, 2010.
International Search Report and Written Opinion for PCT/US2013/054804 dated Mar. 21, 2014.
International Search Report and Written Opinion for PCT/US2014/019668 dated Jun. 9, 2014.
International Search Report and Written Opinion for PCT/US2014/050943 dated Nov. 6, 2014.
International Search Report and Written Opinion for PCT/US2014/050951 dated Oct. 22, 2014.
International Search Report and Written Opinion for PCT/US2016/22067 dated Jun. 3, 2016.
International Search Report dated Apr. 4, 2008 for PCT/US2007/087639 (702).
International Search Report dated Dec. 12, 2011 for PCT/US2011/38159 (1602).

(56) References Cited

OTHER PUBLICATIONS

International Search Report dated Jul. 11, 2008 for PCT/US2008/057059 (902).
International Search Report dated Jul. 17, 2003 for PCT/US2002/39970.
International Search Report dated Oct. 22, 2009 for PCT/US2009/54292.
International Search Report for International Application No. PCT/US2014/46380 dated Dec. 10, 2014.
International Search Report for PCT/US2006/031831 dated Dec. 12, 2006.
Jacques at al., Enantiomers, Racemates and Resolutions, John Wiley and Sons, Inc., Canada, 1981 (TOC).
Johnson et al. (Relationships between drug activity and NCI preclinical in vitro and in vivo models and early clinical trials; British Journal of Cancer; (2001) 84 (10), 1424-1431).
Kato et al. "A neurosphere-derived factor, cystatin C, supports differentiation of ES cells into neural stem cells" 2006, PNAS USA 103(15):6019-6024.
Khan, et al., "Alzheimer's disease cybrids replicate beta-amyloid abnormalities through cell death pathways" Aug. 2000, Ann Neurol. 48(2):148-55. PubMed PMID: 10939564.
Kieburtz "Safety and Efficacy of Pramipexole in Early Parkinson Disease" 1997, JAMA 278(2):125-130.
Kitamura et al. "Protective Effects of the Antiparkinsonian Drugs Talipexole and Pramipexole against 1-Methyl-4-phenylpyridinium-Induced Apoptotic Death in Human Neuroblastoma Sh-Sy5Y Cells" 1998, Molecular Pharmacology 54:1046-1054.
Lahortiga et al. "Activity of imatinib in systemic mastocytosis with chronic basophilic leukemia and a PRKG2-PDGFRB fusion" 2008, Haematological/The Hematology Journal 93(1): 51-52, 55.
Le et al. "Antioxidant property of pramipexole independent of dopamine receptor activation in neuroprotection" 2000, J. Neural. Transm. 107(10):1165-73.
Lee et al. "Carcinogenicity Predictions for a Group of 30 Chemicals Undergoing Rodent Cancer Bioassays Based on Rules Derived from Subchronic Organ Toxicities" 1996, Environmental Health Perspectives 104(5):1059-1063.
Levy et al. "Stroke in Icelandic Patients With Hereditary Amyloid Angiopathy is Related to a Mutation in the Cystatin C Gene, An Inhibitor of Cysteine Proteases" 1989, The Journal of Experimental Medicine 169(5):1771-1778.
Liang et al. "Oxidative stress-induced mitochondrial DNA damage in human retinal pigment epithelial cells: a possible mechanism for RPE aging and age-related macular degeneration" 2003, Exp. Eye Res. 76(4):397-403.
Lieberman et al. "Clinical evaluation of pramipexole in advanced Parkinson's disease: Results of a double-blind, placebo-controlled, parallel-group study" 1997, Neurology 49:162-168.
Lieberman et al. "Pharmaceutical Dosage Forms: Disperse Systems" 1996, Marcel Dekker, Inc., New York vol. 2 (TOC).
Lieberman et al. "Pharmaceutical Dosage Forms: Tablets" 1989 Marcel Dekker Inc. New York vol. 1 (TOC).
Lin et al. "Large-scale protein identification using mass spectrometry" 2003, Biochimica et Biophysica Acta 16460-2):1-10.
Liou et al. ("Case Report Churg-Strauss syndrome presented as multiple intracerebral hemorrhage." Lupus [(1997);6:279-282).
Lofberg, et al. "Immunohistochemical characterization of the amyloid deposits and quantitation of pertinent cerebrospinal fluid proteins in hereditary cerebral hemorrhage with amyloidosis" 1987, Stroke 18(2):431-440.
Lomen-Hoerth "Amyotrophic lateral sclerosis from bench to bedside" 2008, Semin. Neurol. 28(2):205-211.
Love "Oxidative Stress in Brain Ischemia" Apr. 5, 1999, Brain Pathology 9(1)119-131 (Abstract).
Lucchinetti et al., "Inflammatory Cortical Demyelination in Early Multiple Sclerosis," The New England Journal of Medicine (2011), (365) pp. 2188-2197.

Malaspina et al. "Differential expression of 14 genes in amyotrophic lateral sclerosis spinal cord detected using gridded cDNA arrays" 2001, J. Neurochemistry 77(1):132-145.
Martens "Cloning and Sequence Analysis of Human Pituitary cDNA Encoding the Novel Polypeptide 7B2" 1988, FEBS Letters 234(1):160-164.
Martens et al. "The Novel Pituitary Polypeptide 7B2 is a Highly-Conserved Protein Coexpressed with Proopiomelanocortin," European Journal of Biochemistry, 181(1): 75-79 (Apr. 1989).
Matthews et al. "Assessment of the Health Effects of Chemicals in Humans: I. Qsar Estimation of the Maximum Recommended Therapeutic Dose (MRTD) and No Effect Level (NOEL) of Organic Chemicals Based on Clinical Trial Data" 2004, Current DrugDiscovery Technologies 1:61-76.
Mbikay et al. "Neuroendocrine secretory protein 7B2: structure, expression and functions" Jul. 15, 2001, Biochem J. 357(2):329-342.
Menzies et al. "Mitochondrial dysfunction in a cell culture model of familial amyotrophic lateral sclerosis" Jul. 2002, Brain 125(7):1522-1533.
Merck Manuals Online Medical Library, Age-Related Macular Degeneration (ARMD), 2005, printed Aug. 13, 2008 from http://www.merck.com/mmpe/print/sec09/ch106/ch106b.html, 2 pages.
Mey et al., "Retinoic Acid Signaling in the Nervous System of Adult Vertebrates," The Neuroscientist, 10(5): 409-421 (2004).
Mhatre et al. "Oxidative Stress and Neuroinflammation in Alzheimer's Disease and Amyotrophic Lateral Sclerosis; Common Links and Potential Therapeutic Targets" Apr. 2004, J. Alzheimers Dis. 6(2):147-157 (abstract only).
Mierau at al., Pramipexole binding and activation of cloned and expressed dopamine D.sub.2, D.sub.3 and D.sub.4 receptors, 1995, Eur. J. Pharmacol. 290:29-36.
Miklya et al. "A pharmacological analysis elucidating why, in contrast to (−)-deprenyl (selegiline), .alpha.-tocopherol was ineffective in the DATATOP study" 2003, Life Sciences 72:2641-2648.
Mirapex.RTM. Prescribing Information from Boehringer Ingelheim, 2006, http://www.biopsychiatry.com/pramipexole-mirapex.pdf (retrieved May 10, 2012).
Moore et al. "An Efficient and Operationally Convenient General Synthesis of Tertiary Amines by Direct Alkylation of Secondary Amines with Alkyl Halides in the Presence of Huenig's Base" 2005, ARKIVOC 6:287-292.
Nagai et al., "Rats Expressing Human Cytosolic Copper-Zinc Superoxide Dismutase Transgenes with Amyotrophic Lateral Sclerosis: Associated Mutations Develop Motor Neuron Disease," The Journal of Neuroscience, 21(23): 9246-9254 (Dec. 1, 2001).
National Institutes of Health/ U.S. National Library of Medicine, "Creatine phosphokinase test", Updated Jan. 9, 2015, URL of this page: //www.nlm.nih.gov/medlineplus/ency/article/003503.htm, pp. 1-4.
Nilsen et al. "Mitochondria as Therapeutic Targets of Estrogen Action in the Central Nervous System" Aug. 2004, Curr. Drug Targets—CNS & Neurol. Disorders 3(4):297-313.
Ong et al. "An Evaluation of the Use of Two-Dimensional Gel Electrophoresis in Proteomics" 2001, Biomolecular Engineenng 18(5):195-205.
Palliative (n.d.) The American Heritage.RTM. Stedman's Medical Dictionary, Retrieved Jun. 12, 2009, from Dictionary.com website: http://dictionary.com/browse/palliative.
Paquet et al. "The neuroendocrine precursor 7B2 is a sulfated protein proteolytically processed by a ubiquitous furin-like convertase" Jul. 29, 1994, J. Biol. Chem. 269(30):19279-19285.
Pattee et al. "Reduction of oxidative stress in amyotrophic lateral sclerosis following pramipexole treatment" Jan. 2003, Amyotrophic Lateral Sclerosis and Other Motor Neuron Disorders 4(2):90-95 (abstract).
Paulson "Protein Fate in Neurodegenerative Proteinopathies: Polyglutamine Diseases Join the (Mis) Fold" 1999, Am. J. Hum. Genet. 64(2):339-345.
Petersen et al., Impaired Mitochondria Activity in the Insulin-Resistant Offspring of Patients with Type 2 Diabetes, 2004, New England Journal of Medicine 350:664-671.

(56) References Cited

OTHER PUBLICATIONS

Piercey et al. "Excitation of type II anterior caudate neurons by stimulation of dopamine $D_3$ receptors" 1997, Brain Research 762:19-28.

Piercey et al. "Inhibition of dopamine neuron firing by pramipexole, a dopamine $D_3$ receptor-prefering agonist: comparison to other dopamine receptor agonists" 1996, European J. of Pharmac. 312:35-44.

Public Statement on Mirapex, Sudden Onset of Sleep from the European Agency for the Evaluation of Medicinal Products (EMEA), Jul. 19, 1999, www.emea.europa.eu/pdfs/human/press/pus/2064299.pdf.

Ranganathan et al, "Proteomic profiling of cerebrospinal fluid identifies biomarkers for amyotrophic lateral sclerosis" 2005, J Neurochem. 29:1461-1471.

Roberecht, Wim (2000). "Oxidative stress in amyotrophic lateral sclerosis." J. Neurol, vol. 247, pp. 1/1-1/6.

Roca-Santiago et al. "Alzheimer's Disease and Age-related Macular Degeneration" Feb. 2006, Arch. Soc. Esp. Oftalmol. 81 (2):73-78.

Rothstein et al. ".beta.-Lactam antibiotics offer neuroprotection by increasing glutamate transporter expression" 2005, Nature 433(7021):73-77.

Rowland et al. "Amyotrophic Lateral Sclerosis" May 2001, N Eng Journal of Medicine, 344:1688-1700.

Rudnicki et al., "Dexpramipexole effects on functional decline and survival in subjects with amyotrophic lateral sclerosis in a Phase II study: Subgroup analysis of demographic and clinical characteristics", Feb. 1, 2013, Amyotrophic LateralSclerosis and Frontotemporal Degeneration, vol. 14, pp. 44-51.

Ryberg et al. "Discovery and Verification of Amyotrophic Lateral Sclerosis Biomarkers by Proteomics" Jul. 2010, Muscle & Nerve 42(1):104-111.

Sanchez et al. "Cystatin C as a potential cerebrospinal fluid marker for the diagnosis of Creutzfeldt-Jakob disease" 2004, Proteomics 4(8):2229-2233.

Sayeed et al. "Patch Clamp Reveals Powerful Blockade of the Mitochondrial Permeability Transition Pore by the D2-Receptor Agonist Pramipexole" 2006, FASB Journal 20:556-558.

Schilling et al. "Neuroendocrine and side effect profile of pramipexole, a new dopamine receptor agonist, in humans" 1992, Clin. Pharmacol. Ther. 51:541-548.

* cited by examiner

EMPOWER: Beyond Topline

Figure 5

EMPOWER first look analyses

- Purportedly failed to meet primary endpoint (CAFS) or key secondary endpoints (including time to death to 18 months)
- Purportedly, no dex benefit in subpopulations analyzed *post-hoc*
  - Baseline ALSFRS-R, age, site of onset, gender, riluzole use, symptom duration
- Dexpramipexole development terminated
  - EMPOWER was purportedly definitive
  - CL201 was purportedly an "anomaly"
  - CL201 and EMPOWER populations were purportedly "identical"
  - No additional analyses purportedly planned
  - Purportedly, no intention to explore higher doses

Figure 6

CL201 and EMPOWER:
Covariate distribution across studies

| Subgroup (Baseline Characteristic) | CL201 | EMPOWER | p-value |
|---|---|---|---|
| Mean ALSFRS-R | 38.0 | 38.2 | 0.78 |
| Mean age | 57.0 | 57.1 | 0.93 |
| Site of onset (limb) | 82% | 75% | 0.13 |
| Gender (male) | 64% | 64% | 0.92 |
| Riluzole (yes) | 61% | 75% | 0.002 |
| Mean symptom duration | 14.1 months | 15.2 months | 0.038 |
| El Escorial (definite) | 46% | 32% | 0.005 |

Figure 8

EMPOWER covariates:
Impact on CAFS rank outcome

| Subgroup (Baseline characteristic) | Distribution | Covariate significance |
|---|---|---|
| Mean ALSFRS-R | 38.2 | <0.0001 |
| Mean age | 57.1 | <0.0001 |
| Site of onset (limb) | 75% | 0.0003 |
| Gender (male) | 64% | 0.0949 |
| Riluzole (yes) | 75% | 0.1393 |
| Mean symptom duration | 15.2 months | <0.0001 |
| El Escorial (definite) | 32% | 0.0125 |

Figure 11

CL201 analysis: covariate impact (post-hoc)

*Amyotrophic Lateral Sclerosis and Frontotemporal Degeneration, 2013; 14: 44-51* informa
healthcare

ORIGINAL ARTICLE

Dexpramipexole effects on functional decline and survival in subjects with amyotrophic lateral sclerosis in a Phase II study: Subgroup analysis of demographic and clinical characteristics STACY A. RUDNICKI, JAMES D. BERRY, EVAN INGERSOLL, DON ARCHIBALD, MERIT E. CUDKOWICZ, DOUGLAS A. KERR & YINGWEN DONG Table III. CAPS results† by DEX dose and subject subgroups.

| | | DEX dose† | | | | DEX dose‡ | | |
|---|---|---|---|---|---|---|---|---|
| Variable | Subgroup (n) | 50 mg | 300 mg | p-value | Subgroup (n) | 50 mg | 300 mg | p-value |
| Riluzole use | Yes (53) | 40.5 | 46.8 | 0.1346 | No (27) | 40.4 | 52.7 | 0.1623 |
| Age, years | <59 (44) | 41.3 | 52.9 | 0.1453 | ≥59 (36) | 39.4 | 49.2 | 0.2051 |
| Gender | Male (40) | 39.1 | 50.9 | 0.0828 | Female (30) | 43.4 | 50.6 | 0.4509 |
| Site of onset | Bulbar (16) | 39.4 | 38.0 | 0.8520 | Limb (74) | 40.5 | 54.0 | 0.0187 |
| ALSFRS-R at baseline | ≤35 (40) | 31.1 | 49.0 | 0.0454 | >35 (42) | 50.6 | 53.0 | 0.7537 |
| SVC, % predicted | ≤81 (37) | 32.4 | 45.1 | 0.0005 | >81 (43) | 50.7 | 58.1 | 0.3351 |
| Symptom duration, months | 18.7 (43) | 31.3 | 48.3 | 0.0259 | ≥18.7 (45) | 50.4 | 53.1 | 0.7118 |
| Diagnostic delay, months | <7.9 (45) | 37.6 | 48.0 | 0.1791 | ≥7.4 (45) | 43.0 | 53.9 | 0.1635 |
| Progression rate,§ per month | <0.7 (45) | 55.5 | 57.9 | 0.9752 | ≥0.7 (45) | 23.9 | 44.7 | 0.0031 |

ALSFRS-R: Amyotrophic Lateral Sclerosis Functional Rating Scale-Revised; CAPS: Combined Assessment of Function and Survival; DEX: dexpramipexole; SVC: slow vital capacity.
†Least squares means based on intent-to-treat population; a higher value indicates a better outcome.
‡▲ favors DEX 300-mg dose; ▼ favors DEX 50-mg dose.
§Defined as ALSFRS-R points per month.

Figure 12

Definite EMPOWER placebo subjects were fast decliners

| | CAFS (value) | difference | ALSFRS-R Slopes | difference | Mortality M18 | difference |
|---|---|---|---|---|---|---|
| Definite n=156 | 398 | 26% | -1.358 | 22% | 27.6% | -25% |
| Non-definite n=312 | 502 | | -1.064 | | 20.8% | |

Figure 14

Significant differences in study populations

- Significant covariate differences between studies
  - Riluzole use (p=0.002)
  - Symptom duration (p=0.038)
  - El Escorial definite (p=0.005)

- Impact of same covariates on EMPOWER CAFS
  - Riluzole use (p=0.1393)
  - Symptom duration (p<0.0001)
  - El Escorial definite (p=0.0125)

- Significant dex benefit seen in definite, early CL201 subjects
  - CAFS benefit directionally positive (+23%), but not significant in riluzole subjects (p=0.1946)

- Key question: Is there evidence of a dex benefit in an equivalent EMPOWER population?

Figure 15

EMPOWER and beyond

- Significant differences between Phase 2 and Phase 3 study populations
- Trends and significant treatment benefits noted in subpopulations representing 16% to 32% of EMPOWER study population
- Characterization of these subpopulations expected to be enriched through pharmacogenomic analysis of EMPOWER biosamples

Figure 23

Is EEC definite a surrogate for an ALS disease phenotype?

Multi-region presentation correlates with reduced survival

| Variable | Scoring | p |
|---|---|---|
| 1. Age | < 65 years = 1 > 65 years = 0 | 0.0003 |
| 2. Disease duration | > 2 years = 1 < 2 years = 0 | 0.0003 |
| 3. Plasma creatinine | > 60 μM = 1 < 60 μM = 0 | 0.0100 |
| 4. Atrophy | 0/1 regions = 2 1 region = 1 0 regions = 0 | 0.0030 |
| 5. Pyramidal signs | 3 regions = 3 2 regions = 2 1 region = 1 0 regions = 0 | 0.0140 |
| 6. Spasticity | 3 regions = 3 2 regions = 2 1 region = 1 0 regions = 0 | 0.0017 |
| 7. Fasciculations | 0/1/2 regions = 1 3 regions = 0 | 0.0001 |
| 8. Muscle strength | > 50 = 1 < 55 = 0 | 0.0003 |
| 9. Cough (Norris) | Normal = 1 Abnormal/absent = 0 | 0.0028 |
| 10. Swallowing (Norris) | Normal = 3 Soft food = 2 Mixed food = 1 Semi-liquid food = 0 | 0.0059 |
| 11. Slow vital capacity | > 80% = 1 < 80% = 0 | 0.0003 |

- Model by Meininger et al (2005) identified 11 risk factors strongly predictive of survival
- Proposed three risk factors—atrophy, spasticity, and fasciculations— indicated spatial diffusion
- The risk of death increased with the number of regions with lower motor neuron involvement but decreased when upper motor neuron involvement increased
- Model by Katz et al (2010) found that isolated gross motor impairment predicts the longest time to respiratory and bulbar involvement

*Amyotrophic Lateral Sclerosis. 2005; 6: 37-44*

Figure 25

Characterizing the EEC definite phenotype in EMPOWER

Figure 28

EMPOWER baseline demographics

EEC definite subjects were significantly more female, significantly younger, and had non-significantly reduced BMIs than EEC non-definite subjects

| Baseline | Non-definite | Definite | % diff | p = |
|---|---|---|---|---|
| Age (years) | 57.659 | 55.789 | -3.2% | 0.0175 |
| Female | 33.3% | 40.9% | 22.8% | 0.0243 |
| Female BMI (kg/m**2) | 25.686 | 25.6 | -0.3% | 0.8769 |
| Male BMI (kg/m**2) | 26.488 | 25.972 | -1.9% | 0.1553 |

Figure 29

EMPOWER site of onset and riluzole use

The EEC definite group was characterized by a non-significant increase in bulbar-onset disease and riluzole use

| Baseline | Non-definite | Definite | % diff | p= |
|---|---|---|---|---|
| Riluzole use | 74.8% | 76.2% | 1.9% | 0.6862 |
| Bulbar onset | 22.1% | 25.7% | 16.3% | 0.2164 |

Figure 31

EMPOWER baseline cardiac characteristics

EEC definite subjects had significantly elevated pulse and diastolic BP

| Baseline | Non-definite | Definite | % diff | p= |
|---|---|---|---|---|
| Pulse rate (bpm) | 74.014 | 75.865 | 2.5% | 0.0290 |
| Diastolic BP (mmHg) | 79.419 | 82.238 | 3.5% | <0.0001 |
| Systolic BP (mmHg) | 127.67 | 129.399 | 1.4% | 0.1097 |

Figure 35

EMPOWER baseline laboratory characteristics

EEC definite subjects had highly significant decrease in baseline creatinine

| Baseline | Non-definite | Definite | % diff | p |
|---|---|---|---|---|
| Creatinine (umol/L) | 71.321 | 68.429 | -4.1% | 0.0096 |
| Phosphorous (mmol/L) | 1.190 | 1.214 | 2.0% | 0.0359 |
| GFR (mL/min/1.73m^2) | 95.284 | 98.961 | 3.9% | 0.0425 |
| Platelet count (x10^9 cells/L) | 250.335 | 258.867 | 3.4% | 0.0489 |
| Cholesterol (mmol/L) | 5.624 | 5.492 | -2.3% | 0.0796 |
| Lactate dehydrogenase (U/L) | 187.260 | 182.427 | -2.6% | 0.0797 |
| Creatine phoshokinase (U/L) | 297.736 | 266.472 | -10.5% | 0.0981 |
| Bicarbonate (mmol/L) | 23.579 | 23.299 | -1.2% | 0.1150 |
| Triglycerides (mmol/L) | 1.960 | 1.883 | -3.9% | 0.3620 |
| Uric acid (umol/L) | 310.748 | 302.167 | -2.8% | 0.3620 |
| Gamma glutmyltransferase (U/L) | 31.219 | 29.620 | -5.1% | 0.4001 |
| Total bilirubin (umol/L) | 9.625 | 9.817 | 2.0% | 0.5989 |
| Urine pH | 5.792 | 5.807 | 0.3% | 0.6851 |

Figure 36

Treatment effects in EEC definite subjects

COMPOSITIONS AND METHODS FOR TREATING AMYOTROPHIC LATERAL SCLEROSIS IN RESPONDERS

CROSS REFERENCE

This application is a continuation application of U.S. Application No. 15/492,832 filed Apr. 20, 2017, now U.S. Patent No. 9,956,206, issued May 1, 2018, which is a continuation application of U.S. Application No. 14/194,558 filed Feb. 28, 2014, now U.S. Patent No. 9,662,313, issued May 30, 2017, which claims the benefit of U.S. Provisional Application No. 61/771,032filed Feb.28, 2013, U.S. Provisional Application No. 61/772,328 filed Mar. 4, 2013, U.S. Provisional Application No. 61/786,236 filed Mar. 14, 2013, and U.S. Provisional Application No. 61/911,984 filed Dec. 4, 2013, each of which are hereby incorporated herein by reference in their entirety.

GOVERNMENT INTERESTS

Not Applicable.

PARTIES TO A JOINT RESEARCH AGREEMENT

Not Applicable.

INCORPORATION BY REFERENCE OF MATERIAL SUBMITTED ON A CD

Not Applicable.

BACKGROUND

Not Applicable.

SUMMARY OF THE INVENTION

Embodiments of the invention are directed to a method for treating amyotrophic lateral sclerosis in a subject in need thereof comprising: administering to the subject a therapeutically effective amount of (6R)-2-amino-4,5,6,7-tetrahydro-6-(propylamino)benzothiazole or a pharmaceutically acceptable salt thereof, wherein the subject is a subject with definite ALS, amyotrophic lateral sclerosis symptom onset duration of less than about 18 months, and concomitant riluzole administration and wherein the amyotrophic lateral sclerosis is treated.

In some embodiments, definite ALS is defined by the El Escorial diagnosis criteria. In some embodiments, The method of claim 2, wherein the subject is a subject with a creatine value of greater than 72.0 μmol/L. In some embodiments, said subject with concomitant riluzole administration is a subject who has been receiving riluzole for more than about thirty days. In some embodiments, the subject is a subject with a pulse rate of greater than 81.0 beats per minute, a cholesterol value of less than or equal to 5.3 mmol/L, a creatine phosphokinase value of less than or equal to 184.0 U/L, a bicarbonate value of less than or equal to 21.6 mmol/L, or any combination thereof. In some embodiments, said subject with amyotrophic lateral sclerosis symptom onset duration of less than about 18 months is a subject with symptom onset selected from about 18 months, about 17 months, about 16 months, about 15 months about 14 months, about 13 months, about 12 months, about 11 months, about 10 months, about 9 months, about 8 months, about 7 months, about 6 months, about 5 months, about 4 months, about 3 months, about 2 months, and about 1 month.

In some embodiments, the therapeutically effective amount of (6R)-2-amino-4,5,6,7-tetrahydro-6-(propylamino)benzothiazole or a pharmaceutically acceptable salt thereof is from 150 milligrams to 3,000 milligrams per day. In some embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In some embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In some embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In some embodiments, the therapeutically effective amount of (6R)-2-amino-4,5,6,7-tetrahydro-6-(propylamino)benzothiazole or a pharmaceutically acceptable salt thereof is 150 milligrams twice daily. In some embodiments, the therapeutically effective amount of (6R)-2-amino-4,5,6,7-tetrahydro-6-(propylamino)benzothiazole or a pharmaceutically acceptable salt thereof is from 300 milligrams twice daily.

In some embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient. In some embodiments, said pharmaceutical composition is chirally pure for (6R)-2-amino-4,5,6,7-tetrahydro-6-(propylamino)benzothiazole or a pharmaceutically acceptable salt thereof. In some embodiments, the chiral purity for (6R)-2-amino-4,5,6,7-tetrahydro-6-(propylamino)benzothiazole or a pharmaceutically acceptable salt thereof is about 99% or more. In some embodiments, said pharmaceutical composition is selected from a tablet, a capsule and a liquid. In some embodiments, said (6R)-2-amino-4,5,6,7-tetrahydro-6-(propylamino)benzothiazole or a pharmaceutically acceptable salt thereof is administered orally.

In some embodiments, said subject is diagnosed with one of the following diseases: definite amyotrophic lateral sclerosis, probable amyotrophic lateral sclerosis, possible amyotrophic lateral sclerosis and suspected amyotrophic lateral sclerosis. In some embodiments, treating amyotrophic lateral sclerosis in said subject is selected from improved ALSFRS-R score, improved CAFS rank, decreased mortality, increased life expectancy, and combinations thereof.

Embodiments herein are directed to a method of treating a patient comprising: identifying said patient as a responder; and administering to said subject a therapeutically effective amount of (6R)-2-amino-4,5,6,7-tetrahydro-6-(propylamino)benzothiazole or a pharmaceutically acceptable salt thereof.

In some embodiments, the step of identifying said patient as a responder comprises diagnosing said patient with El Escorial definite ALS.

In some embodiments, the step of identifying the patient with El Escorial definite ALS as a responder further includes measuring the serum creatinine levels of the patient; and identifying the patient as a responder if the serum creatinine levels are greater than about 72 μmol/L.

In some embodiments, the step of identifying the said patient as a responder comprises identifying the presence of the presence of amyotrophic lateral sclerosis symptom onset duration of less than about 18 months, concomitant riluzole administration, a pulse rate of greater than 81.0 beats per minute, a creatinine value of greater than 72.0 µmol/L, a cholesterol value of less than or equal to 5.3 mmol/L, a creatine phosphokinase value of less than or equal to 184.0 U/L, a bicarbonate value of less than or equal to 21.6 mmol/L, or any combination thereof.

In some embodiments, the step of identifying the said patient as a responder comprises wherein the step of identifying said patient as a responder comprises diagnosing said patient with EEC definite ALS, identifying the presence of the presence of amyotrophic lateral sclerosis symptom onset duration of less than about 18 months, and concomitant riluzole administration.

In some embodiments, the step of identifying the said patient as a responder comprises wherein the step of identifying said patient as a responder comprises diagnosing said patient with EEC definite ALS, identifying the presence of the presence of amyotrophic lateral sclerosis symptom onset duration of less than about 18 months, concomitant riluzole administration, and a creatinine value of greater than 72.0 µmol/L.

DESCRIPTION OF THE DRAWINGS

FIGS. 5-23 show exemplary methods of treating amyotrophic lateral sclerosis in accordance with embodiments described herein.

FIGS. 24-49 show exemplary methods of treating amyotrophic lateral sclerosis in accordance with embodiments described herein.

Figure 50:
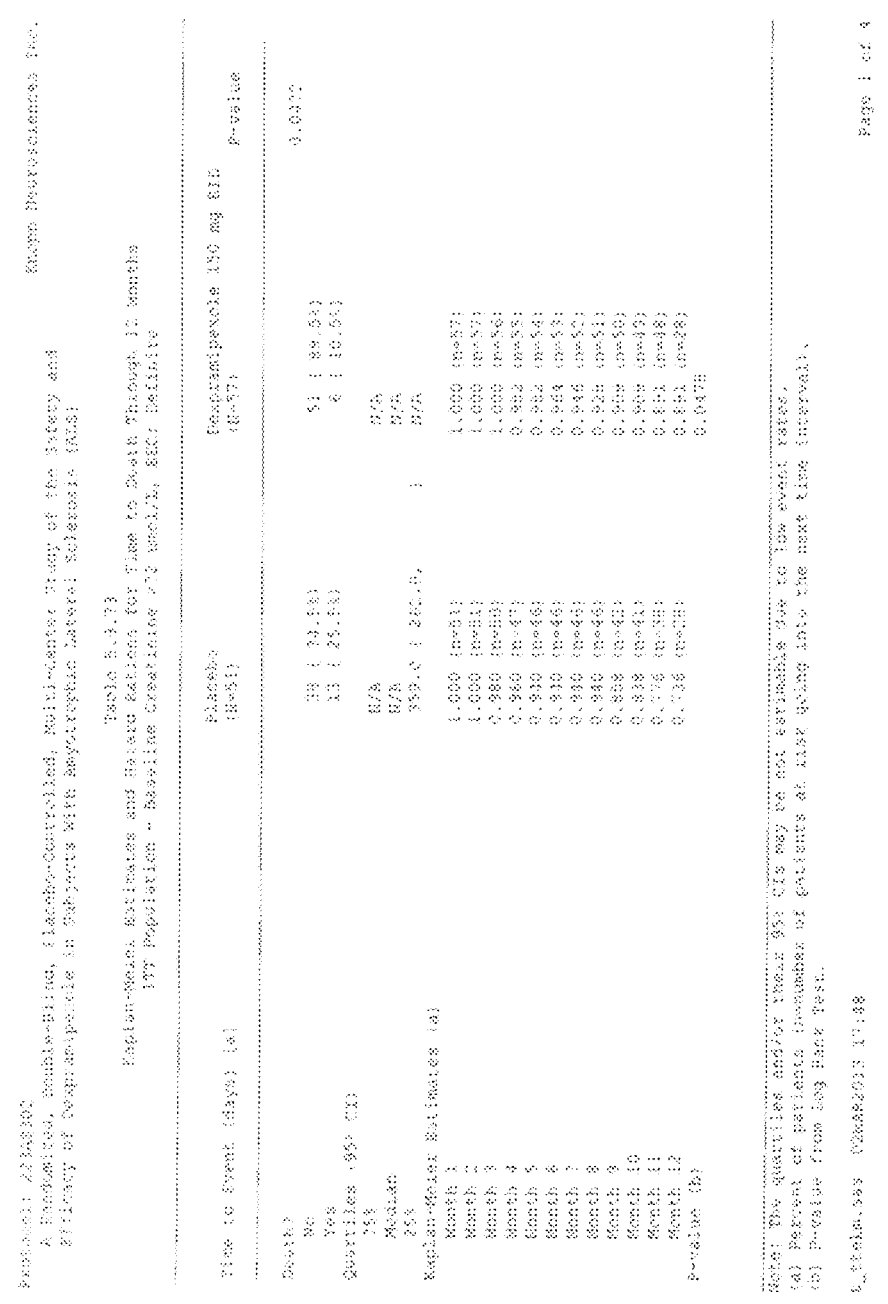
Figure 51:
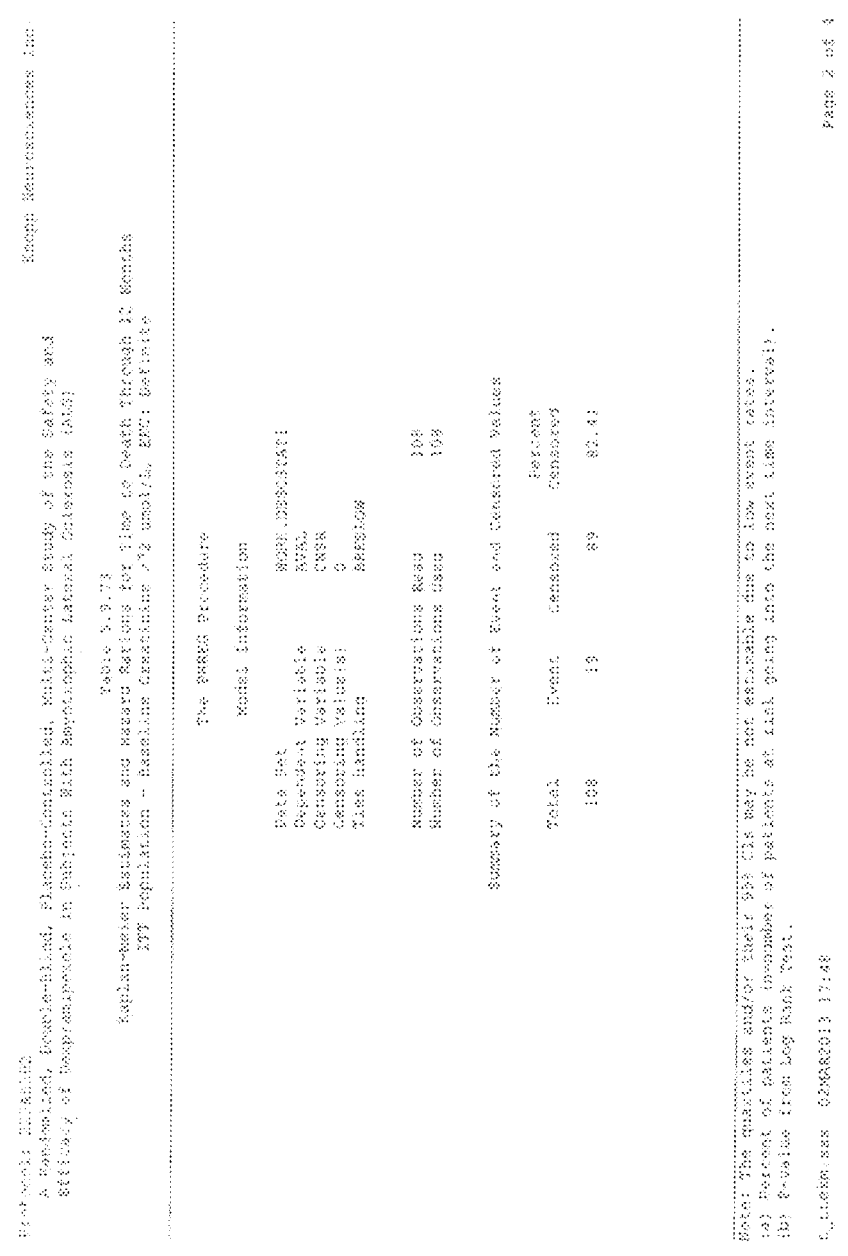
Figure 53:
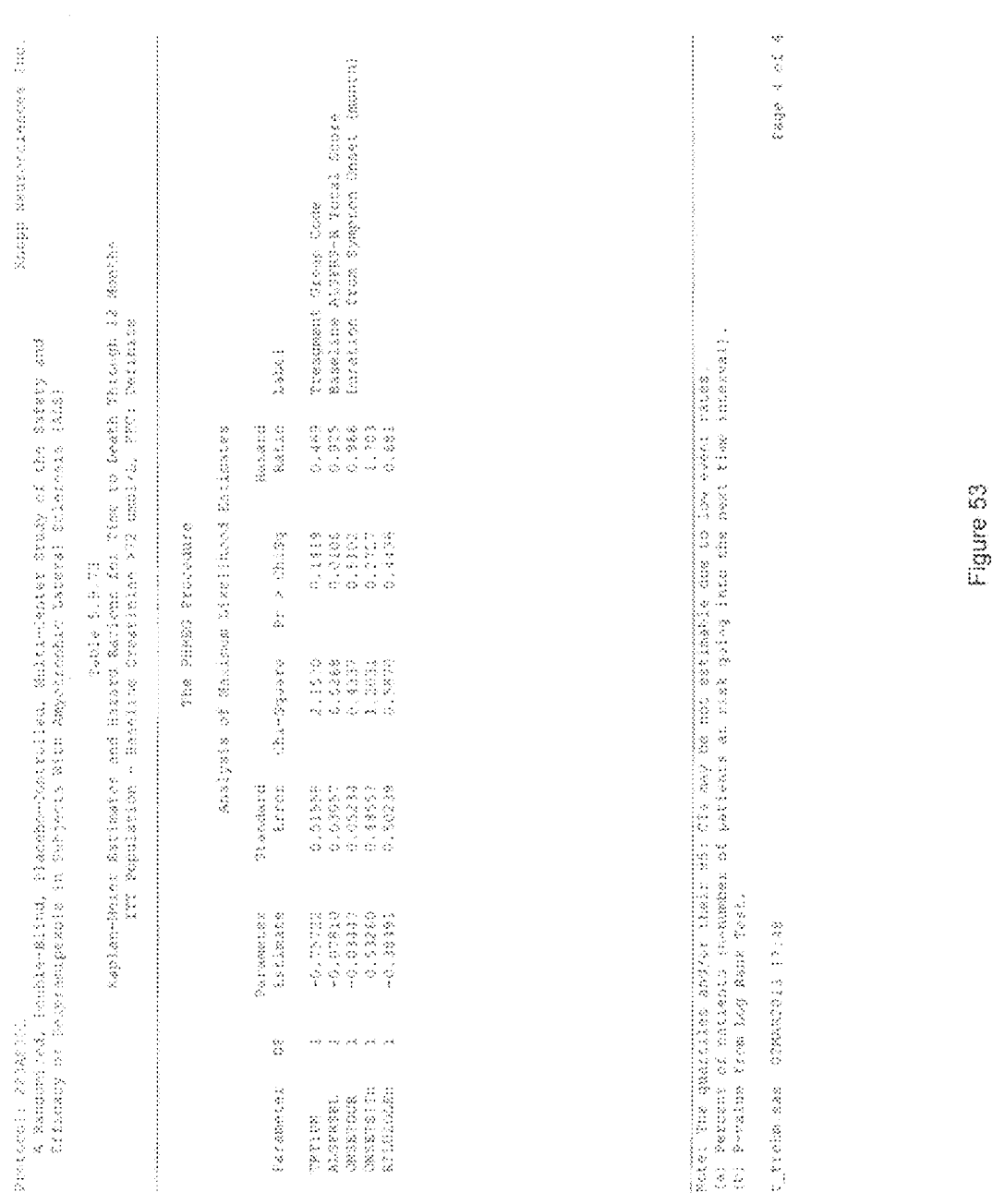

FIGS. 50-55 show data tables of the Kaplan-Meier estimates and hazard rations for time to death, slope of ALS-FRS-R total score, and summary of joint rank (CAFS) through twelve months for subjects with a baseline creatinine of greater than about 72 µmol/L.

FIGS. 56-67 show data tables for the change from baseline in serum creatinine results by treatment group.

DETAILED DESCRIPTION

Figure 1:
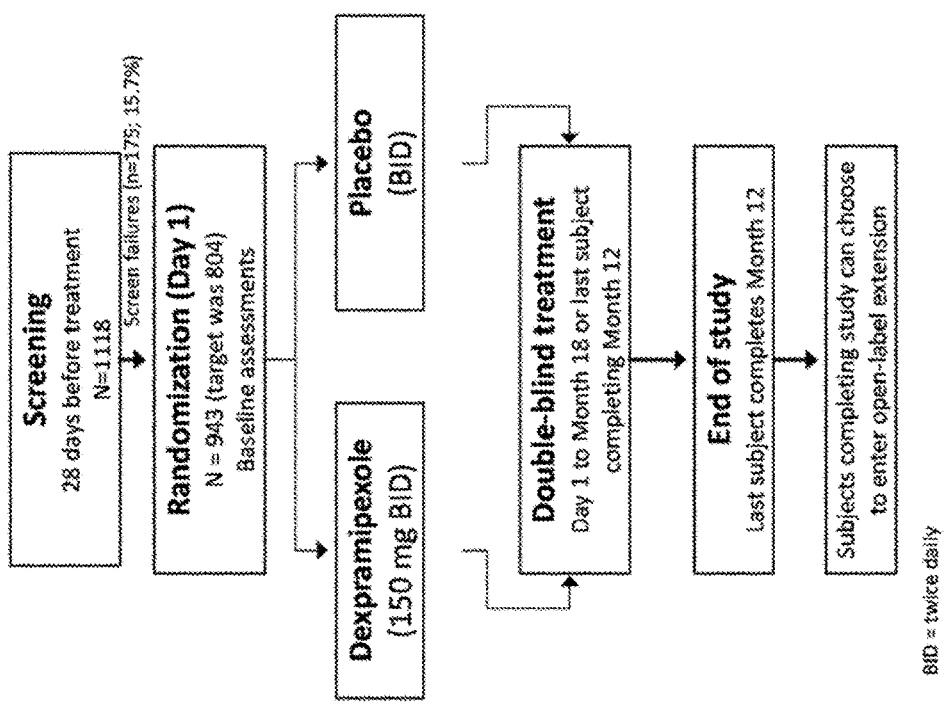
FIG. 1 depicts a flow chart of study subject disposition for a clinical trial.

Before the present compositions and methods are described, it is to be understood that any invention is not limited to the particular processes, compositions, or methodologies described, as these may vary. Moreover, the processes, compositions, and methodologies described in particular embodiments are interchangeable. Therefore, for example, a composition, dosage regimen, route of administration, and so on described in a particular embodiment may be used in any of the methods described in other particular embodiments. It is also to be understood that the terminology used in the description is for the purpose of describing the particular versions or embodiments only, and is not intended to limit the scope of the present invention, which will be limited only by the appended claims. Unless clearly defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

It must be noted that, as used herein, and in the appended claims, the singular forms "a", "an", and "the" include plural reference unless the context clearly dictates otherwise.

Embodiments including the transition phrase "consisting of" or "consisting essentially of" include only the recited components and inactive ingredients. For example, a composition "consisting essentially of" dexpramipexole can include dexpramipexole and inactive excipients, which may or may not be recited, but may not contain any additional active agents or neuroprotectants. A composition "consisting of" dexpramipexole may include only the components specifically recited.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes both instances where the event occurs and instances where it does not.

"Administering", when used in conjunction with a therapeutic, means to administer a therapeutic directly into or onto a target tissue or to administer a therapeutic to a subject whereby the therapeutic positively impacts the tissue to which it is targeted. "Administering" a composition may be accomplished by oral administration, injection, infusion, absorption or by any method in combination with other known techniques. "Administering" may include the act of self-administration or administration by another person such as a healthcare provider or a device.

The term "improves" is used to convey that the present invention refers to the overall physical state of an individual to whom an active agent has been administered. For example, the overall physical state of an individual may "improve" if one or more symptoms of a neurodegenerative disorder are alleviated by administration of an active agent. "Improves may also refer to changes in the appearance, form, characteristics, and/or physical attributes of tissue, or any combination thereof, to which it is being provided, applied, or administered.

As used herein, the term "therapeutic" means an agent utilized to treat, combat, ameliorate, or prevent, or any combination thereof, an unwanted condition or disease of a subject.

The terms "therapeutically effective amount" or "therapeutic dose" as used herein are interchangeable and may refer to the amount of an active agent or pharmaceutical compound or composition that elicits a biological and/or medicinal response in a tissue, system, animal, individual or human that is being sought by a researcher, veterinarian, medical doctor or other clinician, or any combination thereof. A biological or medicinal response may include, for example, one or more of the following: (1) preventing a disorder, disease, or condition in an individual that may be predisposed to the disorder, disease, or condition but does not yet experience or display pathology or symptoms of the disorder, disease, or condition, (2) inhibiting a disorder, disease, or condition in an individual that is experiencing or displaying the pathology or symptoms of the disorder, disease, or condition or arresting further development of the pathology and/or symptoms of the disorder, disease, or condition, and/or (3) ameliorating a disorder, disease, or condition in an individual that is experiencing or exhibiting the pathology or symptoms of the disorder, disease, or condition or reversing the pathology and/or symptoms disorder, disease, or condition experienced or exhibited by the individual. In embodiments, a biological or medicinal response may include, for example, one or more of the following: (1) inhibiting a disorder, disease, or condition in an individual that is experiencing or displaying the pathology or symptoms of the disorder, disease, or condition or arresting further development of the pathology and/or symptoms of the disorder, disease, or condition, and/or (2) ameliorating a disorder, disease, or condition in an individual that is experiencing or exhibiting the pathology or symptoms of the disorder, disease, or condition or reversing the pathology and/or symptoms disorder, disease, or condition experienced or exhibited by the individual.

As used herein, the term "neuroprotectant" refers to any agent that may prevent, ameliorate or slow the progression of neuronal degeneration and/or neuronal cell death.

The term "treating" may be taken to mean prophylaxis of a specific disorder, disease, or condition, alleviation of the symptoms associated with a specific disorder, disease, or condition and/or prevention of the symptoms associated with a specific disorder, disease or condition. In some embodiments, the term refers to slowing the progression of the disorder, disease, or condition or alleviating the symptoms associated with the specific disorder, disease, or condition. In some embodiments, the term refers to slowing the progression of the disorder, disease, or condition. In some embodiments, the term refers to alleviating the symptoms associated with the specific disorder, disease, or condition. In some embodiments, the term refers to restoring function which was impaired or lost due to a specific disorder, disease, or condition.

The term "subject" or "patient" generally refers to any living organism to which compounds described herein are administered and may include, but is not limited to, any human, primate, or non-human mammal. A "subject" may or may not be exhibiting the signs, symptoms, or pathology of amyotrophic lateral sclerosis (ALS) at any stage of any embodiment.

As used herein, the term "naïve subject" refers to a subject that has not previously received pramipexole treatment (either (R)-pramipexole or (S)-pramipexole), particularly, (R)-pramipexole, or who has not received a titration regimen of pramipexole previous to receiving a starting dose of pramipexole.

As used herein, the terms "enantiomers", "stereoisomers", and "optical isomers" may be used interchangeably and refer to molecules which contain an asymmetric or chiral center and are mirror images of one another. Further, the terms "enantiomers", "stereoisomers", or "optical isomers" describe a molecule which, in a given configuration, cannot be superimposed on its mirror image.

As used herein, the terms "chirally pure", "optically pure", or "enantiomerically pure" may be taken to indicate that a composition contains a greatly enhanced percentage of a single optical isomer. In some embodiments, the chirally pure (6S)-dexpramipexole has 99% chiral purity or greater. In some embodiments, the chirally pure (6S)-dexpramipexole has 99.5% chiral purity or greater. In some embodiments, the chirally pure (6S)-dexpramipexole has 99.7% chiral purity or greater. In some embodiments, the chirally pure (6S)-dexpramipexole has 99.9% chiral purity or greater. In some embodiments, the chirally pure (6S)-dexpramipexole has 99.95% chiral purity or greater. In some embodiments, the chirally pure (6S)-dexpramipexole has 99.99% chiral purity or greater. Such chirally pure dexpramipexole allows for therapeutic and pharmaceutical compositions that may have a wide individual and daily dose range. As such, the various methods provide a composition including only dexpramipexole in a pharmaceutically acceptable dosage, and in some embodiments, such pharmaceutical compositions may further include a pharmaceutically acceptable carrier, excipient, and/or diluent.

The term "enantiomerically enriched" may be taken to indicate that at least 51% of a composition is a single optical isomer or enantiomer. The term "enantiomeric enrichment" as used herein refers to an increase in the amount of one enantiomer as compared to the other. A "racemic" mixture is a mixture of about equal amounts of (6R) and (6S) enantiomers of a chiral molecule.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has an efficacious outcome based upon the needs of the artisan. A pharmaceutical composition may, for example, contain dexpramipexole or a pharmaceutically acceptable salt of dexpramipexole as the active ingredient.

For the purposes of this disclosure, a "salt" is any acid addition salt, preferably a pharmaceutically acceptable acid addition salt, including but not limited to, halogenic acid salts such as hydrobromic, hydrochloric, hydrofluoric, and hydroiodic acid salts; any pharmaceutically acceptable inorganic acid salt such as, for example, nitric, perchloric, sulfuric, and phosphoric acid salts; any pharmaceutically acceptable organic acid salt such as, for example, sulfonic acid salts (methanesulfonic, trifluoromethane sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic, and maleic acid salts; and any pharmaceutically acceptable amino acid salt such as aspartic or glutamic acid salts. Further, the acid addition salt may be a mono- or di-acid addition salt, such as a di-hydrohalogenic, di-sulfuric, di-phosphoric or di-organic acid salt. In all cases, the acid addition salt is used as an achiral reagent that is not selected on the basis of any expected or known preference for interaction with or precipitation of a specific optical isomer of the products of this disclosure.

"Pharmaceutically acceptable salt" is meant to indicate those salts which are, within the scope of sound medical judgment, suitable for use in contact with the tissues of a subject without undue toxicity, irritation, allergic response, and the like, and are commensurate with a reasonable benefit/risk ratio. Pharmaceutically acceptable salts are well known in the art. For example, Berge et al. 6, J. Pharm. Sciences, 1-19 (1977), describes pharmaceutically acceptable salts in detail.

As used herein, the term "daily dose amount" refers to the amount of dexpramipexole per day that is administered and/or prescribed to a subject. This amount can be administered in multiple unit doses or in a single unit dose, and at a single time during the day or at multiple times throughout the day.

A "dose amount" or "dose" as used herein, is generally equal to the dosage of the active ingredient which may be administered per day. For example, a dose amount of dexpramipexole may be 50 milligrams, 100 milligrams, 150 milligrams, 300 milligrams, 450 milligrams, 600 milligrams, or an amount between any two of these amounts per day.

The term "unit dose" as used herein may be taken to indicate a discrete amount of the therapeutic composition that contains a predetermined amount of the active compound. The amount of the active compound is generally equal to the dosage of the active ingredient which may be administered at a single time during the day or at multiple times throughout the day. The unit dose may be a fraction of the desired daily dose which may be given in fractional increments, such as, for example, one-half or one-third the desired daily dose. For example, a 150 milligram per day dose amount of dexpramipexole may be administered as two unit doses of 75 milligrams each, three unit doses of 50 milligrams each, or four unit doses of 37.5 milligrams each.

Throughout the application, the term "dopaminergic activity equivalent" (DAE) will be referred to, which means the measure of activity at the dopamine receptors equivalent to the activity of 1 milligram of pramipexole at the dopamine receptors. For example, a dosage of dexpramipexole having a "dopaminergic activity equivalent" (DAE) of 0.01 would have activity at the dopamine receptors which is equivalent to the activity of 0.01 milligrams of pramipexole. The DAE can also be related to a variety of pharmaceutical terms, including maximum tolerated dose (MTD), no observable adverse effect level (NOAEL), and non-effective dose amount for the sake of clarity. For example, the no observable adverse effect level (NOAEL) dose amount for pramipexole is most preferably below 0.05 milligrams. This, in turn, corresponds to a DAE of below 0.05. A dose amount of dexpramipexole having a DAE of 0.01 would, therefore, be below the DAE for the most preferable pramipexole NOAEL dose amount of 0.05 milligrams. In some embodiments, DAE is determined by measuring the binding affinity ($IC_{50}$) or activity ($EC_{50}$) at the $D_2$ and/or $D_3$ receptors relative to the same parameter for 1 milligrams of pramipexole.

The degree to which dosing of a molecule has demonstrable phenotypic activity resulting from affinity to particular receptors or other pharmaco-effective proteins, even when the activity results from affinities to unknown targets, can be operationally defined in terms of whether this activity contributes in a positive way ("on-target" activity) or a negative way ("off-target" activity) to a specific and desired therapeutic effect. For any given molecule, a number of "off-target" activities can theoretically be identified, but "on-target" activity is restricted to the desired therapeutic effect. To the extent that these activities can be measured and quantified, or comparisons be made with known standards, an index of activity can be generated for each of these categories (the "activity equivalent", or "AE"), and one or more ratios generated to compare "off-target" to "on-target" activities, useful to compare potential risk-benefit ratios between molecules.

Unless specifically indicated otherwise, reference to "EMPOWER", including in the Figures, shall mean Study 223AS302, which is a randomized, placebo-controlled study in which subjects with ALS have been randomized in a 1:1 ratio to placebo or dexpramipexole 150 mg every 12 hours. Subjects with possible, probable, probable laboratory-supported, or definite ALS as defined by the El Escorial criteria who had ALS symptoms for ≤24 months at the time of entry into the study and a slow vital capacity of ≥65% of predicted were eligible to participate in this study. This study is described in more detail in the Examples.

Unless specifically indicated otherwise, reference to "dex", including in the Figures, shall mean dexpramipexole, including (6R)-2-amino-4,5,6,7-tetrahydro-6-(propylamino)-benzothiazole and any pharmaceutically acceptable salt thereof, particularly (6R)-2-amino-4,5,6,7-tetrahydro-6-(propylamino)-benzothiazole dihydrochloride monohydrate.

Unless specifically indicated otherwise, reference to "CL201", including in the Figures, shall mean a 2-part, double-blind, randomized study of the safety, tolerability, and clinical effects of dexpramipexole in subjects with ALS. In Study CL201 Part 1, subjects with ALS received daily doses of either placebo (27 subjects) or dexpramipexole (75 subjects: 23 subjects, 50 mg per day; 26 subjects, 150 mg per day, or 26 subjects, 300 mg per day) for up to 12 weeks. In Part 2, 97 subjects continued on to the 4-week placebo washout phase; 92 subjects were subsequently re-randomized to double-blind active treatment with 50 mg per day or 300 mg per day dexpramipexole for at least 24 weeks. According to the protocol for Part 2, subjects were to receive 2 dosage levels of dexpramipexole for up to 76 weeks (4 weeks of placebo washout followed by up to 72 weeks of active, double-blind treatment). However, Part 1 results were analyzed and, subsequently, an administrative decision was made to close Study CL201 after all active subjects completed their Part 2 Week 28 visit. Therefore, once the last subject had completed at least 24 weeks of double-blind active treatment in Study CL201 Part 2 (Week 28), all active subjects were offered the opportunity to continue receiving open-label treatment with 300 mg per day dexpramipexole in the safety extension study, CL211. The administrative closure of the study created significant artificial attrition at study visits beyond Week 28, with a corresponding increase in missing safety and efficacy data. Therefore, the Part 2, Week 28 visit was pre-specified as the primary time-point for all Part 2 data analyses.

Unless specifically indicated otherwise, reference to "CAFS", including in the Figures, shall mean Combined Assessment of Function and Survival.

Unless specifically indicated otherwise, reference to "El Escorial" or "EEC", including in the Figures, shall mean the El Escorial World Federation of Neurology Criteria for the Diagnosis of ALS, as further described herein.

Unless specifically indicated otherwise, reference to "El Escorial (definite)", including in the Figures, shall mean a diagnosis of definite ALS in accordance with the El Escorial World Federation of Neurology Criteria for the Diagnosis of ALS, as further described herein.

Unless specifically indicated otherwise, reference to "riluzole (yes)", including in the Figures, shall mean a subject is also taking (i.e., administering) riluzole.

Unless specifically indicated otherwise, reference to "symptom duration", including in the Figures, shall mean the time from the onset of an amyotrophic lateral sclerosis symptom(s) in a subject or observed in a subject.

Unless specifically indicated otherwise, reference to "ALSFRS-R", including in the Figures, shall mean ALS Functional Rating Scale, Revised.

Amyotrophic lateral sclerosis (ALS; Lou Gehrig's disease) is a progressively debilitating motor neuron disease, characterized by degeneration and dysfunction/death of upper and lower motor neurons. ALS is universally fatal but the rate of disease progression may not be linear. Many pathogenic mechanisms of ALS have been implicated and mitochondrial dysfunction likely plays a central role. There is currently no cure for ALS or treatments that attenuate functional decline.

Since 1994, multiple compounds have been evaluated as potential treatments to modify disease progression for ALS in randomized controlled trials with positive Phase III results only demonstrated with riluzole. However, riluzole has modest effects on survival and no demonstrated effect on muscle strength or functional decline.

Dexpramipexole is currently being evaluated for the treatment of ALS. While not wishing to be bound by theory, dexpramipexole is thought to work by increasing the bioenergetic efficiency of dysfunctional mitochondria. Dexpramipexole has shown efficacy in vitro and in vivo neurodegenerative disease models.

Dexpramipexole ((6R)-2-amino-4,5,6,7-tetrahydro-6-(propylamino)-benzothiazole) is a synthetic aminobenzothiazole derivative. The (6S) enantiomer of dexpramipexole, commonly known as "pramipexole" and commercially available under the Mirapex® name (Mirapex® is a registered trademark), is a potent dopamine agonist, which mimics the effects of the neurotransmitter dopamine. Throughout this disclosure, the word "pramipexole" will refer to (6S) enantiomer of 2-amino-4,5,6,7-tetrahydro-6-(propylamino) benzothiazole unless otherwise specified. Pramipexole has also been shown to have both neuroprotective and dopaminergic activities. Therefore, pramipexole may have utility as an inhibitor of the cell death cascades and loss of cell viability observed in neurodegenerative diseases such as Parkinson's disease. Additionally, oxidative stress caused by an increase in oxygen and other free radicals has been associated with the fatal neurodegenerative disorder amyotrophic lateral sclerosis (ALS), a progressive neurodegenerative disorder involving the motor neurons of the cortex, brain stem, and spinal cord.

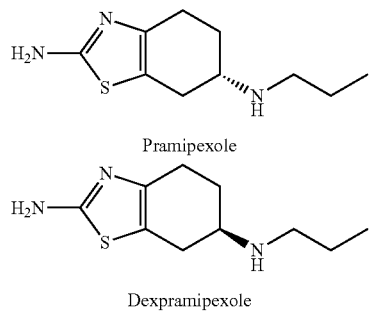

The neuroprotectant activity of both enantiomers may to require therapeutic doses in the range of about 10 milligrams per day to about 1,500 milligrams per day. Despite this, pramipexole's dosage is limited to a range between 0.5 and 4.5 milligrams per day. Moreover, even at these low doses, significant adverse side effects have been reported. For example, the Boehringer Ingelheim product insert for Mirapex® sets the maximally tolerated dose for humans at 4.5 milligrams per day. Further, a dose of pramipexole as low as 1.5 milligrams has been shown to cause somnolence in humans. Single dose toxicity of pramipexole after oral administration has been studied in rodents, dogs, monkeys and humans. In rodents, death occurred at doses of 70-105 milligrams per kilogram and above, which is equivalent to a human dose of 7-12 milligrams per kilogram or approximately 500-850 milligrams for a 70 kilogram (approximately 150 pounds) individual. In dogs, vomiting occurred at 0.0007 milligrams per kilogram and above, while monkeys displayed major excitation at 3.5 milligrams per kilogram. In human subjects, an initial single dose of pramipexole of greater than 0.20 milligrams was not tolerated. All species showed signs of toxicity related to exaggerated pharmacodynamic responses to the dopaminergic agonism of pramipexole.

Adverse side-effects associated with low dose pramipexole treatment (less than 5 milligrams per day) include, but are not limited to, dizziness, hallucination, nausea, hypotension, somnolence, constipation, headache, tremor, back pain, postural hypotension, hypertonia, depression, abdominal pain, anxiety, dyspepsia, flatulence, diarrhea, rash, ataxia, dry mouth, extrapyramidal syndrome, leg cramps, twitching, pharyngitis, sinusitis, sweating, rhinitis, urinary tract infection, vasodilatation, flu syndrome, increased saliva, tooth disease, dyspnea, increased cough, gait abnormalities, urinary frequency, vomiting, allergic reaction, hypertension, pruritus, hypokinesia, nervousness, dream abnormalities, chest pain, neck pain, paresthesia, tachycardia, vertigo, voice alteration, conjunctivitis, paralysis, tinnitus, lacrimation, mydriasis and diplopia.

Thus, clinical use of pramipexole as a mitochondria-targeted neuroprotectant is unlikely, as the high dosage needed for the neuroprotective or anti-oxidative/mitochondrial normalization action are not accessible due to high dopamine receptor affinity associated with the (6S) enantiomer. In contrast, (6R)-2-amino-4,5,6,7-tetrahydro-6-(propylamino)benzothiazole ("dexpramipexole") is an effective mitochondria-targeted agent; when administered, dexpramipexole exhibits excellent neuroprotective properties without adverse side effects. Additionally, the functional affinity difference between pramipexole and dexpramipexole (e.g. 10,000-20,000 folds) for dopamine receptors is much greater than previously reported. Thus, higher doses of dexpramipexole can be tolerated by a subject, and will allow for greater brain, spinal cord and mitochondrial concentrations, ultimately increasing the degree to which oxidative stress and/or mitochondrial dysfunction may be reduced. The neuroprotective effect of dexpramipexole may occur by at least one of three mechanisms. First, dexpramipexole may be capable of reducing the formation of reactive oxygen species in cells with impaired mitochondrial energy production. Second, dexpramipexole may partially restore the reduced mitochondrial membrane potential that is correlated with Alzheimer's, Parkinson's, Huntington's, and amyotrophic lateral sclerosis (ALS) diseases. Third, dexpramipexole may block or attenuate the apoptotic cell death pathways that are produced by pharmacological models of Alzheimer's disease, Parkinson's disease, Huntington's disease, amyotrophic lateral sclerosis diseases (ALS), and mitochondrial impairment. The high doses of dexpramipexole required to elicit these neuroprotective effects generally require highly pure preparations of dexpramipexole which take into account the biologically tolerable upper limit of (6S) enantiomer contamination (0.5 milligrams to 4.5 milligrams).

In accordance with embodiments described herein, the El Escorial World Federation of Neurology's Criteria for the Diagnosis of ALS is as follows (See also Brooks, B. R., R. G. Miller, et al. (2000). "El Escorial revisited: revised criteria for the diagnosis of amyotrophic lateral sclerosis." *Amyotroph Lateral Scler Other Motor Neuron Disord* 1(5): 293-9, which is incorporated by reference in its entirety).

The diagnoses of ALS requires the presence of: 1.) Signs of lower motor neuron (LMN) degeneration by clinical, electrophysiological or neuropathologic examination, 2.) Signs of upper motor neuron (UMN) degeneration by clinical examination, and 3.) Progressive spread of signs within a region or to other regions, together with the absence of:

Electrophysiological evidence of other disease processes that might explain the signs of LMN and/or UMN degenerations; and Neuroimaging evidence of other disease processes that might explain the observed clinical and electrophysiological signs.

Furthermore, the El Escorial World Federation of Neurology's Criteria for the Diagnosis of ALS set forth the following steps in the diagnosis of Amyotrophic Lateral Sclerosis. The diagnoses of ALS is made possible by 1.) History, physical and appropriate neurological examinations to ascertain clinical finding which may suggest suspected, possible, probable or definite ALS, 2.) Electrophysiological examinations to ascertain findings which confirm LMN degeneration in clinically involved regions, identify LMN degeneration in clinically uninvolved regions and exclude other disorders, 3.) Neuroimaging examinations to ascertain findings which may exclude other disease processes, 4.) Clinical laboratory examinations, determined by clinical judgment, to ascertain possible ALS-related syndromes, 5.) Neuropathologic examinations, where appropriate, to ascertain findings which may confirm or exclude sporadic ALS, coexistent sporadic ALS, ALS-related syndromes or ALS variants, 6.) Repetition of clinical and electrophysiological examinations at least six months apart to ascertain evidence of progression.

Clinical Features in the Diagnosis of ALS

Patients with signs of LMN degeneration (weakness, atrophy and clinical fasciculation's) and UMN degeneration (spasticity, pathologic reflexes, etc.) may be suspected as having ALS. Careful history, physical and neurological examination must search for further clinical evidence of LMN and UMN signs in four regions of the central nervous system.

Clinical features required for the diagnosis of ALS: 1.) Signs of LMN degeneration (weakness, wasting and fasciculation) in one or more of the four regions (bulbar, cervical, thoracic, lumbosacral). LMN findings in a region are without regard to right or left, but are indicative of the level of neuraxis involved. Therefore, spread of weakness, wasting and fasciculation's to another region is more important than spread from right to left or vice-versa. 2.) Signs of UMN degeneration (increased or donic tendon reflexes, spasticity, pseudo bulbar features, Hoffmann reflex and extensor plantar response) in one or more of the four regions. These UMN signs are clinically appreciated best in the bulbar, cervical and lumbosacral regions. UMN findings in a region are also without regard to right or left. Once the physical and neurological examinations provide information on the presence or absence of LMN and UMN signs in the four regions (bulbar, cervical, thoracic, lumbosacral) they must be ordered topographically in the manner to determine the certainty of the diagnosis of ALS. 3.) The topographical location of certain UMN and LMN signs in four regions of the CNS together with progression of these signs determines the certainty of the diagnoses of ALS. Progression is a cardinal feature of the clinical diagnosis of ALS. Progression of signs within a region and progression of signs to involve other regions are crucial to the diagnosis.

Clinical examinations should be repeated at least every six (6) months to assess progression.

Cases which meet the topographical criteria for probable or definite ALS but which lack progression during the twelve (12) month period diagnosis should be designated as possible ALS.

Definite ALS is defined on clinical grounds alone by the presence of UMN as well as LMN signs in the bulbar region and at least two of the other spinal regions or the presence of UMN and LMN signs in three spinal regions. The important determinants of diagnosis of definite ALS in the absence of electrophysiological, neuroimaging and laboratory examinations are the presence of UMN and LMN signs together in multiple regions.

Probable ALS is defined on clinical grounds alone by UMN and LMN signs in at least two regions. While the regions may be different, some UMN signs must be rostral (above) the LMN signs. Multiple different combinations of UMN and LMN signs may be present in patients with probable ALS.

Possible ALS is defined on clinical grounds alone when the UMN and LMN signs are in only one region or UMN signs alone are present in 2 or more regions or LMN signs are rostral to UMN signs (the latter distribution of signs needs to be differentiated from multiple non-ALS processes). Monomelic ALS, progressive bulbar palsy without spinal UMN and/or LMN signs and progressive primary lateral sclerosis without spinal LMN signs and progressive primary lateral sclerosis without spinal LMN signs constitute special cases which may develop LMN or UMN signs to meet the criteria for probable ALS with time or be subsequently confirmed at autopsy by specific LMN and UMN neuropathologic findings.

Suspected ALS will manifest only LMN signs in 2 or more regions, although UMN pathology might be demonstrated at autopsy. However, only clinical signs are considered pertinent to this classification at the time of diagnostic evaluation.

Supportive Clinical Features

Clinical features that support the diagnosis of ALS include one or more of the following: 1.) abnormal pulmonary function test not explained by other causes, 2.) abnormal speech studies not explained by other causes, 3.) abnormal swallowing studies not explained by other causes, 4.) abnormal larynx function studies not explained by other causes, 5.) abnormal isokinetic or isometric strength test in clinically uninvolved muscles, 6.) abnormal muscle biopsy with evidence of denervation.

Inconsistent Clinical Features

Clinical findings inconsistent with the diagnoses of ALS include one or more of the following not explained by physiological changes associated with aging or other disease processes: 1.) sensory dysfunction, 2.) sphincter abnormalities, 3.) autonomic nervous system dysfunction, 4.) anterior visual pathway abnormalities, 5.) movement abnormalities associated with probable Parkinson's disease defined by DATATOP criteria, 6.) cognitive abnormalities associated with clinical Alzheimer's disease as defined by NINCDS-ADRDA criteria.

If these clinical findings occur, then close attention should be paid to the possible diagnosis of other disease processes.

Lower motor neuron and upper motor neuron signs may occur together with other clinical signs in disease where the pathologic process is not primary motor neuron degeneration.

Types of ALS

The clinical signs of progressive LMN and UMN degeneration seen in ALS may a.) occur alone (sporadic ALS), b.) be present incidentally with other pre-existing disease processes that have not developed in parallel with the ALS (coexistent sporadic ALS), c.) Occur in association with laboratory-defined or epidemiologically defined abnormalities that are time-linked to the ALS (ALS-related syndromes), or d.) Occur in association with clinical, genetic or epidemiological features which develop in parallel with the ALS (ALS variants).

The physical and neurological examinations will allow for the clinical diagnosis of ALS to a particular degree of certainty as defined above; however, the history of the disease onset, toxic exposures, past medical history, injuries, family history, geographic location, etc., must be incorporated with the clinical examinations in determining whether the patient may have an ALS related syndrome or an ALS variant.

ALS-related syndromes must meet the clinical, electrophysiological and neuroimaging criteria for possible, probable or definite ALS. ALS-related syndromes have unique laboratory-defined or epidemiologically defined features which are time-linked to the development of the ALS phenotype. If correction of the associated laboratory-defined feature does not result in correction of the ALS phenotype, then the patient with an ALS-related syndrome should be considered in the same way as a patient with sporadic ALS.

ALS-related syndromes include: 1.) Monoclonal gammopathy (monoclonal gammopathy of unknown significance, Waldenstroms's macroglobulinemia, osteosclerotic myeloma, etc.), 2.) Dysimmune motor system degeneration (autoimmune; high-titer GMI ganglioside antibody; etc.), 3.) Nonmalignant endocrine abnormalities (hyperthyroidism, hyperparathyroidism, hypogonadism, etc.), 4.) Lymphoma (Hodgkin's and non-Hodgkin's lymphoma). Cases of sporadic ALS associated with insulinoma, lung, colon or thyroid cancer are thought not to be casually related, 5.) Infection (HIV-1, HTLV-I, encephalitis lethargica, varicella-zoster, brucellosis, cat-scratch disease, Creutzfeldt-Jakob disease, syphilis, delayed post-poliomyelitis, etc.), 6.) Acquired enzyme defects (detoxification enzymes, etc.), 7.) Exogenous toxins (lead, mercury, arsenic, thallium, cadmium, manganese, aluminum, organic pesticides, lupin seeds, etc.), 8.) Physical injury (electric shock, radiation therapy, etc.), 9.) Vascular (vasculitis; ischemic (Dejerine anterior bulbar artery syndrome, etc.), 10.) Spondylotic myelopathy (painless myelopathy with no sensory signs, stabilization or progression post-surgery).

ALS Variants must meet the clinical, electrophysiological and neuroimaging criteria for possible, probable or definite ALS. The predominant presentation is that seen in sporadic ALS, but includes one or more features such as: Familial pattern of inheritance (multiple phenol-types characterized by age of onset; site of onset; length of survival; and presumed type of inheritance.)

Familial ALS variants in genetic linkage studies should be characterized by an established genetic mode of inheritance over at least two generations and at least one clinically definite or autopsy confirmed case and compelling evidence excluding other possible causes. Affected sub pairs occurring in one generation alone may not result from a single gene effect.

Examples: a.) ALS with defined inheritance and known gene product (hexosaminidase A/B deficiency, superoxide dismutase deficiency); b.) ALS with defined inheritance and chromosome linkage but no gene product (chromosome 21 associated familial ALS or chromosome 2 associated juvenile familial ALS); c.) ALS with defined inheritance and no known linkage or gene product (most cases or familial ALS); d.) Geographic clustering (including disorders seen in the Western Pacific, Guam, Kii Peninsula, North Africa, Madras, etc.); e.) Extrapyramidal signs (bradykinesia; cogwheel rigidity; tremor; clinically significant onset of supranuclear eye signs (pursuit abnormalities); familial or sporadic); f.) Cerebellar degeneration (spinocerebellar abnormalities; familial or sporadic); g.) Dementia (progressive cognitive abnormalities; familial or sporadic); h.) Autonomic nervous system involvement (clinically significant abnormal cardiovascular reflexes; bowel or bladder control problems; familial or sporadic); i.) Objective sensory abnormalities (decreased vibration; sharp-dull discrimination; blunting of cold sensation; familial or sporadic); j.) Electrophysiological features in the diagnoses of ALS Patients with suspected, possible, probable or definite ALS on clinical grounds should have electrophysiological studies performed to confirm LMN degeneration in clinically affected regions, find electrophysiological evidence of LMN degeneration in clinically uninvolved regions and to exclude other pathophysiological processes.

ALS may be most reliably identified when the clinical and electrophysiological findings are widespread, involving a sufficient number of regions so that other possible cause of similar EMG abnormalities are highly unlikely. The confirmation of the diagnosis of ALS depends on finding electrophysiological evidence of LMN degeneration in at least two muscles of different root or spinal nerves and different cranial or peripheral nerve innervation in two or more of the four (bulbar, cervical, thoracic, lumbosacral) regions. The features of LMN degeneration in a particular muscle are defined by electromyographic needle examination and nerve conduction studies using standard methods for each measure.

Electrophysiological features required to identify definite primary LMN degeneration include all of the following: 1.) Reduced recruitment (reduced interference pattern with firing rates over 10 Hz), 2.) Large motor unit action potentials (large amplitude, long duration), and 3.) Fibrillation potentials.

Electrophysiological features that support the identification of possible primary LMN degeneration include one or more of the following: 1.) either reduced recruitment, large motor unit potentials, fibrillation potentials or unstable motor unit potentials alone, 2.) polyphasic motor unit potentials or increased single fiber density alone, 3.) low amplitude compound muscle actions potentials if the disease duration is over 5 years or if there is associated atrophy, 4.) low amplitude compound muscle action potentials, 5.) compound muscle action potential change between proximal and distal sites of stimulation that is uniform along the length of the nerve, 6.) up to 30% decrement in motor conduction velocity below established normal values if a low amplitude compound muscle action potential greater than 10 percent of normal is present, 7.) up to 50% decrement in motor conduction velocity below established normal values if the compound muscle action potential is below 10% or normal, 8.) up to 20% decrement of the compound muscle action potential on 2 Hz repetitive stimulation, 9.) up to 10% decrement in sensory nerve conduction velocity and action potential amplitude from established normal values, 10.) complex repetitive discharges, and 11.) absence of fasciculations.

Electrophysiological features compatible with UMN degeneration and not excluding ALS include one or more of the following: 1.) up to 30% increment in central motor conduction velocity, 2.) up to 10% decrement in somatosensory, evoked potential amplitude and up to 10% increment in somatosensory evoked potential latency, 3.) mild abnormalities of autonomic function, 4.) mild abnormalities of polysomnography, 5.) mild abnormalities of electronystagmography.

Electrophysiological features that are inconsistent with the diagnoses of ALS or suggest the presence of additional other disease processes include one or more of the following: 1.) focal reduction in compound muscle action potential or more than 10% in a 4-cm segment, 2.) motor conduction velocities, F wave latencies or H wave amplitudes which are more than 30% above established normal values, 3.) more than 20% decrement of repetitive stimulation at 2 Hz, 4.) sensory action potential latencies more than 20% above or sensory action potential amplitudes more than 20% below established normal values, 5.) unstable motor unit potentials with no other electromyographic changes, 6.) more than 30% increment of central motor conduction velocity, 7.) more than 10% increment in sensory evoked potential latency or more than 10% decrement in sensory evoked potential amplitude, 8.) moderate or greater abnormalities in autonomic function or electronystagnography.

Employing Electrophysiological Evidence of LMN Degeneration to Confirm the Diagnosis of ALS The certainty of LMN degeneration is determined by the presence of the above finding for each muscle tested in the region.

At least two muscles of different root or spinal nerve and different cranial or peripheral nerve inneveration in each region should show electrophysiological evidence of either definite, probable or possible LMN degeneration for that region to be ranked as showing definite, probable or possible LMN degeneration.

Definite LMN degeneration by EMG has the same significance as clinical LMN degeneration and can upgrade the certainty of the clinical diagnoses of ALS in the same fashion as if the clinical signs of LMN degeneration were present in that region.

Probable or possible LMN degeneration by EMG does not carry the same weight as either clinical signs of definite electrophysiological evidence of LMN degeneration in a particular region.

However, the involvement of the regions with probable electrophysiological evidence of LMN degeneration or one region with probable and one region with possible electrophysiological evidence of LMN degeneration carries the same weight as one region with definite evidence of LMN degeneration in upgrading the certainty of diagnosis of ALS.

A single region with electrophysiological evidence of probable LMN degeneration or two regions with electrophysiological evidence of possible LMN degeneration can be used to upgrade the certainty of the diagnosis of ALS from possible ALS to probable ALS but not from probable ALS to definite ALS.

Neuroimaging Features in the Diagnosis of ALS

Neuroimaging studies should be selected in order to exclude other conditions which may cause UMN and/or LMN signs that may stimulate sporadic ALS.

Neuroimaging Features Required for the Diagnosis of ALS:

There are no neuroimaging tests which confirm the diagnosis of ALS.

Neuroimaging features that support the diagnosis of ALS include one or more of the following: 1.) minimal bony abnormalities on plain x-ray of skull or spinal canal, 2.) Minimal abnormalities on head or spinal cord MRI scans without spinal cord and/or root compression, 3.) Minimal abnormalities on spinal cord myelography with post-myelography CT tomography showing no spinal cord and/or root compression.

Neuroimaging features that are inconsistent with the diagnosis of ALS include one or more of the following: 1.) significant bony abnormalities on plain x-ray of skull or spinal canal, 2.) minimal abnormalities on head or spinal cord MRI scans without spinal cord and/or root compression, 3.) minimal abnormalities on spinal cord myelography with post-myelography CT tomography showing no spinal cord and/or room compression.

Neuroimaging features that are inconsistent with the diagnosis of ALS include one or more of the following: 1.) significant bony abnormalities on plain x-rays of skull or spinal canal that might explain clinical findings, 2.) significant abnormalities of head or spinal cord MRI suggesting intraparenchymal processes, arteriovenous malformations or compression of brainstem/spinal cord and/or cranial nerve or spinal nerve roots by bony abnormalities, tumor, etc. MRI of craniocervical function if bulbar onset and/or MRI or pertinent spinal region if spinal onset, 3.) significant abnormalities of spinal cord myelography with/without CT tomography or CT tomography alone suggesting lesions as noted above, 4.) significant abnormalities on spinal cord angiography suggesting arteriovenous malformations.

Employing Neuroimaging Evidence to Confirm the Diagnosis of ALS

The absence of abnormalities in appropriately performed neuroimaging studies will raise patients with clinical and/or electrophysiological evidence of probable ALS to definite ALS.

The absence of neuroimaging abnormalities cannot raise possible ALS to probable ALS.

Clinical Laboratory Features in the Diagnosis of ALS

The diagnostic process employed to confirm the diagnosis of sporadic ALS includes repeated clinical examinations, repeated electrophysiological examinations, neuroimaging to exclude other disorders and clinical laboratory examinations or exclude other disorders or support the diagnosis of ALS related syndromes.

Clinical laboratory features required for the diagnoses of ALS: There are no clinical laboratory tests which confirm the diagnosis of ALS.

Clinical laboratory features that support the diagnosis of ALS include one or more of the following: normal complete blood count, platelet count, sedimentation rate, prothrombin time, normal electrolyte (Na+, K+, Cl, C02+, Mg2+, P04) renal (BUN, creatinine) and liver function (bilirubin, SGOT, SGPT, LDH) test, creatine kinase (CK) elevation not more than 5 times upper limit of normal, normal hexosaminidase A and B activity (if possible of deficiency indicated by suggestive family history or onset under 30 years of age), normal cerebrospinal fluid cell count, protein (not more than 65 mg/dl), absence of intrathecal immunoglobulin synthesis, oligoclonal immunoglobulins and evidence of elevated intrathecal antibodies or infectious agents (syphilis, HIV-1, HTLV-I, etc.), if indicated, normal parathyroid hormone level if calcium is borderline elevated, normal free thyroid hormone concentrations if any thyroid function abnormalities (borderline elevations in T4, T3, TSH); normal glycosylated hemoglobin, if indicated, Normal serum protein electrophoresis and serum immunoeletrophresis with immunofixation; normal urine immunoelectrophoresis with immunofixation, if indicated, Minimal abnormalities in screening test for collagen vascular diseases (anti-nuclear antibody; anti-DNA antibodies; rheumatoid factor, complement, anti-tissue specific antibodies), if indicated, Minimal elevation in screening test for anti-neural antigen (GM1, GM2, GD1b gangliosides, myelin-associated glycoprotein, acetylcholine esterase, etc.) or anti-neuromuscular antigen (acetylcholine receptor, striated muscle, etc.) antibodies, if indicated.

Clinical Laboratory Features that Support the Diagnosis of ALS Related Syndromes Abnormalities consistent with monoclonal gammopathy with/without significant elevation in monoclonal anti-neural antigen antibody; Significant elevations in polyclonal antineural antigen (Gm1, Gm2, GD1b gagnliosides, myelin-associated glycoprotein, acetylcholine esterase, etc.) antibody; Significant elevation in parathyroid hormone, thyroid hormone or other significant endocrine abnormalities; Abnormalities consistent with lymphoma (Hodgkins' or non-Hodgkin's lymphoma); Evidence of infection (HIV-1, HTLV-I, *borrelia*, syphilis, brucellosis, cat-scratch disease, varicella-zoster, influenza, Creutzfeldt-Jakob disease); Evidence of intoxication (epidemiological evidence or elevated blood, urine, tissue or cerebrospinal fluid level of lead, mercury, arsenic, cadmium, manganese, aluminum, organic pesticides, lupin seeds, etc.); Evidence of physical injury (epidemiological evidence of antecedent electrical or radiation injury or severe trauma); Evidence of vasculitis (elevated erythrocyte sedimentation rate and cerebrospinal fluid abnormalities consistent with spinal cord vasculitis, i.e., markedly elevated cerebrospinal fluid protein) or ischemic injury to spinal cord without sensory signs; Evidence of pre-existing mild or moderate spinal cord spondylotic compression, not amenable to surgical correction or not responding to surgical correction, which progressed with clinical signs consistent with at least probable ALS.

Clinical Laboratory Features Inconsistent with the Diagnosis of ALS:

There is no clinical laboratory finding which, if present with the proper clinical and electrophysiological signs of ALS and appropriate neuroimaging studies, rules out the diagnosis of ALS.

ALS-related syndromes which present with the ALS phenotype as defined have been described with laboratory abnormalities (acquired or genetic), time-linked exposure to chemical, physical or infectious agents and pre-existing structural abnormalities. The correction of laboratory abnormalities, removal of chemical or physical agents, treatment of the associated disease (infection, tumor, structural abnormality) may or may not result in correction or stabilization of the ALS phenotype in ALS-related syndromes.

If correction of the abnormality does not result in improvement, the patient will be considered to have an ALS related syndrome.

If correction of the abnormality does not result in improvement, then the patient will be considered to have an ALS related syndrome.

If correction of the abnormality does not result in improvement then the patient will be considered to have sporadic ALS for the purpose of clinical studies and the therapeutic trials.

Neuropathological Features of the Diagnosis of ALS:

The clinical diagnosis may be supported or excluded by biopsy studies in the living patient and the pathological diagnosis may be proven or excluded by autopsy examination.

Pathological Studies in the Living Patient with Sporadic ALS:

Indications of Biopsies:

Biopsies of the skeletal muscle, peripheral nerve and other tissues are not required for the diagnosis of amyotrophic lateral sclerosis, unless the clinical, electrophysiological or laboratory studies have revealed changes that are atypical for ALS. In addition, the muscle biopsy may be used to demonstrate LMN involvement in a body region that had not been shown to be involved by other techniques.

Muscle Biopsy:

Features Required for the Diagnosis:

Disseminated single angulated atrophic muscle fibers, or small or large groups of such fibers.

Features that Strongly Support the Diagnosis:

Angulated atrophic muscle fibers that are strongly positive when stained with oxidative enzyme stains and with non-specific esterase or that show immunoreactive surface staining with anti-NCAM antibodies.

Features that are compatible with, and do not exclude the diagnosis: Scattered hypertrophied muscle fibers; No more than a moderate number of target or targeted fibers; Fiber type grouping of not more than mild-to-moderate extent; The presence of a small number of necrotic muscle fibers.

Features that rule out the diagnoses or suggest the presence of additional disease: 1.) Significant infiltration with lymphocytes and other mononuclear inflammatory cells; 2.) Significant arteritis; 3.) Significant numbers of muscle fibers involved with the following structural changes: necrosis; rimmed vacuoles; nemaline bodies; central cores; accumulation of mitochondria (ragged red fibers); 4.) Large fiber type grouping; 5.) Giant axonal swellings from accumulation of masses of neurofilaments, but not of PAS positive bodies, in intramuscular nerves.

Pathological Studies at Autopsy, Other than in Cases Surviving for Prolonged Periods on Life Support Systems Gross Pathological Changes Features Required for the Diagnosis:

There are positive diagnostic features on gross pathological examination.

Features that Support the Diagnosis:

There are no positive diagnostic features on gross pathological examination.

Features that support the diagnosis: selective atrophy of the motor cortex, grayness and atrophy of the anterior spinal nerve roots compared with normal, grayness of the lateral columns of the spinal cord, atrophy of skeletal muscles.

Features that rule out the diagnosis of ALS or suggest the presence of additional disease: 1.) Plaques of multiple sclerosis; 2.) A focal cause of myelopathy.

Light Microscopic Studies

Features required for the diagnosis: 1.) Some degree of loss of both of the following neuronal systems. Large motor neurons of the anterior horns of the spinal cord and motor nuclei of the brainstem (V motor, VII motor, I and X somatic motor, and XII); and large pyramidal neurons of the motor cortex and/or large myelinated axons of the corticospinal tracts. 2.) The following cellular pathological changes in the involved neuronal regions described above; neuronal atrophy with relative increase in lipofuscin and loss of Niss1 substance. There should be evidence of different stages of the process of neuronal degeneration, including the presence of normal-appearing neurons, even in the same region. 3.) Evidence of degeneration of the corticospinal tracts and the same level.

Features that strongly support the diagnosis: 1.) Lack of pathological change in the motor neurons of cranial nerves III, IV and VI, the intermediolateral column of the spinal cord, and Onuf's nucleus. 2.) The occurrence of one or more of the following cellular pathological changes in the involved neuronal systems described above: Axonal spheroids with accumulation of masses of neurofilaments, Bunina bodies; Basophilic cytoplasmic inclusions; Non-basophilic hyaline bodies ("Lewy body-like structures") seen in H&E stained sections; Increased immunocytochemical staining for phosphorylated neurofilaments in perikarya of the motor neurons; Atrophy or loss of the arborizations of the dendrites of the motor neurons of the anterior horns of the spinal cord and brainstem motor nuclei; Wallerian degeneration in the anterior roots.

Features that are Compatible with, and do not Exclude, the Diagnoses:

Variable involvement of Clark's nucleus and the spinocerebellar tracts; posterior root ganglia, the posterior columns of the spinal cord and peripheral sensory nerves; the brainstem reticular neurons and the anterolateral columns of the spinal cord; the thalamus; subthalamic nucleus; and the subastantia nigra.

Features that rule out the diagnosis or suggest the presence of additional disease:

Major pathological involvement of other parts of the nervous system, including: cerebral cortex other than the motor cortex; basal ganglia; substantia nigra; cerebellum; cranial nerves II and VIII; dorsal root ganglia.

The following cellular pathological changes in the involved neuronal systems described above: Extensive central chromatolysis; Extensive active neuronophagia; Neurofibrillary tangles; The presence of abnormal storage material; The presence of significant spongiform change; The presence of extensive inflammatory cell infiltration.

Electron-Microscopic Studies
Features Required for the Diagnosis:
Ultrastructural Studies are not Required for the Diagnosis of ALS
Features that strongly support the diagnosis: Accumulation of interwoven bundles of 10 nm neurofilaments in axonal spheroids or motor neuron perikarya, and thicker linear structures associated with dense granules (Hirano et al. 1984 J. Neuropath. Ex. Neurol. 43:461); Bunina bodies (Hart et al. 1944 Acta Neuropath. 38:225).

Features that are Compatible with, and do not Exclude the Diagnosis:

The presence of intra-axonal polyglucosan bodies.

Features that rule out the diagnosis or suggest the presence of additional disease; 1.) The presence of significant numbers of definite viral particles. 2.) The presence of significant amounts of abnormal storage materials. 3.) Extensive vacuolation of neuronal perikarya.

Glossary of Terms

As used in the El Escorial World Federation of Neurology's Criteria for the Diagnosis of ALS, the term "definite" is intended to mean specific clinical exclusionary criteria met; no other diagnosis possible on basis of clinical distribution or laboratory findings.

As used in the El Escorial World Federation of Neurology's Criteria for the Diagnosis of ALS, the term "dementia" is intended to mean progressive deterioration of specific cognitive functions.

As used in the El Escorial World Federation of Neurology's Criteria for the Diagnosis of ALS, the term "extraphyramidal" is intended to mean clinical features localizable to basal ganglia and/or midline cerebellum.

As used in the El Escorial World Federation of Neurology's Criteria for the Diagnosis of ALS, the term "hyperreflexia" is intended to mean the spread of deep tendon reflex outside stimulated territory.

As used in the El Escorial World Federation of Neurology's Criteria for the Diagnosis of ALS, the term "minor" is intended to mean subjective and objective complaints confirmed by examination (utilization of instrumental sensory testing may increase the detection of sensory abnormalities).

As used in the El Escorial World Federation of Neurology's Criteria for the Diagnosis of ALS, the term "onset" is intended to mean time of first subjective symptom noticed by patient which later is confirmed by examination.

As used in the El Escorial World Federation of Neurology's Criteria for the Diagnosis of ALS, the term "possible" is intended to mean specific clinical and exclusionary criteria met.

As used in the El Escorial World Federation of Neurology's Criteria for the Diagnosis of ALS, the term "probable" is intended to mean specific clinical and exclusionary criteria.

As used in the El Escorial World Federation of Neurology's Criteria for the Diagnosis of ALS, the term "radicular" is intended to mean distribution conforming to particular nerve root.

As used in the El Escorial World Federation of Neurology's Criteria for the Diagnosis of ALS, the term "region" is intended to mean brainstem, cervical, thoracic or lumbosacral spinal cord level (regional involvement is defined by either right or left sided signs).

As used in the El Escorial World Federation of Neurology's Criteria for the Diagnosis of ALS, the term "required" is intended to mean necessary or sufficient.

As used in the El Escorial World Federation of Neurology's Criteria for the Diagnosis of ALS, the term "segment" is intended to mean single brainstem or spinal cord level.

As used in the El Escorial World Federation of Neurology's Criteria for the Diagnosis of ALS, the term "spread" is intended to mean involvement of new anatomic segments or regions in the central nervous system.

As used in the El Escorial World Federation of Neurology's Criteria for the Diagnosis of ALS, the term "support" is intended to mean neither necessary nor sufficient, but may suggest.

As used in the El Escorial World Federation of Neurology's Criteria for the Diagnosis of ALS, the term "systemic" is intended to mean non-central nervous system.

As used in the El Escorial World Federation of Neurology's Criteria for the Diagnosis of ALS, the term "weakness" is intended to mean decreased isometric strength. As used in the El Escorial World Federation of Neurology's Criteria for the Diagnosis of ALS, the term "worsening" is intended to mean increased weakness of muscles in previously affected segment.

The El Escorial ALS Classifications are as Follows:

Definite ALS is defined on clinical grounds alone by the presence of UMN as well as LMN signs in the bulbar region and at least two of the other spinal regions or the presence of UMN and LMN signs in three spinal regions. The important determinants of diagnosis of definite ALS in the absence of electrophysiological, neuroimaging and laboratory examinations are the presence of UMN and LMN signs together in multiple regions.

Probable ALS is defined on clinical grounds alone by UMN and LMN signs in at least two regions. While the regions may be different, some UMN signs must be rostral (above) the LMN signs. Multiple different combinations of UMN and LMN signs may be present in patients with probable ALS.

Possible ALS is defined on clinical grounds alone when the UMN and LMN signs are in only one region or UMN signs alone are present in 2 or more regions or LMN signs are rostral to UMN signs (the latter distribution of signs needs to be differentiated from multiple non-ALS processes). Monomelic ALS, progressive bulbar palsy without spinal UMN and/or LMN signs and progressive primary lateral sclerosis without spinal LMN signs and progressive primary lateral sclerosis without spinal LMN signs constitute special cases which may develop LMN or UMN signs to meet the criteria for probable ALS with time or be subsequently confirmed at autopsy by specific LMN and UMN neuropathologic findings.

Suspected ALS will manifest only LMN signs in 2 or more regions, although UMN pathology might be demonstrated at autopsy. However, only clinical signs are considered pertinent to this classification at the time of diagnostic evaluation.

Embodiments are directed to methods for treating amyotrophic lateral sclerosis in a subject in need thereof comprising administering to the subject a therapeutically effective amount of (6R)-2-amino-4,5,6,7-tetrahydro-6-(propylamino)benzothiazole or a pharmaceutically acceptable salt thereof, wherein the subject is selected from a subject with definite amyotrophic lateral sclerosis, a subject with limb-onset amyotrophic lateral sclerosis, a subject with amyotrophic lateral sclerosis symptom onset duration of less than about 18 months, a subject with a high level of serum creatinine, a subject with low bicarbonate levels, a subject with concomitant riluzole administration and combinations thereof, and wherein the amyotrophic lateral sclerosis is treated. In certain embodiments, the method further comprises monitoring said subject for any clinical features associated with amyotrophic lateral sclerosis. In certain embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

In certain embodiments, the subject with definite amyotrophic lateral sclerosis is a subject diagnosed with definite ALS as defined by the El Escorial diagnosis criteria. In certain embodiments, the subject with definite amyotrophic lateral sclerosis is a subject with upper motor neuron degeneration and lower motor neuron degeneration in the bulbar region and two other spinal regions. In certain embodiments, the subject with definite amyotrophic lateral sclerosis is a subject with upper motor neuron degeneration and lower motor neuron degeneration in three spinal regions.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

In certain embodiments, the subject with amyotrophic lateral sclerosis symptom onset duration of less than about 18 months is a subject with symptom onset selected from less than 18 months, less than about 17 months, less than about 16 months, less than about 15 months, less than about 14 months, less than about 13 months, less than about 12 months, less than about 11 months, less than about 10 months, less than about 9 months, less than about 8 months, less than about 7 months, less than about 6 months, less than about 5 months, less than about 4 months, less than about 3 months, less than about 2 months, and less than about 1 month. In certain embodiments, the subject with amyotrophic lateral sclerosis symptom onset duration of less than about 18 months is a subject with symptom onset selected from about 18 months, about 17 months, about 16 months, about 15 months about 14 months, about 13 months, about 12 months, about 11 months, about 10 months, about 9 months, about 8 months, about 7 months, about 6 months, about 5 months, about 4 months, about 3 months, about 2 months, and about 1 month.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In certain embodiments, the subject with a high level of serum creatinine is a subject with serum creatinine level selected from greater than about 40 µmol/L, greater than about 45 µmol/L, greater than about 50 µmol/L, greater than about 55 µmol/L, greater than about 60 µmol/L, greater than about 65 µmol/L, greater than about 70 µmol/L, greater than about 72 µmol/L of serum creatinine. In certain embodiments, the subject with a high level of serum creatinine is a subject with serum creatinine level selected from about 40 µmol/L, about 45 µmol/L, about 50 µmol/L, about 55 µmol/L, about 60 µmol/L, about 65 µmol/L, about 70 µmol/L, about 72 µmol/L of serum creatinine.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

In certain embodiments, the subject with concomitant riluzole administration is a subject on a stable dosing regimen of riluzole. In certain embodiments, the subject with concomitant riluzole administration is a subject receiving about 50 milligrams of riluzole twice daily. In certain embodiments, the subject with concomitant riluzole administration is a subject who has been receiving riluzole for more than about thirty days. In certain embodiments, the subject with concomitant riluzole administration is a subject who has been receiving riluzole for about sixty days or more.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

In certain embodiments, treating amyotrophic lateral sclerosis in said subject is selected from improved ALSFRS-R score, improved CAFS rank, decreased mortality, increased life expectancy, and combinations thereof.

Embodiments are directed to methods for treating amyotrophic lateral sclerosis in a subject diagnosed with definite amyotrophic lateral sclerosis comprising administering to the subject a therapeutically effective amount of (6R)-2-amino-4,5,6,7-tetrahydro-6-(propylamino)benzothiazole or a pharmaceutically acceptable salt thereof, wherein the amyotrophic lateral sclerosis is treated. In certain embodiments, the definite amyotrophic lateral sclerosis is definite ALS as defined by the El Escorial diagnosis criteria. In certain embodiments, the subject has upper motor neuron degeneration and lower motor neuron degeneration in the bulbar region and two other spinal regions. In certain embodiments, the subject has upper motor neuron degeneration and lower motor neuron degeneration in three spinal regions. In certain embodiments, the subject is selected from a subject with symptom onset duration of less than about 18 months, a subject with a high level of serum creatinine, a subject with low levels of serum sodium bicarbonate, a subject with concomitant riluzole administration and combinations thereof. In certain embodiments, a subject with a high level of serum creatinine is a subject with greater than about 72 µmol/L serum creatinine.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

Embodiments are directed to methods for treating amyotrophic lateral sclerosis in a subject diagnosed with definite amyotrophic lateral sclerosis comprising administering to the subject a therapeutically effective amount of (6R)-2-amino-4,5,6, 7-tetrahydro-6-(propylamino)benzothiazole or a pharmaceutically acceptable salt thereof, wherein the amyotrophic lateral sclerosis is treated. In some embodiments definite amyotrophic lateral sclerosis is the presence of the El Escorial diagnosis criteria, amyotrophic lateral sclerosis symptom onset duration of less than about 18 months, limb-onset amyotrophic lateral sclerosis, concomitant riluzole administration, an ALSFRS-R score of greater than 36.0, a pre-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 µmol/L, a phosphorous value of less than or equal to 1.090µmol/L, a platelet count of less than or equal to 248.0 ×109 cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4mmol/L, a uric acid level of greater than 320.0 µmol/L, a gamma-glutamyltransferase (GGT) level of greater than 37.0U/L, a total bilirubin level of less than or equal to 6.0 µmol/L, a urine pH of less than or equal to 5.5, or any combination thereof.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In certain embodiments, the method further comprises monitoring said subject for any clinical features associated with amyotrophic lateral sclerosis.

In certain embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

Embodiments are directed to methods for treating amyotrophic lateral sclerosis in a subject exhibiting symptoms of amyotrophic lateral sclerosis comprising administering to the subject a therapeutically effective amount of (6R)-2-amino-4,5,6, 7-tetrahydro-6-(propylamino)benzothiazole or a pharmaceutically acceptable salt thereof, wherein the symptoms of amyotrophic lateral sclerosis are treated. In some embodiments, the subject exhibits clinical characteristics selected from definite amyotrophic lateral sclerosis, amyotrophic lateral sclerosis symptom onset duration of less than about 18 months, limb-onset amyotrophic lateral sclerosis, concomitant riluzole administration, an ALSFRSR score of greater than 36.0, a pre-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 µmol/L, a phosphorous value of less than or equal to 1.090µmol/L, a platelet count of less than or equal to 248.0 ×109 cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4mmol/L, a uric acid level of greater than 320.0 µmol/L, a gamma-glutamyltransferase (GGT) level of greater than 37.0U/L, a total bilirubin level of less than or equal to 6.0 µmol/L, a urine pH of less than or equal to 5.5, or any combination thereof. In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6, 7-tetrahydro-6-(propylamino) benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In embodiments, the methods further comprise monitoring said subject for any clinical features associated with amyotrophic lateral sclerosis. In embodiments, the methods further comprise initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6, 7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

Embodiments are directed to methods for treating amyotrophic lateral sclerosis in a subject in need thereof comprising administering to the subject a therapeutically effective amount of (6R)-2-amino-4,5,6,7-tetrahydro-6-(propylamino)benzothiazole or a pharmaceutically acceptable salt thereof and administering to the subject a therapeutically effective amount of riluzole, wherein the amyotrophic lateral sclerosis is treated. In certain embodiments, the therapeutically effective amount of riluzole is about 50 milligrams twice daily. In certain embodiments, the (6R)-2-amino-4,5,6,7-tetrahydro-6-(propylamino)benzothiazole or a pharmaceutically acceptable salt thereof and said riluzole are administered sequentially or simultaneously. In certain embodiments, the subject is selected from a subject with definite amyotrophic lateral sclerosis, subject with limb-onset amyotrophic lateral sclerosis, a subject with amyotrophic lateral sclerosis symptom onset duration of less than about 18 months, a subject with low bicarbonate levels, a subject with a high level of serum creatinine, and a combination thereof. In certain embodiments, a subject with a high level of serum creatinine is a subject with greater than about 72 µmol/L serum creatinine. In certain embodiments, the therapeutically effective amount of (6R)-2-amino-4,5,6, 7-tetrahydro-6-(propylamino)benzothiazole or a pharmaceutically acceptable salt thereof is from 50 milligrams to 3,000 milligrams per day.

In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In certain embodiments, the method further comprises monitoring said subject for any clinical features associated with amyotrophic lateral sclerosis. In certain embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6, 7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

Further embodiments are directed to methods for treating amyotrophic lateral sclerosis in a subject in need thereof comprising administering to the subject with amyotrophic lateral sclerosis symptom duration of less than about 18 months a therapeutically effective amount of (6R)-2-amino-4,5,6,7-tetrahydro-6-(propylamino)benzothiazole or a pharmaceutically acceptable salt thereof, wherein the amyotrophic lateral sclerosis is treated. In certain embodiments, the subject is selected from a subject with definite amyotrophic lateral sclerosis, subject with limb-onset amyotrophic lateral sclerosis, a subject with a high level of serum creatinine, a subject with low bicarbonate levels, a subject with concomitant riluzole administration and a combination thereof. In certain embodiments, a subject with a high level of serum creatinine is a subject with greater than about 72 µmol/L serum creatinine.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-

(propylamino)benzothiazole or a pharmaceutically acceptable salt thereof is from 300 milligrams twice daily.

In certain embodiments, the method further comprises monitoring said subject for any clinical features associated with amyotrophic lateral sclerosis. In certain embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

Further embodiments are directed to methods for treating amyotrophic lateral sclerosis in a subject in need thereof comprising administering to the subject with a high level of serum creatinine a therapeutically effective amount of (6R)-2-amino-4,5,6,7-tetrahydro-6-(propylamino)benzothiazole or a pharmaceutically acceptable salt thereof, wherein the amyotrophic lateral sclerosis is treated. In certain embodiments, the subject with a high level of serum creatinine is a male subject with serum creatinine level selected from greater than about 40 µmol/L, greater than about 45 µmol/L, greater than about 50 µmol/L, greater than about 55 µmol/L, greater than about 60 µmol/L, greater than about 65 µmol/L, greater than about 70 µmol/L, greater than about 72 µmol/L of serum creatinine. In certain embodiments, the subject is a male with a high level of serum creatinine is a subject with serum creatinine level selected from about 40 µmol/L, about 45 µmol/L, about 50 µmol/L, about 55 µmol/L, about 60 µmol/L, about 65 µmol/L, about 70 µmol/L, about 72 µmol/L of serum creatinine. In certain embodiments, the subject with a high level of serum creatinine is a female subject with serum creatinine level selected from greater than about 40 µmol/L, greater than about 45 µmol/L, greater than about 50 µmol/L, greater than about 55 µmol/L, greater than about 60 µmol/L, greater than about 65 µmol/L, greater than about 70 µmol/L, greater than about 72 µmol/L of serum creatinine. In certain embodiments, the subject with a high level of serum creatinine is a female subject with serum creatinine level selected from about 40 µmol/L, about 45 µmol/L, about 50 µmol/L, about 55 µmol/L, about 60 µmol/L, about 65 µmol/L, about 70 µmol/L, about 72 µmol/L of serum creatinine.

In certain embodiments, the subject is selected from a subject with definite amyotrophic lateral sclerosis, a subject with amyotrophic lateral sclerosis symptom duration of less than about 18 months, a subject with concomitant riluzole administration and a combination thereof.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

Embodiments are directed to methods of treating amyotrophic lateral sclerosis in a subject in need thereof comprising monitoring said subject for any clinical features associated with amyotrophic lateral sclerosis; and initiating therapy with (6R)-2-amino-4,5,6,7-tetrahydro-6-(propylamino)benzothiazole or a pharmaceutically acceptable salt thereof upon diagnosis of definite amyotrophic lateral sclerosis in accordance with the El Escorial diagnostic criteria for amyotrophic lateral sclerosis. In certain embodiments, the therapy is administering an effective amount of (6R)-2- amino-4,5,6,7-tetrahydro-6-(propylamino)benzothiazole or a pharmaceutically acceptable salt thereof daily to said subject.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

Embodiments are directed to methods of treating amyotrophic lateral sclerosis in a subject in need thereof comprising monitoring said subject for any clinical features associated with amyotrophic lateral sclerosis; and initiating therapy with (6R)-2-amino-4,5,6,7-tetrahydro-6-(propylamino)benzothiazole or a pharmaceutically acceptable salt thereof upon diagnosis of definite amyotrophic lateral sclerosis. In some embodiments, a diagnosis of definite amyotrophic is characterized by definite ALS as defined by the El Escorial diagnosis criteria, amyotrophic lateral sclerosis symptom onset duration of less than about 18 months, limb-onset amyotrophic lateral sclerosis, concomitant riluzole administration, an ALSFRS-R score of greater than 36.0, a pre-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 μmol/L, a phosphorous value of less than or equal to 1.090 μmol/L, a platelet count of less than or equal to 248.0 ×109 cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4mmol/L, a uric acid level of greater than 320.0 μmol/L, a gamma-glutamyltransferase (GGT)level of greater than 37.0 U/L, a total bilirubin level of less than or equal to 6.0 μmol/L, a urine pH of less than or equal to 5.5, or any combination thereof. In certain embodiments, the therapy is administering an effective amount of (6R)-2-amino-4,5,6,7-tetrahydro-6-(propylamino)benzothiazole or a pharmaceutically acceptable salt thereof daily to said subject.

In certain embodiments, the therapeutically effective amount of (6R)-2-amino-4,5,6,7-tetrahydro-6-(propylamino)benzothiazole or a pharmaceutically acceptable salt thereof is from 50 milligrams to 3,000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 3000 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 900 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 600 milligrams per day. In certain embodiments, the therapeutically effective amount of (6R)-2-amino-4,5,6,7-tetrahydro-6-(propylamino)benzothiazole or a pharmaceutically acceptable salt thereof is from 150 milligrams to 300 milligrams per day. In certain embodiments, the therapeutically effective amount of (6R)-2-amino-4,5,6,7-tetrahydro-6-(propylamino)benzothiazole or a pharmaceutically acceptable salt thereof is 150 milligrams twice daily. In certain embodiments, the therapeutically effective amount of (6R)-2-amino-4,5,6,7-tetrahydro-6-(propylamino)benzothiazole or a pharmaceutically acceptable salt thereof is from 300 milligrams twice daily.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

Embodiments are directed to methods of reducing the decline of serum creatinine in a subject having definite amyotrophic lateral sclerosis comprising administering to the subject a therapeutically effective amount of (6R)-2-amino-4,5,6,7-tetrahydro-6-(propylamino)benzothiazole or a pharmaceutically acceptable salt thereof. In certain embodiments, the subject further has at least one of the following characteristics: limb-onset amyotrophic lateral sclerosis, low bicarbonate levels, symptom onset duration of less than about 18 months, greater than about 72 μmol/L serum creatinine, and concomitant riluzole administration. In certain embodiments, the method further comprises monitoring said subject for any clinical features associated with amyotrophic lateral sclerosis. In certain embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

Other embodiments are directed to methods of reducing the decline of muscle loss in a subject having definite amyotrophic lateral sclerosis comprising administering to the subject a therapeutically effective amount of (6R)-2-amino-4,5,6,7-tetrahydro-6-(propylamino)benzothiazole or a pharmaceutically acceptable salt thereof. In certain embodiments, the subject further has at least one of the following characteristics: limb-onset amyotrophic lateral sclerosis, low bicarbonate levels, symptom onset duration of less than about 18 months, greater than about 72 μmol/L serum creatinine, and concomitant riluzole administration. In certain embodiments, the method further comprises monitoring said subject for any clinical features associated with amyotrophic lateral sclerosis. In certain embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

In certain embodiments, the pharmaceutical composition is selected from a tablet, a capsule and a liquid.

In certain embodiments, the (6R)-2-amino-4,5,6,7-tetrahydro-6-(propylamino)benzothiazole or a pharmaceutically acceptable salt thereof is administered orally.

Embodiments are also directed to methods of treating amyotrophic lateral sclerosis in a subject in need thereof comprising orally administering to said subject 150 milligrams of (6R)-2-amino-4,5,6,7-tetrahydro-6-(propylamino)benzothiazole dihydrochloride monohydrate in a tablet pharmaceutical composition twice daily to said subject, wherein the subject is selected from a subject with definite amyotrophic lateral sclerosis, limb-onset amyotrophic lateral sclerosis a subject with amyotrophic lateral sclerosis symptom onset duration of less than about 18 months, a subject with a high level of serum creatinine, a subject with low bicarbonate levels, a subject with concomitant riluzole administration and combinations thereof, and wherein the amyotrophic lateral sclerosis is treated. In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient. In certain embodiments, a subject with a high level of serum creatinine is a subject with greater than about 72 μmol/L serum creatinine. In certain embodiments, the method further comprises monitoring said subject for any clinical features associated with amyotrophic lateral sclerosis. In certain embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

Embodiments are also directed to methods of treating amyotrophic lateral sclerosis in a subject in need thereof comprising orally administering to said subject 150 milligrams of (6R)-2-amino-4,5,6,7-tetrahydro-6-(propylamino)benzothiazole dihydrochloride monohydrate in a tablet pharmaceutical composition twice daily to said subject, wherein the subject suffers from definite amyotrophic lateral sclerosis, with a symptom onset duration of less than about 18 months, a subject with a high level of serum creatinine, limb-onset amyotrophic lateral sclerosis, low bicarbonate levels, and concomitant riluzole administration, and wherein the amyotrophic lateral sclerosis is treated. In certain embodiments, the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient. In certain embodiments, a subject with a high level of serum creatinine is a subject with greater than about 72 µmol/L serum creatinine. In certain embodiments, the method further comprises monitoring said subject for any clinical features associated with amyotrophic lateral sclerosis. In certain embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

In certain embodiments, the pharmaceutical composition is chirally pure for (6R)-2-amino-4,5,6,7-tetrahydro-6-(propylamino)benzothiazole or a pharmaceutically acceptable salt thereof. In certain embodiments, the chiral purity for (6R)-2-amino-4,5,6,7-tetrahydro-6-(propylamino)benzothiazole or a pharmaceutically acceptable salt thereof is about 99% or more, including about 99.95% or more. In certain embodiments, the chemical purity for (6R)-2-amino-4,5,6,7-tetrahydro-6-(propylamino)benzothiazole or a pharmaceutically acceptable salt thereof is about 99% or more, including about 99.97% or more.

Another method for treating amyotrophic lateral sclerosis (ALS) in a subject comprises determining a baseline ALS Functional Rating Scale, Revised (ALSFRS-R) scores for the subject; administering to the subject an effective amount of about chirally pure (6R)-2-amino-4,5,6,7-tetrahydro-6-(propylamino)benzothiazole or pharmaceutically acceptable salt thereof; collecting outcome data from the subject; analyzing the outcome data as a primary endpoint in a joint-rank statistical test adjusted for mortality and adjusted for a change from baseline using ALS Functional Rating Scale, Revised (ALSFRS-R) scores from a plurality of persons for indications of efficacy or non-efficacy; and continuing to administer an effective amount to the subject if the joint-rank statistical test indicates the effective amount is efficacious, but discontinuing to administer an effective amount to the subject if the joint-rank statistical test indicates the effective amount is non-efficacious.

The ALSFRS-R measures 4 domains: pulmonary function, bulbar function, and gross and fine motor skills. There are a total of 12 questions, each scored from 0 to 4 for a total possible score of 48. The twelve questions and rating scale are provided in Cederbaum, et al., 169 J. NEUROL. SCI., 13-21 (1999) which is incorporated herein in its entirety.

In some embodiments, the analysis utilizes a greater negative adjustment for a death of one of the plurality of persons than for a survival with functional decline, if a higher rank is a better global clinical outcome. In embodiments, the analysis provides a greater negative adjustment for an earlier death of one of the plurality of persons than for a later death of a person, if a higher rank is a better global clinical outcome. Embodiments may collect outcome data by phone interview, home visit, or combinations thereof. Other embodiments may have collecting outcome data in part by phone interview or home visit or combinations thereof. In some embodiments, the outcome data is selected from laboratory tests, ALSFRS-R score, adverse event reporting, or a combination thereof. The method may have the change from baseline determined through twelve months follow-up. In some embodiments, the method further comprises determining a secondary endpoint data of evaluation of time to death or respiratory insufficiency, respiratory decline, muscle strength, quality of life, population PK, and safety. The quality of life may be assessed using an amyotrophic lateral sclerosis (ALS) assessment questionnaire and a change-in-health survey.

In some embodiments, treating ALS can include slowing progression of ALS, reducing intensity of symptoms associated with ALS, reducing onset of symptoms associated with ALS, reducing weight loss associated with ALS, reversing weight loss associated with ALS, delaying mortality, and combinations thereof. In particular embodiments, the symptoms associated with ALS may be, for example, decreases in fine motor function, decreases in gross motor function, decreases in bulbar function, decreases in respiratory function, and combinations thereof. Further, in other embodiments, the symptoms associated with ALS can include difficulty with daily activities, such as, for example, difficulty with walking, speech, eating, swallowing, writing, climbing stairs, cutting food, turning in bed, dressing, maintaining hygiene, and combinations thereof, and may experience other symptoms, such as, for example, difficulty breathing, dyspnea, orthopnea, respiratory insufficiency, increased salivation and combinations thereof.

In some embodiments, the effective amount may be from about 50 milligrams to about 300 milligrams per day, and in other embodiments, the effective amount may be from about 150 milligrams to about 300 milligrams per day. In still other embodiments, the effective amount may be about 300 milligrams or more per day. In other embodiments, the stable daily dose may be one to five unit doses per day, and in particular embodiments, each unit dose may be a solid unit dose. In some embodiments, administering may include administering one unit dose two times per day wherein each unit dose is equal to about one-half of the stable daily dose, and in other embodiments, administering may include administering one unit dose once every twelve hours wherein each unit dose is equal to about one-half of the stable daily dose. In still other embodiments, administering may include administering one unit dose four times per day wherein each unit dose is equal to about one-quarter of the stable daily dose. In yet other embodiments, administering can include administering two unit doses wherein each unit dose is about 150 milligrams two times per day, and in further embodiments, administering may include administering four unit doses wherein each unit dose is about 75 milligrams four times per day.

In some embodiments, the method is carried out for a time period selected from at least about twelve months, at least about eighteen months, at least about two years, at least about four years, at least about six years, at least about eight years, at least about ten years, at least about twenty years, and until the subject dies. In other embodiments, the method is carried out at least daily for an indefinite amount of time.

In some embodiments, the method further comprises administering one or more other amyotrophic lateral sclerosis (ALS) treatments simultaneously or concurrently with administering about chirally pure (6R)-2-amino-4,5,6,7-tetrahydro-6-(propylamino)benzothiazole or a pharmaceutically acceptable salt thereof. In particular embodiments, the one or more other amyotrophic lateral sclerosis (ALS) treatments include riluzole.

In some embodiments, the subject began exhibiting symptoms of amyotrophic lateral sclerosis (ALS) less than about two years before beginning administering of (6R)-2-amino-4,5,6,7-tetrahydro-6-(propylamino)benzothiazole or pharmaceutically acceptable salt thereof. In other embodiments, the subject began exhibiting symptoms of amyotrophic lateral sclerosis (ALS) at least greater than about two years before beginning administering of (6R)-2-amino-4,5,6,7-tetrahydro-6-(propylamino)benzothiazole or pharmaceutically acceptable salt thereof. In some embodiments, the subject exhibits a greater than 20% improvement in ALS Functional Rating Scale, Revised (ALSFRS-R) score when compared to baseline. In particular embodiments, the subject exhibits a greater than 30% improvement in ALS Functional Rating Scale, Revised (ALSFRS-R) score when compared to baseline. In still other embodiments, the improvement is apparent in a time period selected from the group consisting of less than thirty-six months, less than eighteen months, less than twelve months, less than about nine months, less than about six months, less than about three months, and less than about one month. Further, in some embodiments, administering about chirally pure (6R)-2-amino-4,5,6,7-tetrahydro-6-(propylamino)benzothiazole or pharmaceutically acceptable salt thereof results in slowing of a rate of fine motor function loss in the subject.

In some embodiments, the method further comprises administering a daily dose of greater than an effective amount for a period of time before administering an effective amount of about chirally pure (6R)-2-amino-4,5,6,7-tetrahydro-6-(propylamino)benzothiazole or pharmaceutically acceptable salt thereof. In particular embodiments, the greater than an effective amount is greater than 150 milligrams. In still other embodiments, the greater than an effective amount is greater than 300 milligrams. In some embodiments, the period of time before administering an effective amount is from about one week to about eighteen months. In particular embodiments, the period of time before administering an effective amount is from about two weeks to about twelve months. Further, in some embodiments, administering an effective amount of about chirally pure (6R)-2-amino-4,5,6,7-tetrahydro-6-(propylamino)benzothiazole or pharmaceutically acceptable salt thereof is carried out indefinitely.

In some embodiments, an effective amount of about chirally pure (6R)-2-amino-4,5,6,7-tetrahydro-6-(propylamino)benzothiazole or pharmaceutically acceptable salt thereof is administered in an initial dose and every administration thereafter. In other embodiments, dosing achieves a dose dependent, steady state $AUC_{0-12}$ (hours×ng/mL) selected from the group consisting of 836±234 for an effective amount of 50 milligrams, 2803±1635 for an effective amount of 150 milligrams, and 6004±2700 for an effective amount of 300 milligrams.

In some embodiments, the effective amount comprises a stable daily dose. In particular embodiments, the stable daily dose comprises from about 50 mg to about 300 mg of about chirally pure (6R)-2-amino-4,5,6,7-tetrahydro-6-(propylamino)benzothiazole or pharmaceutically acceptable salt thereof. In other embodiments, the stable daily dose comprises one to five unit doses per day. In still other embodiments, each unit dose is a solid unit dose. In some embodiments, administering comprises administering one unit dose two times per day wherein each unit dose is equal to about half of the stable daily dose. In other embodiments, administering comprises administering one unit dose once every twelve hours wherein each unit dose is equal to about half of the stable daily dose. In still other embodiments, administering comprises administering one unit dose four times per day wherein each unit dose is equal to about one quarter of the stable daily dose. In yet other embodiments, administering comprises administering two unit doses wherein each unit dose is about 150 milligrams two times per day. Further, some embodiments, administering comprises administering four unit doses wherein each unit dose is about 75 milligrams four times per day. In some embodiments, administering a stable daily dose of about chirally pure (6R)-2-amino-4,5,6,7-tetrahydro-6-(propylamino)benzothiazole or pharmaceutically acceptable salt thereof is carried out for at least about eighteen months. Further, in some embodiments, administering a stable daily dose of about chirally pure (6R)-2-amino-4,5,6,7-tetrahydro-6-(propylamino)benzothiazole or pharmaceutically acceptable salt thereof is carried out for an indefinite amount of time. In some embodiments, the stable daily dose is consistent throughout a treatment regimen. In particular embodiments, an initial daily dose is equal to each daily dose thereafter. In other embodiments, there is not titration before administering the stable daily dose. In yet other embodiments, administering achieves a dose dependent, steady state $AUC_{0-12}$ (h×ng/mL) selected from 836±234 for stable daily dose of 50 milligrams, 2803±1635 for stable daily dose of 150 milligrams, or 6004±2700 for stable daily dose of 300 milligrams.

In some embodiments, the method further comprises monitoring the subject. In some embodiments, the method further comprises monitoring the subject for neutropenia. In particular embodiments, the method further comprises monitoring the ALS Functional Rating Scale, Revised (ALSFRS-R) score for the subject. In other embodiments, the method further comprises monitoring the subject's fine motor function, gross motor function, bulbar function, respiratory function, and combinations thereof. In still other embodiments, the method further comprises monitoring behaviors selected from the group consisting of swallowing, handwriting, speech, ability to walk, ability to climb stairs, ability to dress, ability to maintain hygiene, and combinations thereof. In some embodiments, the method further comprises scheduling a doctor visit every six months for at least twelve months. In various embodiments, the subject is predisposed to amyotrophic lateral sclerosis (ALS) and is not exhibiting symptoms of amyotrophic lateral sclerosis (ALS). In some embodiments, the method further comprises administering about chirally pure (6R)-2-amino-4,5,6,7-tetrahydro-6-(propylamino)benzothiazole or pharmaceutically acceptable salt thereof to family members of the subject. In other embodiments, treating comprises administering the about chirally pure (6R)-2-amino-4,5,6,7-tetrahydro-6-(propylamino)benzothiazole or pharmaceutically acceptable salt thereof to a subject not exhibiting symptoms of amyotrophic lateral sclerosis (ALS). Further, in some embodiments, treating comprises administering the about chirally pure (6R)-2-amino-4,5,6,7-tetrahydro-6-(propylamino)benzothiazole or pharmaceutically acceptable salt thereof to a subject that is predisposed to amyotrophic lateral sclerosis (ALS).

A method of the application is for conducting a clinical trial for treating amyotrophic lateral sclerosis (ALS). The method comprises a clinical trial to evaluate the efficacy of a pharmaceutical agent. An embodiment comprises steps to evaluate the efficacy of dexpramipexole for treating ALS. In embodiments, the method provides for administering to the plurality of subjects an effective amount of about chirally pure dexpramipexole or pharmaceutically acceptable salt thereof. In some embodiments, the clinical trial is carried out versus placebo in subjects with ALS.

Embodiments are directed to methods for conducting a clinical trial for treating ALS in a plurality of subjects. In particular, the ALS Functional Rating Scale, Revised (ALS-FRS-R) scores may be determined for the subjects to determine a plurality of baseline numbers. The method may further comprise the collecting of outcome data from the subjects. The method comprises analyzing the outcome data as a primary endpoint in a joint-rank statistical test adjusted for mortality and adjusted for a change from baseline in ALS Functional Rating Scale, Revised (ALSFRS-R) score. In some embodiments, the analysis provides a greater negative adjustment for a death of a subject than for a survival with functional decline, if a higher rank is a better global clinical outcome. In embodiments, the analysis provides a greater negative adjustment for an earlier death of a subject than for a later death of a subject, if a higher rank is a better global clinical outcome. Embodiments may collect outcome data by phone interview, home visit, or combinations thereof. Other embodiments may have collecting outcome data in part by phone interview or home visit or combinations thereof. In some embodiments, the outcome data is selected from laboratory tests, ALSFRS-R score, adverse event reporting, or a combination thereof. The method may have the change from baseline determined through twelve months follow-up. In some embodiments, the method further comprises determining a secondary endpoint data of evaluation of time to death or respiratory insufficiency, respiratory decline, muscle strength, quality of life, population PK, and safety. The quality of life may be assessed using an amyotrophic lateral sclerosis (ALS) assessment questionnaire and a change-in-health survey.

In various embodiments, dexpramipexole administered or incorporated into the pharmaceutical compositions may be chirally pure or enantiomerically enriched to such an extent that the effects of any dopaminergic agonist activity associated with residual pramipexole is either absent or sufficiently small to allow for high dosage administration of dexpramipexole relative to enantiomerically pure or enantiomerically enriched pramipexole.

Accordingly, embodiments of methods for a clinical trial for treating ALS may include administering dexpramipexole for an extended, prolonged, or indefinite period of time. In some embodiments, the extended period of time may be about twelve weeks or longer, about six months or longer, about one year or longer, and in other embodiments, a method of treating ALS comprises administering dexpramipexole on a maintenance dosing regimen. Thus, various embodiments are directed to maintenance therapy in which a dosing schedule for dexpramipexole is maintained for an extended period of time without titration or otherwise changing the dosing schedule. In such embodiments, the extended period of time may be about 12 weeks or longer, about 6 months or longer, about one year or longer, two, three, four, five, or ten years or longer, and in certain embodiments, an indefinite period of time.

In various embodiments, dexpramipexole may be administered to a plurality of individuals exhibiting the symptoms of a neurodegenerative disease or to a plurality of individuals predisposed to a neurodegenerative disease. Non-limiting examples of neurodegenerative diseases that may be treated using dexpramipexole include Huntington's Chorea, metabolically induced neurological damage, Alzheimer's disease, senile dementia, age associated cognitive dysfunction, vascular dementia, multi-infarct dementia, Lewy body dementia, neurodegenerative dementia, neurodegenerative movement disorder, ataxia, Friedreich's ataxia, multiple sclerosis, spinal muscular atrophy, primary lateral sclerosis, seizure disorders, motor neuron disorder or disease, inflammatory demyelinating disorder, Parkinson's disease, ALS, hepatic encephalopathy, and chronic encephalitis, or any combination thereof. Thus, the compositions and methods may be used to treat nearly individuals exhibiting symptoms of a neurological disease or susceptible to such diseases.

In further embodiments, the clinical trial may be carried out with various subjects in combination with other forms of treatment. In some embodiments, such combination therapy may produce synergistic effects, such that the effect of dexpramipexole is augmented wherein one or more symptoms show a dramatic improvement over pre-treatment levels. For example, in certain embodiments, dexpramipexole treatment may be carried out in combination with (simultaneously or concurrently) with riluzole without adverse effects or reduced symptom relief.

The method will use the efficacy population for analysis of the primary outcome consisting of all subjects who receive at least one dose of drug and have one evaluation. The intent-to-treat (ITT) population, consisting entirely of randomized subjects, will be used for the secondary and tertiary endpoints. Key outcomes data, such as survival status, will continue to be collected for those subjects who discontinue the study up to what would have been their Month 18 visit, or the study completion date, whichever comes first. The impact of any missing data will be assessed in the sensitivity analysis.

The inclusion in the method of outcome measures, such as, for example, respiratory status, quality of life, functional independence, and caregiver burden, yields data to support a thorough evaluation of the efficacy of dexpramipexole in ALS. In addition, ongoing safety data collection in the larger and more geographically diverse subject population augments the safety profile for dexpramipexole based on earlier-phase clinical studies.

An embodiment of the method includes subjects with "possible ALS". Expanding the subject inclusion criteria impacts enrollment. Including subjects earlier in the disease process may enhance the potential to observe a response to treatments that are putatively neuroprotective.

The designs of the methods include several features to promote subject retention and decrease the subject and caregiver burden. Retention of study participants is important because early discontinuation creates a missing data dilemma, which may weaken positive results in clinical trials. In ALS, progression of the underlying disease may contribute to dropout rates as subjects are physically challenged to meet requirements for study participation. The method offers accommodation/planning for subjects who are housebound or under hospice care. Once approved by the investigator, continued participation requires only clinical laboratory tests, adverse event (AE) reporting, and ALS-FRS-R assessments. All required information can be collected by phone interview or home visit. The discontinuation rate in the method is much lower than that observed in most prior clinical trials in ALS.

The method is one of the larger late-stage interventional clinical trials in ALS to date and is utilizing a novel endpoint (Combined Assessment of Function and Survival) that accounts for treatment effects on both survival and function. The method is designed to provide evidence regarding the efficacy of dexpramipexole in subjects with ALS.

For the first time in ALS clinical studies, function and survival will be analyzed in a combined assessment as the primary endpoint. The Combined Assessment of Function and Survival (CAFS) analysis accounts for death by appropriately defining death as a worse outcome than survival with any degree of functional decline and subjects who die early in the study being defined as a worse outcome than those who die later in the study. This innovative method was used to address the challenge, noted in trials of other potential ALS treatments, of how to take mortality into account when looking at a functional outcome measure.

Another method for treating ALS in a subject comprises administering to the subject an effective amount of about chirally pure (6R)-2-amino-4,5,6,7-tetrahydro-6(propylamino)benzothiazole or pharmaceutically acceptable salt thereof, and continuing to administer an effective amount of about chirally pure (6R)-2-amino-4,5,6,7-tetrahydro-6-(propylamino)benzothiazole or pharmaceutically acceptable salt thereof to the subject if there is an improvement in the subject's ALSFRS-R score from a previous ALSFRS-R score of the subject. In some embodiments, the method further comprises determining a baseline ALS Functional Rating Scale, Revised (ALSFRS-R) score for the subject. In other embodiments, the method further comprises collecting outcome data from the subject. Further, the embodiment may further comprise analyzing the outcome data as a primary endpoint in a joint-rank statistical test adjusted for mortality and adjusted for a change from baseline using ALS Functional Rating Scale, Revised (ALSFRS-R) scores from a plurality of persons for indications of efficacy or non-efficacy. In still other embodiments, the improvement in the subject's ALSFRS-R score is statistically significant. In yet other embodiments, the improvement in the subject's ALSFRS-R score is statistically significant as defined in the EMPOWER phase III clinical trial. And in some embodiments, the improvement in the subject's ALSFRS-R score is statistically significant compared to the change in baseline ALSFRS-R scores using follow-up data through 12 months in a population of ALS subjects receiving an effective amount of about chirally pure (6R)-2-amino-4,5,6,7-tetrahydro-6-(propylamino)benzothiazole or pharmaceutically acceptable salt thereof.

Another method for treating amyotrophic lateral sclerosis (ALS) in a subject comprises administering to the subject an effective amount of about chirally pure (6R)-2-amino-4,5,6,7-tetrahydro-6-(propylamino)benzothiazole or pharmaceutically acceptable salt thereof; and continuing to administer an effective amount of about chirally pure (6R)-2-amino-4,5,6,7-tetrahydro-6-(propylamino)benzothiazole or pharmaceutically acceptable salt thereof to the subject if there is an improvement in the subject's CAFS ranking from a previous CAFS ranking of the subject.

Yet another method for treating amyotrophic lateral sclerosis (ALS) in a subject with possible ALS comprises administering to the subject with possible ALS an effective amount of about chirally pure (6R)-2-amino-4,5,6,7-tetrahydro-6-(propylamino)benzothiazole or pharmaceutically acceptable salt thereof, and continuing to administer an effective amount of about chirally pure (6R)-2-amino-4,5,6,7-tetrahydro-6-(propylamino)benzothiazole or pharmaceutically acceptable salt thereof to the subject if there is an improvement in the subject's ALS symptoms. Some embodiments further comprise determining a baseline ALS Functional Rating Scale, Revised (ALSFRS-R) score for the subject. Other embodiments further comprise collecting outcome data from the subject. The embodiment may further comprise analyzing the outcome data as a primary endpoint in a joint-rank statistical test adjusted for mortality and adjusted for a change from baseline using ALS Functional Rating Scale, Revised (ALSFRS-R) scores from a plurality of persons for indications of efficacy or non-efficacy. In some other embodiments, the improvement in the subject's ALSFRS-R score is statistically significant. In still other embodiments, the improvement in the subject's ALSFRS-R score is statistically significant as defined in the EMPOWER phase III clinical trial. In yet other embodiments, the improvement in the subject's ALSFRS-R score is statistically significant compared to the change in baseline ALSFRS-R scores using follow-up data through 12 months in a population of ALS subjects receiving an effective amount of about chirally pure (6R)-2-amino-4,5,6,7-tetrahydro-6-(propylamino)benzothiazole or pharmaceutically acceptable salt thereof The present application provides methods for treating amyotrophic lateral sclerosis (ALS) in a subject, the method comprising determining a baseline ALS Functional Rating Scale Revised (ALSFRS-S) score for the subject, administering to the subject, one or more single unit doses, each unit dose comprising from about 50 mg to about 150 mg of 99% or greater chirally enriched (6R)-2-amino-4,5,6,7-tetrahydro-6-(propylamino)benzothiazole or a pharmaceutically acceptable salt thereof, providing to the subject, a daily dose of about 50 mg to about 300 mg of the (6R)-2-amino-4,5,6,7-tetrahydro-6-(propylamino)benzothiazole or a pharmaceutically acceptable salt thereof during a treatment time period, collecting outcome data from the subject during the treatment time period, determining an outcome ALSFRS-R score for the subject at the end of the treatment time period, and increasing the amount of (6R)-2-amino-4,5,6,7-tetrahydro-6-(propylamino)benzothiazole or a pharmaceutically acceptable salt thereof in each unit dose if the subject's outcome ALSFRS-R score is lower than the baseline ALSFRS-R score, or maintaining the amount of (6R)-2-amino-4,5,6,7-tetrahydro-6-(propylamino)benzothiazole or a pharmaceutically acceptable salt thereof in each unit dose if the subject's outcome ALSFRS-R score is an improvement over the subject's baseline ALSFRS-R score, wherein the subject is diagnosed with amyotrophic lateral sclerosis (ALS) or is predisposed to amyotrophic lateral sclerosis (ALS) and is not exhibiting any symptoms.

The present application provides for a method of identifying a patient who will respond to treatment with (6R)-2-amino-4,5,6,7-tetrahydro-6-(propylamino)benzothiazole or a pharmaceutically acceptable salt thereof comprising: diagnosing a patient with EEC definite ALS; measuring the serum creatinine levels of the patient; and identifying the patient as a responder if the serum creatinine levels are greater than about 72 μmol/L.

Some embodiments of each of the aforementioned methods are generally directed to pharmaceutical compositions including an effective amount of dexpramipexole and methods for using such pharmaceutical compositions for the treatment of neurological diseases such as, for example, ALS. In particular, embodiments of the various methods are directed to methods for treating neurological diseases including the step of administering at least about 150 milligrams of dexpramipexole per day to a subject in need of treatment, and in other embodiments, at least about 300 milligrams of dexpramipexole may be administered to a subject in need of treatment per day. Such administration may be carried out as a single dose once per day, or in certain embodiments, two or more doses of dexpramipexole may be administered two or more times per day. Therefore, embodiments of the various methods are also directed to pharmaceutical compositions at least including 50 milligrams of dexpramipexole and a pharmaceutically acceptable excipient, and in some embodiments, such pharmaceutical compositions may include at least 75 milligrams, 100 milligrams, 125 milligrams, 150 milligrams, 300 milligrams, 400 milligrams, 500 milligrams, or 600 milligrams of dexpramipexole and one or more pharmaceutically acceptable excipients, which may be administered as described above. In certain embodiments, amyotrophic lateral sclerosis (ALS) may be limb-onset ALS or bulbar-onset ALS.

Some embodiments of the above methods are directed to methods for treating ALS in a plurality of subjects. In particular, the ALS Functional Rating Scale, Revised (ALS-FRS-R) scores may be determined for the subjects to determine a plurality of baseline numbers. In embodiments, the method provides for administering to the plurality of subjects an effective amount of about chirally pure dexpramipexole or pharmaceutically acceptable salt thereof. The method may further comprise the collecting of outcome data from the subjects. The method comprises analyzing the outcome data as a primary endpoint in a joint-rank statistical test adjusted for mortality and adjusted for a change from baseline in ALSFRS-R score. In some embodiments, the analysis provides a greater negative adjustment for a death of a subject than for a survival with functional decline, if a higher rank is a better global clinical outcome. In embodiments, the analysis provides a greater negative adjustment for an earlier death of a subject than for a later death of a subject, if a higher rank is a better global clinical outcome. Embodiments may collect outcome data by phone interview, home visit, or combinations thereof. Other embodiments may have collecting outcome data in part by phone interview or home visit or combinations thereof. In some embodiments, the outcome data is selected from laboratory tests, ALSFRS-R score, adverse event reporting, or a combination thereof. The method may have the change from baseline determined through twelve months follow-up. In some embodiments, the method further comprises determining a secondary endpoint data of evaluation of time to death or respiratory insufficiency, respiratory decline, muscle strength, quality of life, population PK, and safety. The quality of life may be assessed using an amyotrophic lateral sclerosis (ALS) assessment questionnaire and a change-in-health survey.

In various embodiments of the methods above, dexpramipexole administered or incorporated into the pharmaceutical compositions may be enantiomerically pure or enantiomerically enriched to such an extent that the effects of any dopaminergic agonist activity associated with residual (6S)-2-amino-4,5,6,7-tetrahydro-6-(propylamino) benzothiazole (pramipexole) is either absent or sufficiently small to allow for high dosage administration of dexpramipexole relative to enantiomerically pure or enantiomerically enriched pramipexole. A description of methods for producing high purity dexpramipexole can be found in U.S. application Ser. No. 12/049,235, which is hereby incorporated by reference in its entirety. In some embodiments, treatment with dexpramipexole may include administering daily doses of about 100 milligrams or more, about 125 milligrams or more, about 150 milligrams or more, 300 milligrams or more, 400 milligrams or more, 500 milligrams or more, or 600 milligrams or more without the adverse side effects associated with dopaminergic agonism. For example, daily doses of dexpramipexole of about 150 milligrams or more or about 300 milligrams or more may be administered without an apparent impact on heart rate, blood pressure, or other cardiac activity that can be measured using, for instance, ECG or blood pressure cuffs that would otherwise be indicative of treatment with a dopamine agonist. Administrations of about 100 milligrams or more, about 125 milligrams or more, about 150 milligrams or more, 300 milligrams or more, 400 milligrams or more, 500 milligrams or more, or 600 milligrams or more per day of dexpramipexole have not been shown cause any of these side-effects.

Moreover, because dexpramipexole is well tolerated, in some embodiments of the various methods, treatment including administration of daily doses of about 100 milligrams or more, about 125 milligrams or more, about 150 milligrams or more, 300 milligrams or more, 400 milligrams or more, 500 milligrams or more, or 550 milligrams or more of dexpramipexole may be carried out for prolonged periods of time such as, for example, twelve weeks or more, six months or more, one year or more and, in certain embodiments, for two, three, five or ten years or more, and in other embodiments, for an indefinite period of time. Accordingly, embodiments of various methods include methods of treating ALS may include administering dexpramipexole for an extended, prolonged, or indefinite period of time. In some embodiments, the extended period of time may be about twelve weeks or longer, about six months or longer, about one year or longer, and in other embodiments, a method of treating ALS comprises administering dexpramipexole on a maintenance dosing regimen. In such embodiments, the maintenance dosing regimen may include administering about 100 milligrams or more, about 125 milligrams or more, about 150 milligrams or more, 300 milligrams or more, 500 milligrams or more, or 550 milligrams or more of dexpramipexole per day without any titration (or an initial dosing regimen of less than the maintenance dose). Thus, various embodiments are directed to maintenance therapy in which a dosing schedule for dexpramipexole is maintained for an extended period of time without titration or otherwise changing the dosing schedule. In such embodiments, the extended period of time may be about 12 weeks or longer, about 6 months or longer, about one year or longer, two, three, four, five, or ten years or longer, and in certain embodiments, an indefinite period of time. In other embodiments, the maintenance dosing may include administering less than the initial daily dose, such as, less than about 150 milligrams or less than about 300 milligrams of dexpramipexole per day. Additionally, without wishing to be bound by theory, the adverse effects associated with dopamine agonist treatment such as those described above may not develop after treatment with dexpramipexole has been carried out for a period of time of at least twelve weeks or more, and in some embodiments at least six months or one, two, three, five or ten years or more.

In further embodiments of the various methods, an initial dosing regimen may be provided. In certain embodiments, the initial dosing regimen may include administering a higher dose of dexpramipexole than the maintenance dosing regimen as either a single administration or by administering an increased dosage for a limited period of time prior to beginning a maintenance dosing regimen. For example, in certain embodiments, the initial dosing regimen may be about 300 milligrams to about 500 milligrams or more of dexpramipexole per day. This initial dosing regimen may continue for one, two, three, four, five, six, or seven days, up to four weeks, up to eight weeks, or up to twelve weeks. Following the initial dosing regimen, the subject may be administered a maintenance dosing regimen of, for example, about 100 milligrams or more, about 125 milligrams or more, about 150 milligrams or more, 300 milligrams or more, 400 milligrams or more, 500 milligrams or more, or 550 milligrams or more of dexpramipexole for an indefinite period of time such as, for example, at least twelve weeks or more, or at least six months, or one, two, three, five or ten years or more. In some embodiments, subjects undergoing maintenance may be administered one or more higher dosage treatments at one or more times during the maintenance dosage regimen.

In various embodiments of the various methods, dexpramipexole may be administered to any individual exhibiting the symptoms of a neurodegenerative disease or to individuals predisposed to a neurodegenerative disease. Non-limiting examples of neurodegenerative diseases that may be treated using dexpramipexole include Huntington's Chorea, metabolically induced neurological damage, Alzheimer's disease, senile dementia, age associated cognitive dysfunction, vascular dementia, multi-infarct dementia, Lewy body dementia, neurodegenerative dementia, neurodegenerative movement disorder, ataxia, Friedreich's ataxia, multiple sclerosis, spinal muscular atrophy, primary lateral sclerosis, seizure disorders, motor neuron disorder or disease, inflammatory demyelinating disorder, Parkinson's disease, ALS, hepatic encephalopathy, and chronic encephalitis, or any combination thereof. Thus, the compositions and methods of the various methods may be used to treat nearly any individual exhibiting symptoms of a neurological disease or susceptible to such diseases.

In particular embodiments of the various methods, dexpramipexole may be used to treat ALS. For example, in some embodiments, individuals diagnosed with ALS within two years or less may be treated with dexpramipexole to reduce, eliminate, or slow advancement of ALS or symptoms associated with ALS such as, for example, fine motor function loss, gross motor function loss, loss of bulbar function, and loss of respiratory function. In other embodiments, dexpramipexole may be administered to reduce or slow the advancement of symptoms including, but not limited to, trembling, loss of muscle control, loss of ability to write, loss of ability to move or roll over, loss of speech, inability to swallow, difficulty breathing, and so on. In other embodiments, individuals with advanced symptoms or individuals who were diagnosed with ALS more than two years before beginning treatment may be treated with dexpramipexole, and such individuals may respond to treatment by exhibiting a reduction or elimination of one or more symptoms related to ALS, or in certain embodiments, the rate of symptom onset or advancement may be reduced, for example; the rate of motor function loss, the rate of loss of speech, and/or difficulty swallowing may be slowed and/or reduced.

In further embodiments of the various methods, a dose-dependent response may be associated with treatment with dexpramipexole, and in certain embodiments, a dose-dependent response may be enhanced when treatment is carried out for longer periods of time. For example, in some embodiments, a naïve subject who is administered a daily dose of, for example, about 300 milligrams of dexpramipexole or more, about 500 milligrams or more, or about 600 milligrams or more, may exhibit greater improvement in one or more symptoms of a neurological disease than a similarly situated naïve subject who is administered a daily dose of dexpramipexole less than 300 milligrams, less than 500 milligrams, or less than 600 milligrams. In such embodiments, improvement resulting from higher dosage administration may be apparent after a single treatment. Moreover, in some embodiments, enhanced improvement in one or more symptoms as a result of administration of higher daily doses of dexpramipexole may be observed up to six months or more after beginning such treatment. Thus, in particular embodiments, treatment with higher doses of dexpramipexole may be carried out for prolonged periods of time, and the improvement associated with such dexpramipexole treatment may be realized after treatment has been carried out for a time period of, for example, one, two, three, four, five, six, or seven days, up to one, two, four, six, eight, twelve, twenty-four, or forty-eight weeks, up to five, ten, fifteen, or twenty years, or any length of time between the recited values. In further embodiments, treatment with higher doses of dexpramipexole may be carried out as maintenance therapy, wherein the subject is administered such doses of dexpramipexole at the initiation of treatment and, thereinafter continue such doses of dexpramipexole over time. In each of the method embodiments described herein, any of the doses of dexpramipexole and/or any of the dosing regimens of dexpramipexole described herein may be used in such methods and continued administration of the doses may be continued for any of the described periods of time.

In certain embodiments of the various methods, the observed improvement in one or more symptoms may become enhanced as treatment progresses such that after an improvement in one or more symptoms is observed further improvements in one or more symptoms may become evident with continued treatment. Without wishing to be bound by theory, a lag between beginning treatment and the first observation of improvement may be due to a period in which the dexpramipexole concentration in one or more of the subject's tissues increases to a threshold level where symptom improvement is observed. Any lag before observation of improvement may vary between subjects and may vary depending on, for instance, the subject's demographics or characteristics such as, for example, age, progression of the disease, and/or the time between the onset of symptoms of the disease and beginning treatment, or any combination of the demographics or characteristics thereof.

In additional embodiments of the various methods, dexpramipexole may be administered to subjects in need of treatment for excessive weight loss associated with ALS. Without wishing to be bound by theory, the precipitous weight loss that is a cardinal symptom of ALS may be associated with increased energy expenditure, skeletal muscle hypermetabolism, and the systematic wasting of muscle tissue known as cachexia. In various embodiments, the total daily dose of dexpramipexole administered may be for example, less than 150 milligrams to 300 milligrams or greater, 400 milligrams or greater, 500 milligrams or greater, or 600 milligrams or greater. In each of the method embodiments described herein, any of the doses of dexpramipexole and/or any of the dosing regimens of dexpramipexole described herein may be used in such methods and continued administration of the doses may be continued for any of the described periods of time.

In some embodiments of the various methods, dexpramipexole may be administered by titration where one or more initial doses are less than 150 milligrams, less than 300 milligrams, less than 400 milligrams, less than 500 milligrams, less than 600 milligrams, and so on when administered to naïve subjects. Dexpramipexole treatment may further comprise titration because pramipexole has a significant adverse impact on naïve subjects, and titration over the course of weeks in which the dosage regimen is periodically increased to reach higher dosages purportedly limits these adverse effects. In various embodiments, of the various methods, no titration of dexpramipexole is required. Thus, if an effective daily dose of dexpramipexole is, for example, 150 milligrams or 300 milligrams, the initial dose of dexpramipexole may be 150 milligrams or 300 milligrams of dexpramipexole, and each daily dose thereafter may be 150 milligrams or 300 milligrams. Accordingly, the daily dose may be considered a "stable daily dose." For example, dexpramipexole treatment can be initiated at high levels without the need for titration. Therefore, a naïve subject who requires a dosage greater than about 150 milligrams or more, or about 300 milligrams or more, 400 milligrams or more, or about 500 milligrams or more, or about 600 milligrams or more dexpramipexole for treatment may be administered about 100 milligrams or more, about 125 milligrams or more, about 150 milligrams or more, 300 milligrams or more, 400 milligrams or more, 500 milligrams or more, or 600 milligrams or more of dexpramipexole during the first treatment without triggering the onset of adverse effects, as would be expected if pramipexole was administered at its terminal level during an initial treatment. Accordingly, embodiments of the various methods are directed to a method of treating a subject with ALS including administering an effective amount of dexpramipexole without titration. In certain embodiments, the effective amount may be about 100 milligrams or more, about 125 milligrams or more, about 150 milligrams or more, 300 milligrams or more, 400 milligrams or more, 500 milligrams or more, or 600 milligrams or more daily, and in some embodiments, the effective amount may be about 300 milligrams or more daily. In particular embodiments, the effective amount may be administered in separate equal doses twice daily. In each of the method embodiments described herein, any of the doses of dexpramipexole and/or any of the dosing regimens of dexpramipexole described herein may be used in such methods and continued administration of such doses may be continued for any of the described periods of time.

Embodiments of the various methods are also directed to a dosage regimen for administering dexpramipexole. For example, in some embodiments, the dosage regimen may include an initial dose dexpramipexole in one or more unit doses, then a plurality of daily doses having an equal amount of dexpramipexole as the initial dose in one or more unit doses. Such embodiments are not limited by the amount of the initial dose and daily doses. For example, in particular embodiments, the initial dose and each of the plurality of daily doses may be from about 50 milligrams to about 300 milligrams, or about 400 milligrams, or about 500 milligrams, or about 600 milligrams of dexpramipexole. In other embodiments, the initial dose and each of the plurality of daily doses may be from about 100 milligrams or more to about 300 milligrams, or about 400 milligrams, or about 500 milligrams, or about 600 milligrams of dexpramipexole, and in still other embodiments, the initial dose and each of the plurality of daily doses may be about 300 milligrams or more, about 400 milligrams or more, about 500 milligrams or more, or about 600 milligrams or more of dexpramipexole. In some embodiments, the one or more unit doses of the dosage regimen may be one to five unit doses, and in such embodiments, each of the one or more unit doses may be substantially equal. In other embodiments, each unit dose of the dosage regimen may be a solid unit dose. In each of the method embodiments described herein, any of the dosage regimens for dexpramipexole described herein may be used in any of the methods, and the dosing regimens may be carried out using any of the compositions or any combination thereof described herein.

In particular embodiments of the various methods, dexpramipexole may be administered to ALS subjects, and in such embodiments, the improvements observed in ALS subjects treated with dexpramipexole may be significantly better than conventional treatments such as, for example, treatments with riluzole. In some embodiments, the improvement may be signified by greater than 20% increase in ALSFRS-R score, when compared to baseline scores taken before treatment, and in other embodiments, this improvement may be manifested in a greater than 30% increase in ALSFRS-R score. In certain embodiments, the improvement in ALSFRS-R score may become apparent in less than 9 months, and in some embodiments, less than six, three, or one months. Riluzole, the only approved treatment for ALS, has not demonstrated any effect on ALSFRS-R score even after prolonged treatment. The majority of clinicians and clinical researchers believe that a therapy that results in a change of 20% or greater in slope of ALSFRS-R score is clinically meaningful. Therefore, the rate of improvement observed during dexpramipexole treatment is considerably and surprisingly better than that of other ALS treatments or no treatment based on ALSFRS-R score.

In various embodiments of the various methods, dexpramipexole may be administered for the treatment of ALS without incurring adverse events associated with, for example, riluzole, and the current standard of pharmacological intervention for ALS. For example, the overall rates of adverse events may be higher among subjects receiving riluzole concomitant with dexpramipexole or in conjunction with placebo. Headaches, for example, were reported by four times as many subjects receiving riluzole as those not receiving riluzole.

In some embodiments of the various methods, dexpramipexole may be administered to improve the general health of individuals having a neurological disease, and in other embodiments, dexpramipexole may be administered to alleviate one or more specific symptoms. For example, in particular embodiments, dexpramipexole may be administered to ALS subjects to improve symptoms associated with for example, loss of fine motor, loss of speech, and difficulty swallowing or a combination thereof. Without wishing to be bound by theory, in such embodiments, improvements in fine motor and speech and swallowing related symptoms may become apparent in a shorter period of time following the initiation of dexpramipexole treatment than, for instance, improvements in large motor function and pulmonary related symptoms. Thus, while improvements in large motor function and pulmonary related symptoms may be observed after treatment with dexpramipexole, in some embodiments, dexpramipexole may be administered to alleviate fine motor and speech and swallowing related symptoms more immediately than other ALS symptoms. In certain embodiments, ALS subjects treated with dexpramipexole may have an increased time before a feeding tube must be employed because such subjects may retain the ability to masticate and swallow food stuffs under their own power.

In other embodiments of the various methods, dexpramipexole may be administered to slow the rate of decline of a subject exhibiting symptoms of a neurological disease and/or to reduce mortality in such subjects. In such embodiments, populations of subjects diagnosed with a neurological disease such as, for example, ALS, may exhibit an increased time to death, an increased survival rate, and/or a decreased frequency of death as a result of treatment with dexpramipexole. Moreover, even in subjects who succumb to ALS or another neurological disease treated with dexpramipexole, dexpramipexole treatment may improve the quality of life for such subjects up to death.

The foregoing methods may comprising administering dexpramipexole on a dosing regimen to achieve a dose dependent, steady state $AUC_{0-12}$ (h×ng/mL) ranging from 836±234 to 2803±1635 to 6004±2700 at daily doses of 50 milligrams, 150 milligrams, and 300 milligrams, respectively, when administered in two equal doses twice daily.

In further embodiments of the various methods, dexpramipexole treatment may be carried out in combination with other forms of treatment. In some embodiments, such combination therapy may produce synergistic effects, such that the effect of dexpramipexole is augmented wherein one or more symptoms show a dramatic improvement over pre-treatment levels. For example, in certain embodiments, dexpramipexole treatment may be carried out in combination with (simultaneously or concurrently) with riluzole without adverse effects or reduced symptom relief. In other embodiments, dexpramipexole may be administered in combination with (simultaneously or concurrently) an additional form of treatment including, but not limited, those set forth in U.S. patent application Ser. No. 13/059,713 filed Apr. 19, 2011, which is hereby incorporated by reference in their entirety.

In some embodiments of the various methods, the pharmaceutical composition of dexpramipexole may achieve the effects described above by eliciting a neuroprotective, anti-oxidative, anti-apoptotic, or other beneficial cellular effects or combination of effects without the side-effects associated with dopaminergic agonists commonly used to treat neurodegenerative diseases. Without wishing to be bound by theory, the ability to deliver clinically effective doses of dexpramipexole without dose limiting side effects may be made possible by: (i) the synthesis of dexpramipexole that is pure within limits of the detection; and (ii) that dexpramipexole possesses a substantially lower affinity for dopamine receptors than its enantiomer, pramipexole. Further details regarding the molecular basis for dexpramipexole neuroprotective, anti-oxidative, anti-apoptotic, or other beneficial cellular effects or combination of effects, including a comparison of the activity of dexpramipexole versus pramipexole can be found in U.S. application Ser. No. 11/957,157, which is hereby incorporated by reference in its entirety.

Various embodiments of the various methods include methods for treating a neurodegenerative disease by administering a therapeutically effective amount of dexpramipexole such as, for example, about 100 milligrams or more, about 125 milligrams or more, about 150 milligrams, or more or about 300 milligrams or more. In accordance with such embodiments, dexpramipexole may be formulated as a pharmaceutical or therapeutic composition by combining with one or more pharmaceutically acceptable carriers. In some embodiments, such pharmaceutical or therapeutic compositions may be formulated in tablet or capsule form for use in oral administration routes. The compositions and amounts of non-active ingredients in such a formulation may depend on the amount of the active ingredient, and on the size and shape of the tablet or capsule. Such parameters may be readily appreciated and understood by one of skill in the art.

In certain embodiments of the various methods, the amount of pramipexole, (6S)-2-amino-4,5,6,7-tetrahydro-6-(propylamino)benzothiazole, remaining in the chirally pure dexpramipexole may be an amount not exceeding about 1.0 milligram, and in some embodiments, the amount of pramipexole may be an amount not exceeding about 0.75 milligrams, about 0.5 milligrams, about 0.25 milligrams, or about 0.125 milligrams. In particular embodiments, the amount of pramipexole in chirally pure dexpramipexole may be less than about 0.125 milligrams. Therefore, the amount of pramipexole that may be administered in pharmaceutical compositions containing the chirally pure dexpramipexole of various embodiments may be less than 1.0 milligrams per day, less than 0.5 milligrams per day, and in certain embodiments, less than 0.125 milligrams per day. Without wishing to be bound by theory, the amount of pramipexole in chirally pure dexpramipexole may be a non-effective dose such that any pramipexole in such compositions does not elicit a noticeable effect on subjects who are administered the pharmaceutical compositions of the various methods. For example, a 300 milligrams per day dose of dexpramipexole administered to a subject as a single unit dose of about 99.8% chirally pure dexpramipexole may contain a non-effective dose amount of pramipexole less than 1.0 milligrams per day, a 300 milligrams per day dose of about 99.9% chirally pure dexpramipexole may contain a non-effective dose amount of pramipexole less than 0.5 milligrams per day, and a 300 milligrams per day dose of about 99.98% dexpramipexole may contain a non-effective dose pramipexole of less than 0.125 mg/day.

Chirally pure dexpramipexole may be prepared or converted to a pharmaceutically acceptable salt of dexpramipexole. For example, in some embodiments, dexpramipexole may be formulated as (6R)-2-amino-4,5,6,7-tetrahydro-6-(propylamino)benzothiazole dihydrochloride, which is a pharmaceutically acceptable salt and may improve solubility of dexpramipexole in water. The conversion of (6R)-2-amino-4,5,6,7-tetrahydro-6-(propylamino)benzothiazole to a pharmaceutically acceptable salt may be accomplished by any method readily appreciated and understood by one of skill in the art. For example, (6R)-2-amino-4,5,6,7-tetrahydro-6-(propylamino)benzothiazole dihydrochloride may be prepared by a one-step method in which (6R)-2-amino-4,5,6,7-tetrahydro-6-(propylamino)benzothiazole or (6R)-2-amino-4,5,6,7-tetrahydro-6-(propylamino)benzothiazole salt is reacted with concentrated HCl in an organic solvent such as, for example, an alcohol, at a reduced temperature range of, for example, from about 0° C. to about 5° C. An organic solvent, such as methyl tert-butyl ether, may then be added, and the reaction may be stirred for about one hour. The (6R)-2-amino-4,5,6,7-tetrahydro-6-(propylamino)benzothiazole dihydrochloride produced may be recovered from the reaction mixture by filtering, washing with an alcohol, and vacuum drying.

The amount of dexpramipexole in such pharmaceutically acceptable compositions suitable for oral administration may vary. For example, in some embodiments, the amount of dexpramipexole in such compositions may range from about 25 milligrams to about 1000 milligrams, about 50 milligrams to about 1000 milligrams, from about 100 milligrams to about 1000 milligrams, from about 125 milligrams to about 1000 milligrams, from about 150 milligrams to about 1000 milligrams, from about 300 milligrams to about 1000 milligrams, from about 500 milligrams to about 1000 milligrams, from about 600 milligrams to about 1000 milligrams, and in certain embodiments, the amount of dexpramipexole may be from about 60 milligrams to about 300 milligrams. Each of the compositions embodied herein may be used in any of the methods or dosage regimen described herein.

In various embodiments of the various methods, the daily dosage of dexpramipexole may be administered as a single daily dose, or may be divided into two or more doses of equal or unequal amount administered throughout the day. For example, in some embodiments, dexpramipexole may be administered in doses of about 100 milligrams or more, about 125 milligrams or more, about 150 milligrams or more, 300 milligrams or more, 500 milligrams or more, or 600 milligrams or more. Dexpramipexole may be administered in one to five doses each containing an equal amount of dexpramipexole, and in other embodiments, dexpramipexole may be administered in two or three doses throughout the day in doses of about 100 milligrams or more, about 125 milligrams or more, about 150 milligrams or more, 300 milligrams or more, 500 milligrams or more, or 600 milligrams or more. In still other embodiments, dexpramipexole may be administered in two or three doses throughout the day in doses about 100 milligrams or more, about 125 milligrams or more, about 150 milligrams or more, 300 milligrams or more, 500 milligrams or more, or 600 milligrams or more, wherein one dose contains a higher concentration of dexpramipexole. For example, one dose of a 300 mg dexpramipexole regimen may contain 100 milligrams of dexpramipexole and a second dose administered at a different time during the day may contain 200 milligrams of dexpramipexole. The daily doses may be used in any of the methods or dosage regimen described herein.

The pharmaceutical or therapeutic compositions of the various methods may be prepared, packaged, sold in bulk, as a single unit dose, or as multiple unit doses, and can be administered in the conventional manner by any route where they are active. For example, the compositions may be administered orally, opthalmically, intravenously, intramuscularly, intra-arterially, intramedullary, intrathecally, intraventricularly, transdermally, subcutaneously, intraperitoneally, intravesicularly, intranasally, enterally, topically, sublingually, rectally by inhalation, by depot injections, or by implants or by use of vaginal creams, suppositories, pessaries, vaginal rings, rectal suppositories, intrauterine devices, and transdermal forms such as patches and creams. Specific modes of administration will depend on the indication. The selection of the specific route of administration and the dose regimen may be adjusted or titrated by the clinician according to known methods in order to obtain the optimal clinical response. All of the methods described herein may be carried out by administering dexpramipexole by any such route for administration described herein. Additionally, dexpramipexole may be delivered by using any such route of administration for the entire dosage regimen described herein.

Pharmaceutical formulations containing dexpramipexole in a solid dosage may include, but are not limited to, tablets, capsules, cachets, pellets, pills, powders, and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

For oral administration, the compounds can be formulated readily by combining these compounds with pharmaceutically acceptable carriers well known in the art. Such carriers enable the compounds of the various methods to be formulated as tablets, pills, dragees, capsules, liquids, gels, syrups, slurries, suspensions and the like, for oral ingestion by a subject to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations including, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

In some embodiments of the various methods, pharmaceutical compositions may be suitable for oral administration such as, for example, a solid oral dosage form or a capsule, and in certain embodiments, the composition may be a tablet. Such tablets may include any number of additional agents such as, for example, one or more binder, one or more lubricant, one or more diluent, one or more lubricant, one or more surface active agent, one or more dispersing agent, one or more colorant, and the like. Such tablets may be prepared by any method known in the art, for example, by compression or molding. Compressed tablets may be prepared by compressing in a suitable machine the ingredients of the composition in a free-flowing form such as a powder or granules, and molded tablets may be made by molding in a suitable machine a mixture of the powdered compound moistened with an inert liquid diluent. The tablets, of some embodiments, may be uncoated and, in other embodiments, they may be coated by known techniques.

In other embodiments of the various methods prepared for oral administration, the pharmaceutical compositions of the various methods may be provided in a dragee cores with suitable coatings. In such embodiments, dragee cores may be prepared suing concentrated sugar solutions, which may optionally contain gum arabic, talc, polyvinyl pyrrolidone, carbopol gel, polyethylene glycol, and/or titanium dioxide, lacquer solutions, and suitable organic solvents or solvent mixtures. In some embodiments, dyestuffs or pigments may be added to the tablets or dragee coatings for identification or to characterize different combinations of active compound doses. In yet other embodiments, pharmaceutical compositions including an effective amount of dexpramipexole prepared for oral administration may include, but are not limited to, push-fit capsules made of gelatin, as well as soft, sealed capsules made of gelatin and a plasticizer, such as glycerol or sorbitol. The push-fit capsules can contain the active ingredients in admixture with filler such as, for example, lactose, binders such as, for example, starches, and/or lubricants such as, for example, talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

In embodiments of the various methods in which the tablets and dragee cores are coated, the coatings may delay disintegration and absorption in the gastrointestinal tract and thereby provide a sustained action over a longer period. Additionally, such coatings may be adapted for releasing dexpramipexole in a predetermined pattern, for example, in order to achieve a controlled release formulation, or it may be adapted to not release the active compound until after passage of the stomach by including, for example, an enteric coating. Suitable coatings encompassed by such embodiments may include, but are not limited to, sugar coating, film coating, such as, for example, hydroxypropyl methylcellulose, methyl-cellulose, methyl hydroxyethylcellulose, hydroxypropylcellulose, carboxymethylcellulose, acrylate copolymers, polyethylene glycols, and/or polyvinylpyrrolidone, or an enteric coating, such as, for example, methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate may be incorporated into the coatings of some embodiments. In still other embodiments, solid tablet compositions may include a coating adapted to protect the composition from unwanted chemical changes, for example, to reduce chemical degradation prior to the release of the active drug substance.

Pharmaceutical compositions suitable for oral administration encompassed in embodiments of the various methods may include a therapeutically effective amount of dexpramipexole and a non-effective dose amount of pramipexole and may further include one or more diluents, one or more disintegrants, one or more lubricants, one or more pigments or colorants, one or more gelatins, one or more plasticizers, and the like. For example, in some embodiments, a tablet may include an effective amount of dexpramipexole, from about 20% to about 50% by weight of diluent in an amount, from about 10% to about 30% by weight of a second diluent, from about 2% to about 6% by weight of a disintegrant, and from about 0.01% to about 2% by weight of a lubricant, and in particular embodiments, such tablets may include an effective amount of dexpramipexole, from about 20% to about 50% by weight microcrystalline cellulose, about 10% to about 30% by weight mannitol, from about 2% to about 6% crospovidone or croscarmellose, and from about 0.01% to about 2% by weight magnesium stearate. In further embodiments, the pharmaceutical composition may include any amount or combination of microcrystalline cellulose, mannitol, sodium, crospovidone, croscarmellose magnesium stearate, or any combination thereof.

In such embodiments of the various methods, the pharmaceutical composition suitable for oral administration may include at least about 50 milligrams of dexpramipexole, and in some embodiments, such pharmaceutical compositions may include at least about 75 milligrams of dexpramipexole, at least about 100 milligrams of dexpramipexole, at least about 150 milligrams of dexpramipexole, at least about 200 milligrams of dexpramipexole, at least about 250 milligrams of dexpramipexole, at least about 300 milligrams of dexpramipexole, at least about 500 milligrams of dexpramipexole, at least about 600 milligrams of dexpramipexole, at least about 750 milligrams of dexpramipexole, or at least about 1000 milligrams of dexpramipexole. In certain embodiments, such pharmaceutical compositions suitable for oral administration prepared at any dosage described above may include a non-effective dose amount of pramipexole of less than about 0.125 milligrams.

In some embodiments of the various methods, the pharmaceutical compositions including dexpramipexole may be prepared as suspensions, solutions, or emulsions in oily or aqueous vehicles suitable for injection. In such embodiments, such liquid formulations may further include formulatory agents such as suspending, stabilizing, and/or dispersing agents formulated for parenteral administration. Such injectable formulations may be administered by any route, including but not limited to, for example, subcutaneous, intravenous, intramuscular, intra-arterial, bolus injection, or continuous infusion, and in embodiments in which injectable formulations are administered by continuous infusion, such infusion may be carried out for a period of about fifteen minutes to about twenty-four hours. In certain embodiments, formulations for injection can be presented in unit dosage form, such as, for example, in ampoules or in multi-dose containers, with an added preservative.

In other embodiments of the various methods, dexpramipexole may be formulated as a depot preparation, and such long acting formulations can be administered by implantation, such as, for example, subcutaneously or intramuscularly, or by intramuscular injection. Depot injections can be administered at about one to about six months or longer intervals. Thus, for example, the compounds can be formulated with suitable polymeric or hydrophobic materials, for example, as an emulsion in an acceptable oil, or with ion exchange resins, or as sparingly soluble derivatives, for example, as a sparingly soluble salt.

In still other embodiments, pharmaceutical compositions including dexpramipexole may be formulated for buccal or sublingual administration. In such embodiments, the pharmaceutical compositions may be prepared as chewable tablets, flash melts, or lozenges formulated in any conventional manner known in the art.

In yet other embodiments, pharmaceutical compositions including dexpramipexole may be formulated for administration by inhalation. In such embodiments, pharmaceutical compositions according to the various methods may be delivered in the form of an aerosol spray presentation from pressurized packs or a nebulizer with the use of a suitable propellant, such as, for example, dichlorodifluoromethane, trichlorofluoromethane, dichlorotetrafluoroethane, carbon dioxide, or other suitable gas. In the case of a pressurized aerosol pack, the dosage unit can be determined by providing a valve to deliver a metered amount. Capsules and cartridges of, for example, gelatin for use in an inhaler or insufflator can be formulated containing a powder mix of the compound and a suitable powder base such as lactose or starch.

In further embodiments, pharmaceutical compositions including dexpramipexole can be formulated in rectal compositions such as suppositories or retention enemas, for example, containing conventional suppository bases such as cocoa butter or other glycerides.

In some embodiments, pharmaceutical compositions including dexpramipexole may be formulated for transdermal administration. Such pharmaceutical compositions may be prepared, for example, to be applied to a plaster or applied by transdermal, therapeutic systems that are supplied to the subject. In other embodiments, pharmaceutical and therapeutic compositions including dexpramipexole for transdermal administration may include suitable solid or gel phase carriers or excipients such as, but not limited to, calcium carbonate, calcium phosphate, various sugars, starches, cellulose derivatives, gelatin, and polymers such as, for example, polyethylene glycols.

In some embodiments, pharmaceutical compositions including dexpramipexole may be administered alone as a single therapeutic agent. In other embodiments, pharmaceutical compositions including dexpramipexole may be administered in combination with one or more other active ingredients, such as, for example, adjuvants, protease inhibitors, or other compatible drugs or compounds where such combination is seen to be desirable or advantageous in achieving the desired effects of the methods described herein.

In contrast to many other studies, an embodiment of the various methods includes subjects with "possible ALS". Historically, the inclusion of subjects in clinical trials in ALS has been limited to those who meet laboratory-supported probable, probable, or definite ALS, either familial or sporadic, in accordance with the revised El Escorial criteria. When these criteria were applied to data obtained from the Irish ALS register, 43% of subjects with ALS would not have been eligible for clinical studies at the time of diagnosis and 10% of subjects remained ineligible at death. In these subjects, the median time from onset of symptoms to eligibility for trial participation was thirteen months. Expanding the subject inclusion criteria impacts enrollment. In addition, including subjects earlier in the disease process may enhance the potential to observe a response to treatments that are putatively neuroprotective. This is a valid way to capture subjects earlier in their disease progression.

Clinical studies are critical for establishing the safety and efficacy of potential treatments, as Phase II studies are generally smaller and designed to provide data supporting the safety and tolerability of a compound. An uncontrolled study of a compound without Phase III study results, particularly in a serious illness such as ALS, has the potential to cause untoward effects on subjects. Moreover, the interpretation of smaller studies, such as Phase II studies, and their use to determine whether or not to conduct larger studies must be carefully considered in any disease area. Studies are therefore critical to confirm any potential efficacy observed in smaller studies and for assessment of long-term safety.

Several compounds initially thought to be effective in ALS were used by individuals with ALS outside of studies because of the dearth of effective therapies. Early reports of a beneficial effect of lithium from a small exploratory study were not confirmed. In fact in one study more subjects who received lithium in combination with riluzole experienced an operationally defined "treatment failure" event (either a decrease of ≥6 points on the ALSFRS-R rating scale or death) than subjects who received placebo/riluzole. A small phase II study of talampanel also did not indicate statistically significant differences from placebo although trends in slowing ALSFRS-R decline and muscle strength were observed (Pascuzzi R M et al, 2010); talampanel subsequently failed to show any treatment effects in a larger Phase III study in ALS. In a phase III clinical study of minocycline for ALS, the rate of decline in the ALSFRS-R score was faster for subjects treated with minocycline than for subjects treated with placebo (−1.3 versus −1.04 units/month, [95% CI −0.44, −0.81], p=0.11) despite positive studies demonstrating the beneficial effects of minocycline in laboratory animals. Off-label use of the available compounds may have exposed subjects with ALS to possible detrimental effects. Off-label use also has the potential to impact clinical development and clinical trial conduct.

The embodiments for disease states, subject type, naïve vs. not naïve, daily dose amounts, no observable adverse effect level dose amounts, non-effective dose amounts, and chiral purities for the methods of the various methods, which are described herein separately for the sake of brevity, can be joined in any suitable combination or combinations.

Some embodiments include methods of identifying a subject that will likely respond to treatments described herein. In some embodiments, the subject will exhibit one or more of the following characteristics: definite ALS as defined by the El Escorial diagnosis criteria, amyotrophic lateral sclerosis symptom onset duration of less than about 18 months, limb-onset amyotrophic lateral sclerosis, concomitant riluzole administration, an ALSFRS-R score of greater than 36.0, a pre-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0beats per minute, a diastolic blood pressure of greater than 82.0 mmHg, a systolic blood pressure of less than or equal to 117.0 mmHg, a creatinine value of greater than 72.0 µmol/L, a phosphorous value of less than or equal to 1.090 µmol/L, a platelet count of less than or equal to 248.0 ×109 cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4mmol/L, a uric acid level of greater than 320.0µmol/L, a gamma-glutamyltransferase (GGT)level of greater than 37.0 U/L, a total bilirubin level of less than or equal to 6.0 µmol/L, a urine pH of less than or equal to 5.5, or any combination thereof. In some embodiments, the subject will have at least one of the above characteristics. In some embodiments, the subject will have more than one of the above characteristics. In embodiments, the method further comprises monitoring said subject for any clinical features associated with amyotrophic lateral sclerosis. In embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

EXAMPLE 1 EMPOWER

A study design addressed the assessment of both function and survival as a primary outcome, subject recruitment and retention, and the burden of clinical trial participation on recruiting subjects.

Figure 2:
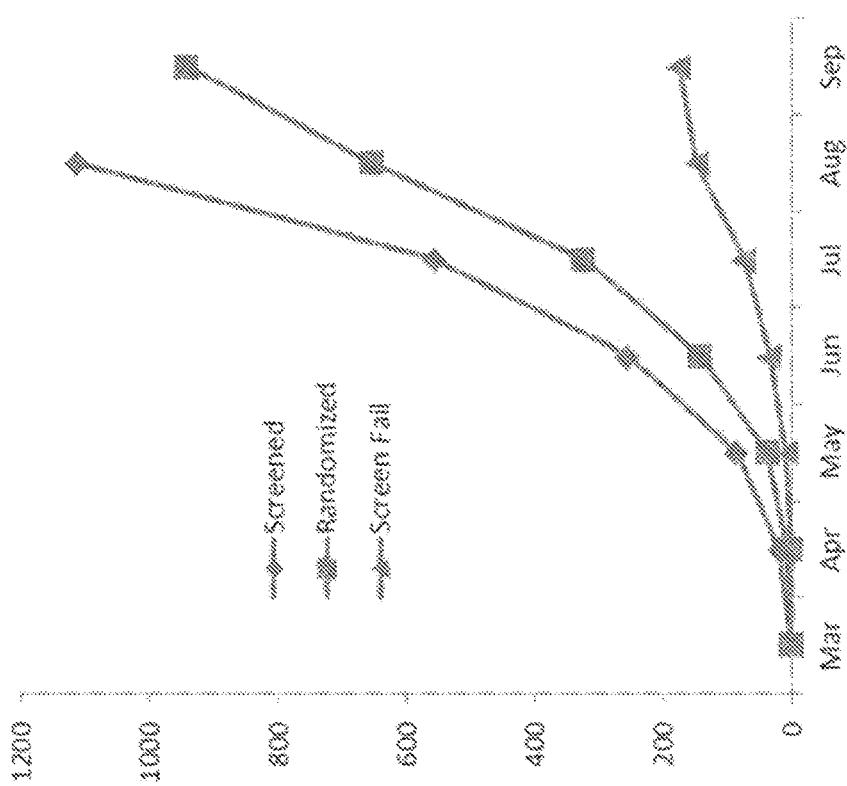
FIG. 2 shows recruitment rate in the clinical trial.

The embodiment is a multicenter, prospective, randomized, double-blind, placebo-controlled trial to determine the efficacy and safety of dexpramipexole. Eligible subjects were between 18-80 years of age with a clinical diagnosis of possible, laboratory-supported probable, probable, or definite ALS, either familial or sporadic, in accordance with the revised El Escorial criteria. Subjects were required to have had onset of first ALS symptoms ≤24 months before Day 1 and an upright vital capacity of ≥65% of predicted value for age, height, and gender at screening. Subjects not using riluzole for ≥30 days or those taking a stable dose for ≥60 days before Day 1 were allowed in the study. Riluzole-naïve subjects were also eligible, which allowed exploratory comparisons of the efficacy of dexpramipexole alone vs. dexpramipexole with concomitant riluzole treatment. Subjects had to be able to swallow oral medications on Day 1 (FIG. 1). Screening results in 175 failures reduced the number before the screening of 1118 subjects to 943 subjects (FIGS. 1 and 2).

Subjects

Subject characteristics in Example 1 were largely consistent with ALS studies using other investigational compounds, specifically, U.S. patent application Ser. No. 12/819,990, ("'990") incorporated in its entirety by reference herein, minocycline and glatiramer acetate (Table 1). Slightly more subjects in the first method used riluzole and had bulbar onset, compared with subjects in '990.

TABLE 1

Demographics, baseline characteristics of subjects in the instant study and other published studies

| Characteristic | Minocycline[a] | | Glatiramer acetate[a] | Dexpramipexole: '990 | Clinical Study |
| --- | --- | --- | --- | --- | --- |
| | Active n = 206 | PBO n = 206 | n = 366 | n = 102 | n = 943 |
| Age (mean) | 58.6 (11.8) | 57.7 (10.9) | 55.2 (9.6) | 57.0 (10.25) | 57.1 (11.29) |
| Males (%) | 69 | 64 | 61.5 | 64 | 64 |
| Baseline ALSFRS-R mean (SD) | 37.8 (5.17) | 37.9 (5.17) | 38.4 (5.3) | 38.1 (5.30) | 38.2 (5.45) |
| Symptom Duration (mean) | 16.3 (8.4) | 18.1 (9.5) | 20.4 (8.6) | 14.05 (5.69) | 15.26 (5.35) |
| Bulbar Onset (%) | 19 | 20 | 18.3 | 17 – 1 (bulbar + other) | 23 |
| Riluzole (%) | 67 | 66 | Not reported | 61 | 75 |

DEX = dexpramipexole;
PBO = placebo
[a]Minocycline (Gordon et al, 6 LANCET NEUROL. 1045-53 (2007) and glatiramer acetate (Meininger, 10 AMYOTROPH LATERAL SCLER. 378-83 (2009)

Subjects not receiving riluzole or those taking riluzole at a stable dose for ≥60 days before study start were eligible. Subjects in a randomized 1:1 ratio received oral 150 mg dexpramipexole or placebo twice daily for 12 to 18 months. Use of placebo was ethical because the safety and efficacy of dexpramipexole in ALS have not yet been conclusively demonstrated and concomitant treatment with riluzole is permitted if desired by the subject and if initiated prior to enrollment in the study.

The key exclusion criteria in the embodiment were: 1) presence of significant cognitive impairment, clinical dementia, or psychiatric illness; other neurodegenerative disease, such as, for example, Parkinson's disease or Alzheimer disease; 2) a clinically significant history of unstable/severe cardiac, oncologic, hepatic, or renal disease or other medically significant illness; 3) pre-existing pulmonary disorder not attributed to ALS; 4) a neutrophil count <1.96×10³/µL at screening or a documented history of neutropenia; 5) aspartate aminotransferase (AST) or alanine aminotransferase (ALT) levels >3.0×upper limit of normal; 6) creatinine clearance ≤50 mL/min; 7) previous exposure to dexpramipexole or other experimental agent (off-label use or investigational) ≤30 days prior to Day 1; 8) current use of pramipexole or other dopamine agonists.

Clinic visits and telephone calls/home visits may have occurred on alternating months. The primary efficacy analysis was a Combined Assessment of Function and Survival (CAFS), based on changes from baseline in the ALS Functional Rating Score-Revised (ALSFRS-R) scores or time to death using follow-up data through 12 months. Key secondary endpoints included time to death or respiratory insufficiency, such as combined endpoint: time to tracheostomy, or the use of non-invasive ventilation for greater than or equal to 22 hours per day for greater than or equal to ten consecutive day, or death), time to death, respiratory decline, (time to reach less than or equal to 50% of predicted upright slow vital capacity or death), changes in muscle strength quantified by hand-held dynamometry, and changes in ALS-related quality of life measured by the ALS Assessment Questionnaire (ALSAQ-5). Efficacy data was evaluated using 2-sided tests with α=0.05 for the primary and secondary endpoints. Adverse events and other safety indices were monitored throughout the study.

Double-blind treatment continued up to 18 months or until the last subject completed 12 months, whichever came first. This allowed the collection of maximum information on the effect of dexpramipexole on survival and safety. The operational conduct of the study included a managed recruitment process, a robust communication plan with study sites, and an actively involved study team that closely monitored study sites.

Nine hundred forty three (943) subjects were enrolled. Mean baseline ALSFRS-R score was 38.2±5.5, and mean symptom duration was 15.3±5.4 months; most subjects, about 75%, entered the study receiving concomitant riluzole.

Efficacy Assessments

The primary endpoint of the method of Example 2 was the Combined Assessment of Function and Survival (CAFS), a joint-rank test that is a valid statistical approach for analyzing functional outcomes adjusted for mortality. The CAFS ranks subjects' outcomes based on both time to death and change from baseline in ALSFRS-R score using follow-up data through 12 months. CAFS is predicated on the comparison of outcomes of each subject to all other subjects in the study. A higher rank is assigned to subjects who survive versus those who die, and the change from baseline in the ALSFRS-R is used to rank each survivor. A higher CAFS ranking indicates a better global clinical outcome. At the end of the trial, each subject's CAFS score was used to calculate average scores for each treatment group in order to evaluate the effect of dexpramipexole versus placebo on both function and survival.

Secondary and tertiary endpoints included evaluation of time to death or respiratory insufficiency, (combined endpoint: time to tracheostomy, or the use of non-invasive ventilation for ≥22 hours per day for ≥10 consecutive days, or death), time to death, respiratory decline (time to reach ≤50% of predicted upright slow vital capacity or death), muscle strength, quality of life, population pharmacokinetics, and safety (Table 2). Quality of life was assessed using the Amyotrophic Lateral Sclerosis Assessment Questionnaire (5-item Form) (ALSAQ-5) and the change in the Short Form 36 (SF-36) total score. The change in the Caregiver Burden Inventory (CBI) total score is used to evaluate potential impact on caregiver burden. Safety assessments included physical examinations, clinical laboratory evaluations, vital signs, and adverse/serious adverse event monitoring. Because a small number of cases of reversible neutropenia were observed in a previous study, monthly blood draws (in clinic alternating with home visits) including absolute neutrophil counts was obtained for all subjects.

TABLE 2

EMPOWER Study Endpoints

Primary Efficacy Endpoint (at 12 months)

CAFS is a joint rank endpoint: based on change from baseline in ALSFRS-R score and time to death using follow-up data through 12 months Secondary and Tertiary Endpoints (at 18 months)
Efficacy Time to death or respiratory insufficiency
Time to death
Respiratory decline: time to 50% of predicted upright VC or death; decline
in predicted SVC and SNIP
Change in MSM, determined by overall mega score for HHD
Ambulatory decline: time to recommended wheelchair use for out-of-home ambulation or death
Time to death or death equivalence (tracheostomy or permanent assisted ventilation, defined as use of NIV for ≥22 hours per day for ≥10 days), using all available follow-up data
Time to recommended gastrostomy tube placement or death
Time to treatment failure, calculated from randomization to date of death or decline in ALSFRS-R Population Pharmacokinetics Final parameters dependent on the population PK model
Relationship between population PK parameters and potential determinant covariates (e.g., age, gender, race, co-medication, renal function)
Changes from baseline in efficacy endpoints (e.g., ALSFRS-R)

Safety (assessment visits)

Monitor AEs and SAEs (throughout study duration)
Vital signs: SBP/DBP, RR, HR, temperature (screening, BL, Week 2, Months 2, 4, 6, 8, 10, 12, 14, 16, 18 and EOS/ET)
Clinical laboratory assessments: hematology, blood chemistry, urinalysis (every clinic visit)
Physical examination (screening, BL, Months 2, 6, 12, 18 and EOS/ET)
12-lead ECGs (screening, BL, Week 2, Months 6, 12, 18 and EOS/ET)
Body weight (screening, BL, Week 2, Months 2, 4, 6, 8, 10, 12, 14, 16, 18 and EOS/ET)

Quality of life (assessment visits)

ALS Assessment Questionnaire, 5-Item Form (ALSAQ-5) (BL, Months 6, 12, 18 and EOS/ET)
European Quality of Life - 5 Dimensions (EQ-5D) (BL, Months 6, 12, 18 and EOS/ET)

TABLE 2-continued

EMPOWER Study Endpoints

Caregiver Burden Inventory (CBI) (BL, Months 6, 12, 18 and EOS/ET)
Health Resource Use Questionnaire (BL, Months 6, 12, 18 and EOS/ET)

Figure 3:
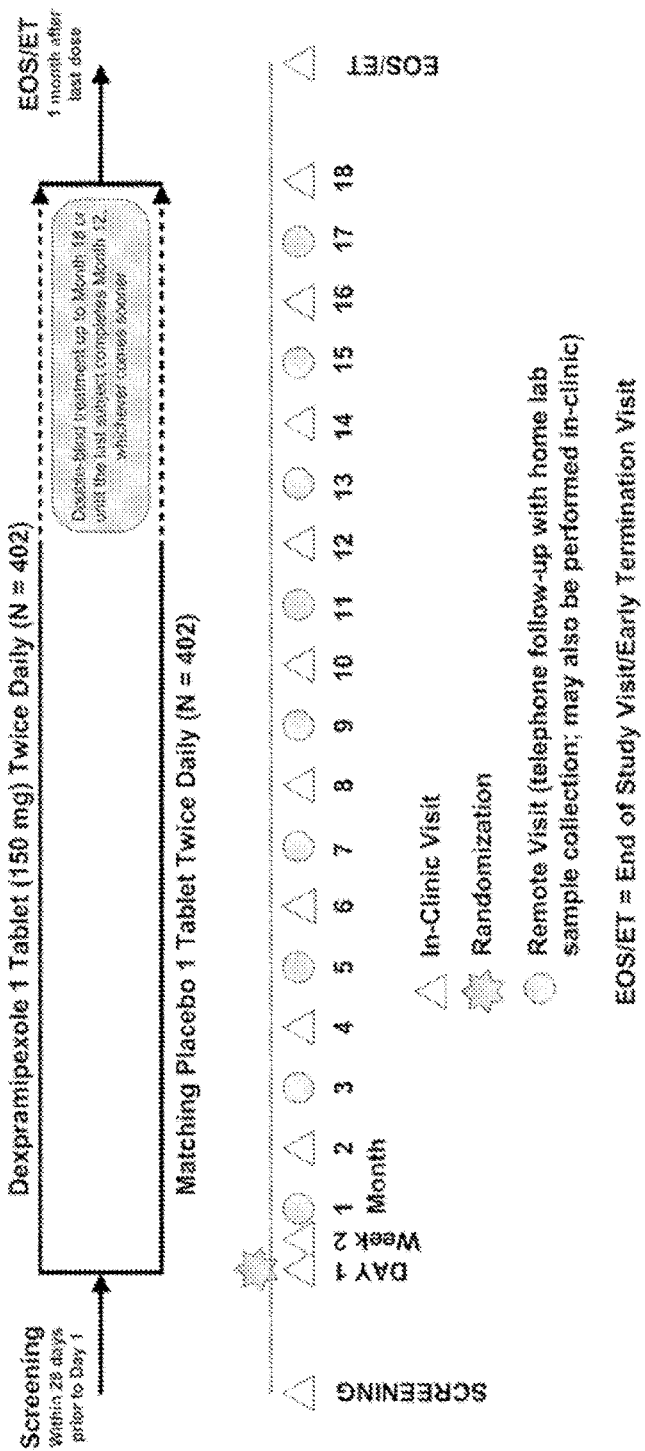
FIG. 3 depicts a study schedule of the clinical trial.

CAFS = combined assessment of function and survival;
AE = adverse event;
BL = baseline;
DBP = diastolic blood pressure;
ECG = electrocardiogram;
EOS = end of study;
ET = early termination;
HHD = hand-held dynamometry;
HR = heart rate;
MSM = muscle strength measurement;
NIV = non-invasive ventilation;
RR = respiratory rate;
SAE = serious adverse event;
SNIP = sniff nasal inspiratory pressure;
SVC = slow vital capacity;
SBP = systolic blood pressure;
VC = vital capacity Study Schedule A 4-week screening period preceded randomization (FIG. 3). Study assessments were performed at baseline (Day 1), Week 2, and subsequently every other month until Month 18. The end of study or end of treatment visit was conducted in the clinic if possible. Alternate month visits, i.e. months 1, 3, 5, 7, 9, 11, 13, 15, and 17, were conducted via remote telephone and/or home visits. Subjects who completed the study (between 12 and 18 months, depending on enrolment date) were offered an open-label extension treatment study.

To promote retention and accommodate subjects with disabling disease progression, subjects who were homebound or under hospice care were followed through home visits and telephone contacts, during which a limited set of data was collected, such as, for example, laboratory tests, ALSFRS-R score, and adverse event reporting. This type of accommodation for subjects in the study is different from ALS studies.

Statistical Analysis

The study is able to independently evaluate a potential benefit of dexpramipexole versus placebo on ALSFRS-R scores, survival, and CAFS ranking. Analysis of the primary endpoint will be based on the efficacy population, defined as all randomized subjects who received ≥1 dose of study drug and with ≥1 post-dosing efficacy evaluation or who died during the study. Analysis of secondary and tertiary endpoints will be done using the intent-to-treat population (ITT), defined as all randomized subjects who received ≥1 dose of study drug. All efficacy comparisons will be 2-sided statistical tests with $\alpha=0.05$ for the primary endpoint, CAFS ranking, and secondary endpoints.

For the survival analysis, the study was powered such that it would have an 80% probability of detecting a 37% difference between dexpramipexole and placebo, based on a sample size of 402 subjects per treatment group. A hazard ratio reduction of about 37% represents a clinically meaningful survival benefit. For about 90% power to detect a mean difference between groups of about 2.13 on the ALSFRS-R score at 12 months, it was estimated that a sample size of about 402 subjects per treatment group is required, with about a 20% drop-out rate. This dropout rate was derived by an assessment of the dropout rates of several large ALS trials conducted since 1996 which indicated that the placebo drop-out rate was below 20% annually. Discontinuation rates in pivotal trials have historically been high for ALS treatment. See for example FIG. 1 of Aggarwal et al., "ALS Drug Development: Reflections from the Past and a Way Forward", 5 NEUROTHERAPEUTICS, 516-527 (2008), which is incorporated in its entirety for any purpose.

The study power calculation used a 2-sided Wilcoxon test with $\alpha=0.05$ and standard deviation ($\sigma$) of about 8.1. The standard deviation ($\sigma$) was based on results of a study from U.S. patent application Ser. No. 12/819,990 and published studies of minocycline and glatiramer acetate, chosen as being more reflective of the current care of ALS subjects and their associated disease progression rates than older studies. As the number of subjects (943) enrolled exceeds the planned sample size (804) for 90% power, the study adequately will assess the a priori endpoints.

To understand drivers for the effect on CAFS rankings, evaluations of ALSFRS-R scores and time to death will be conducted as component analyses for CAFS rankings. The mixed effects repeated measures model was performed on the change from baseline in ALSFRS-R functional scores using data through 12 months. The mixed-effects slope model is not the primary analysis method, as the mixed-effects slope model assumes linearity in the decline of function over time, which may or may be observed in a 12-18 month study, and moreover, assumes that all discontinuations are random and non-informative, which is not the case for deaths. However, the mixed-effects slope model will be used to assess the slope of decline in determining ALSFRS-R scores as a sensitivity analysis.

Figure 4:
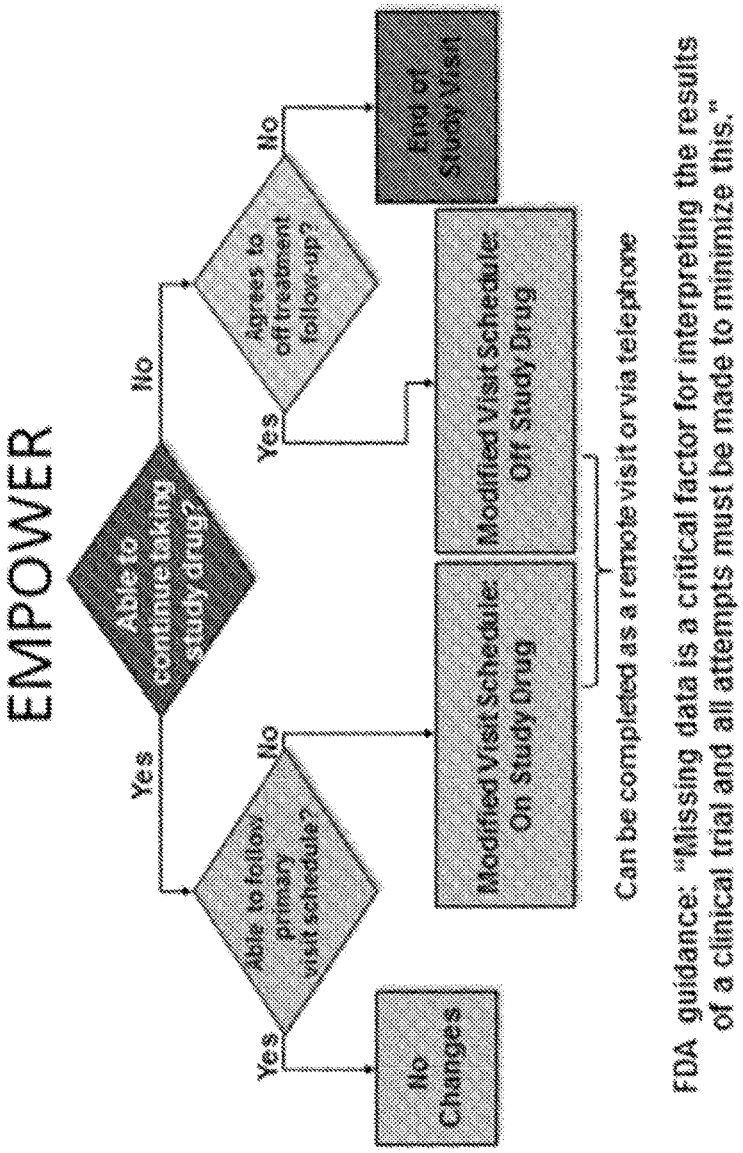
FIG. 4 shows a flow chart of maximizing subject retention in the clinical trial.

A number of measures were put into place to maximize recruitment and retention of subjects. A large number of centers were included to allow more subjects to be enrolled and subject communities were informed about the study via webinars, dedicated websites, hotlines, and subject advocacy groups. The treatment protocol also allowed the use of home nurses and data collection as part of home visits or telephone calls if subjects became unable to travel during the study due to disabling disease progression (FIG. 4). Subjects and caregivers are kept regularly informed of the progress of the study through newsletters. In addition, at each investigator meeting, tools for subject retention are re-evaluated and modified as needed.

Clinical status was assessed by administration of (1) the ALSFRS-R to assess functional status; (2) vital capacity (VC) to assess pulmonary function; and (3) the McGill single-item scale (SIS) to assess general quality-of-life. Plasma and CSF samples were collected to assess potential drug-related changes in potential surrogate markers of motor neuron stress and damage, such as levels of cystatin C.

Analysis of the ALSFRS-R score subdomain results indicated that particular behaviors associated with each subdomain were improved as a result of dexpramipexole administration. Behaviors associated with fine motor skills showed dose dependent improvement over baseline in subjects who were treated with 300 mg/day of dexpramipexole. Subjects who received 300 mg/day of dexpramipexole exhibited less reduction in cutting food and dressing and hygiene scores than subjects who received placebo. Behaviors associated with bulbar function also exhibited a less dramatic decline in ALSFRS-R score over baseline in those subjects who received 300 mg/day of dexpramipexole. Of the behaviors quantified, swallowing scores appeared to have been maintained better than other behaviors. Scores associated with gross motor and respiratory behaviors followed similar trends. The improvement in individual behaviors associated with the subdomains was generally improved over placebo. Thus, a slower decline in ALSFRS-R score was exhibited in subjects after placebo washout and re-randomization.

Dexpramipexole is safe and was well-tolerated in ALS subjects over 18 months of treatment at total daily doses 300 mg compared with placebo. Furthermore, meaningful differences were also observed in both the mean and median changes from baseline to endpoint in ALSFRS-R total scores between the placebo and 300 mg groups. An exploratory analysis with covariate adjustment yielded a significant improvement in ALSFRS-R score change at Month 18 for the 300 mg group as compared to the placebo group. According to a recent survey of ALS specialty physicians, a decline of 25% in ALSFRS-R score is considered to be clinically significant, while a reduction of 50% is considered to be clinically very significant. The improvements in functional decline observed for the 300 mg group compared to placebo, therefore, are at or near levels that are considered by ALS specialty physicians to be a clinically very significant treatment effect. Results of this study demonstrate that dexpramipexole is safe and well-tolerated in subjects with ALS at doses up to 300 mg per day, and further suggest that dexpramipexole may have the potential to slow functional decline in ALS as measured by the ALSFRS-R score.

Throughout the study, subjects were monitored closely for the observation of unexpected or clinically significant safety or tolerability events. Safety evaluations included physical examination, neurological examination, vital signs, 12-lead ECG, laboratory evaluations, lithium screening, and monitoring of adverse events. Vital signs, including systolic and diastolic blood pressure, respiratory rate, pulse rate, and temperature, were measured after the subject had rested for 5 minutes. The following guidelines were used to grade the intensity of an AE:

| | |
|---|---|
| Mild | The event is of little concern to the subject and/or of no clinical significance. The event is not expected to have any effect on the subject's health or well-being. |
| Moderate | The subject has enough discomfort to cause interference with or change in usual activities. The event is of some concern to the subject's health or well-being. The event may have required medical intervention. |
| Severe | The subject is incapacitated and unable to work or participate in many or all usual activities. The event is of definite concern to the subject or posed substantial risk to the subject's health or well-being. The event is likely to require medical intervention or close follow-up. |

Interviews for activity equivalents (AEs) were conducted often throughout the course of the study. At a minimum, such interviews occurred during each subject visit, including telephone contacts. The interview for AEs were conducted early during a given subject interaction. This was especially important when the ALSFRS-R score was being administered during the same visit. During such visits, the activity equivalents interview was conducted prior to administration of the ALSFRS-R score.

The ALSFRS-R score, VC, and McGill QoL-SIS scores were summarized by treatment group with the rate of change estimate derived from a linear mixed-effects model. Linear decline of the ALSFRS-R score over time has been shown previously. If the linearity assumption did not hold, that of a quadratic term with a p-value <0.05, a repeated measures mixed-effect model was used. A mixed-model analysis was used to fit a model that included time, treatment group, and the interaction between time and treatment group simultaneously. The estimated coefficient of time, the slope, or rate of change, for each treatment group was used to test for differences between the treatment groups. Coefficient of time estimate along with its standard error was reported.

An additional sensitivity analysis was performed, based on a rank score derived from a joint ranking of time to mortality and functional decline for surviving subjects, that of the change from baseline in ALSFRS-R score using the methodology proposed by Finkelstein and Schoenfeld. A subject's score/ranking was calculated by comparing each subject to every other subject in the trial, setting a score of +1 if the outcome was better than the subject being compared, −1 if worse, and 0 if tied. The subject's score/ranking was then calculated by summing up the subject's comparison to all the other subjects in the study. For this comparison, a subject who died earlier than the comparator subject was given a comparison score of −1; if two subjects completed the study, their comparison score was based on a comparison of relative changes in their ALSFRS-R score values at the end of the study; if a subject discontinued early, the subject's comparison to each other subject was based on the comparison of their relative change in their ALSFRS-R score at the latest time point at which both subjects had an ALSFRS-R value. This resulted in subjects who experienced death getting the worst scores/ranking and being ranked according to the time of death; subjects who survived were ranked above those subjects who experienced death, and in general were ranked according to their endpoint ALSFRS-R change value, with special handling to rank early discontinuations as described above.

The population PK and safety results from the clinical studies of the embodiment supported continued development of dexpramipexole as a treatment of ALS and potentially other neurodegenerative diseases.

Results

Figure 7:
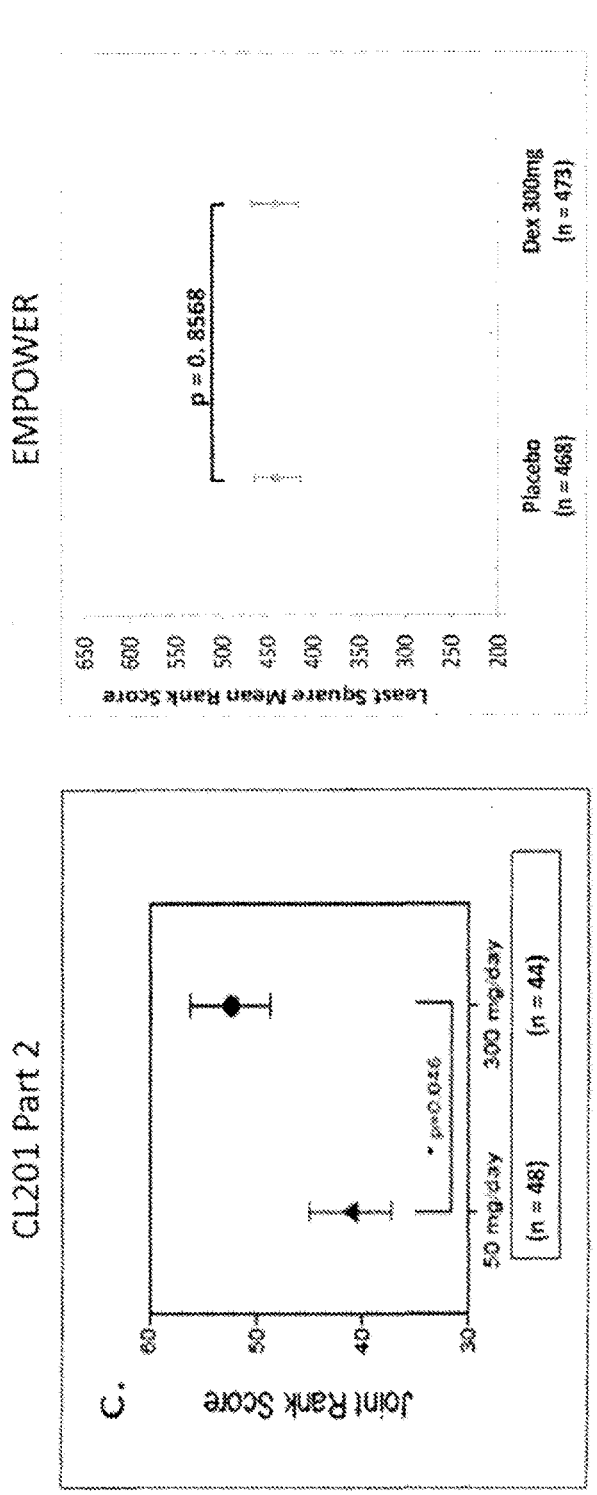
Figure 9:
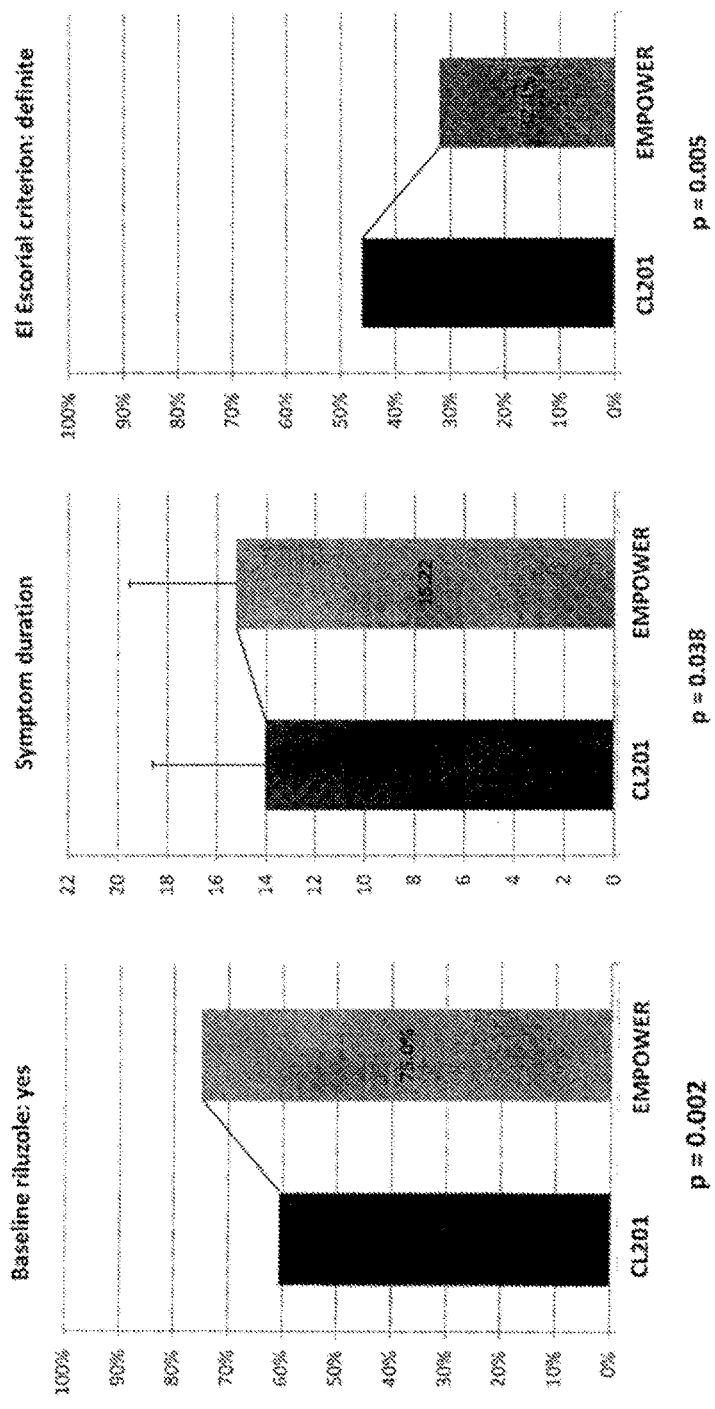
Figure 10:
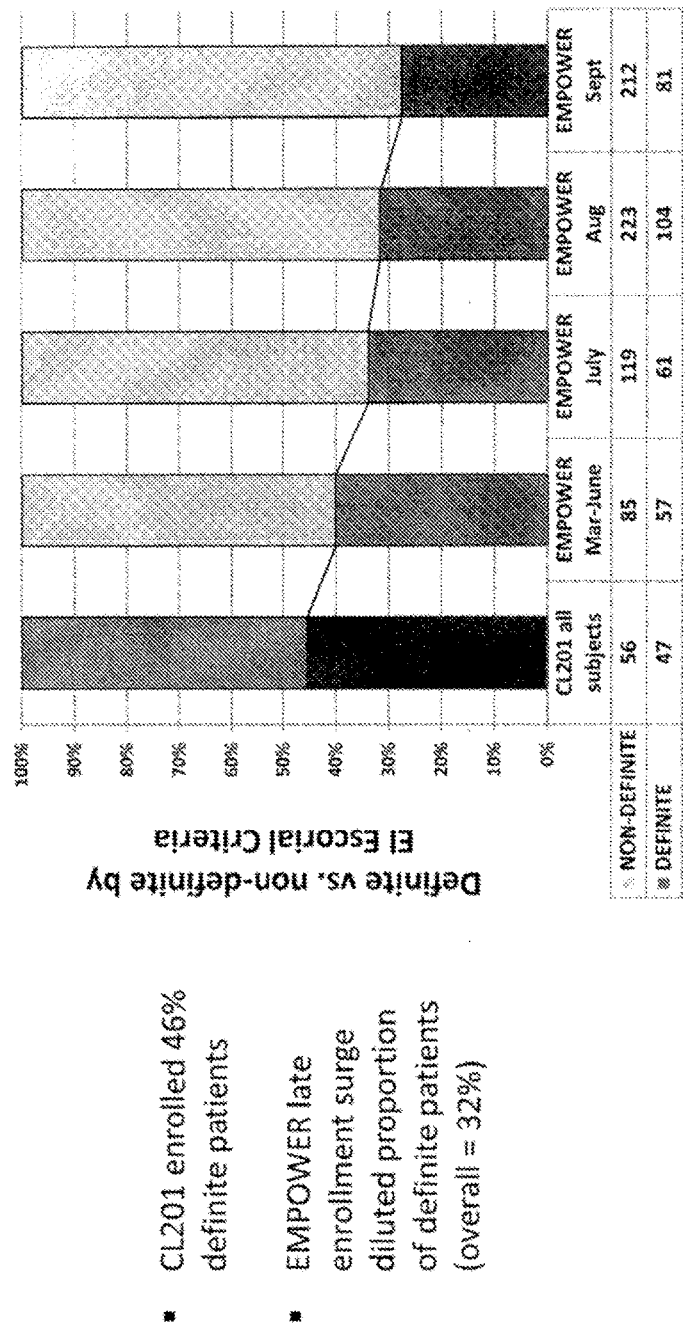
Figure 13:
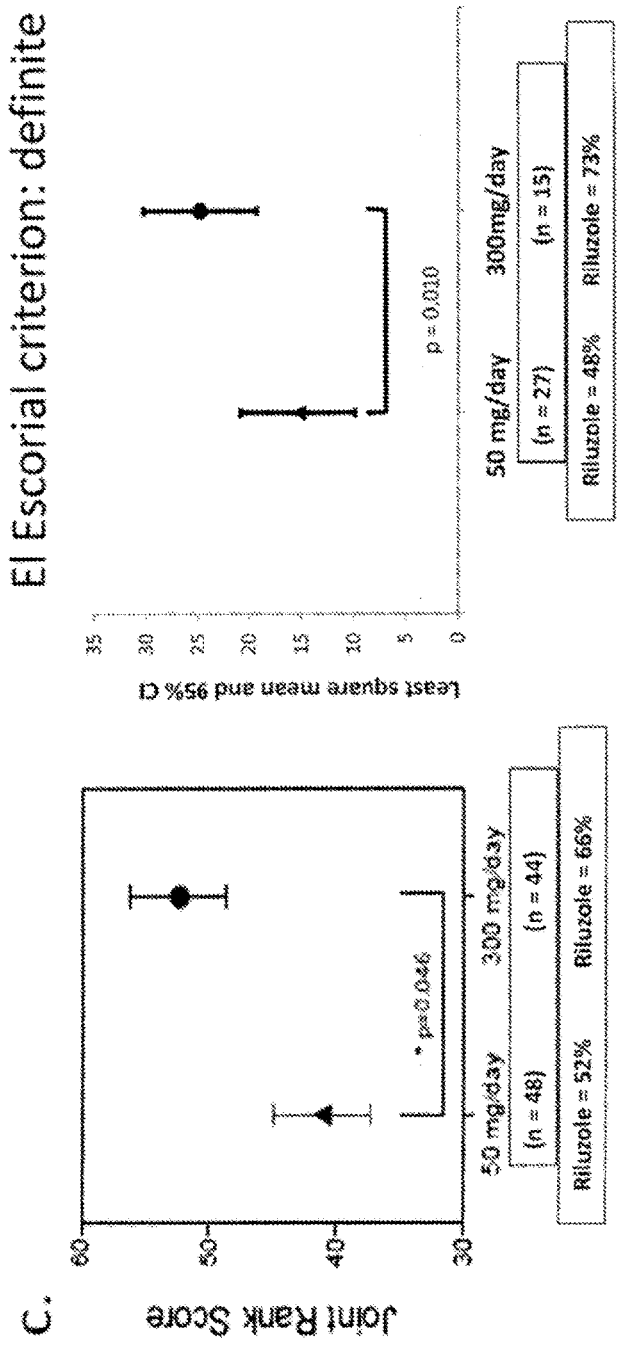
Figure 16:
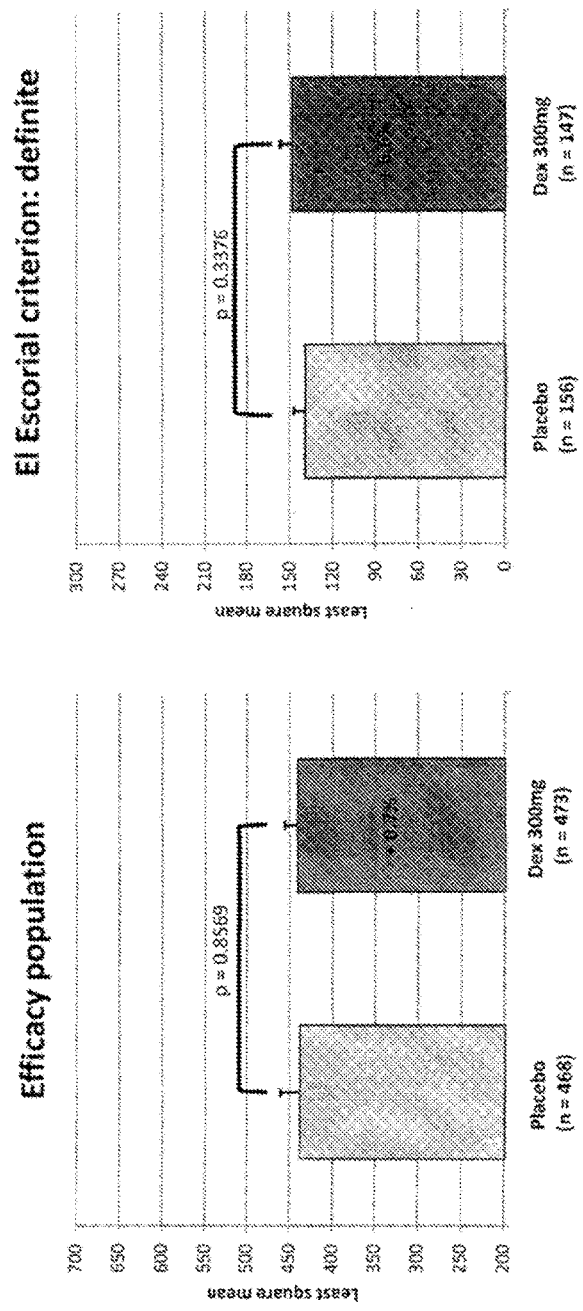
Figure 17:
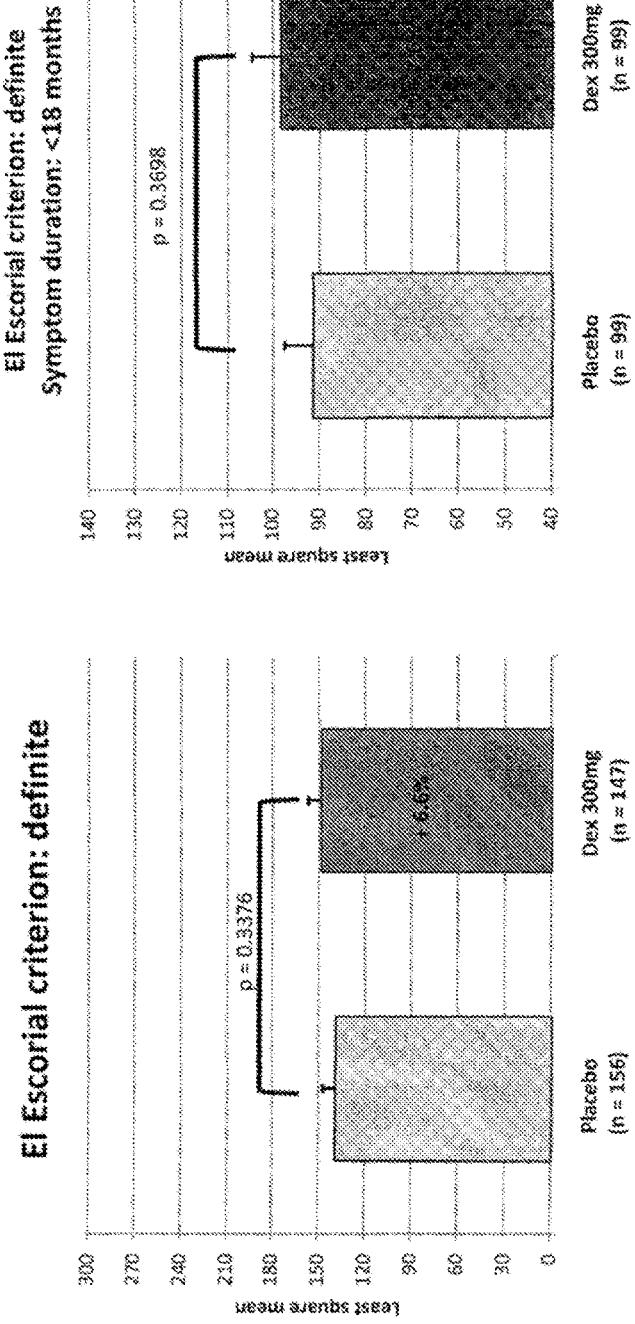
Figure 18:
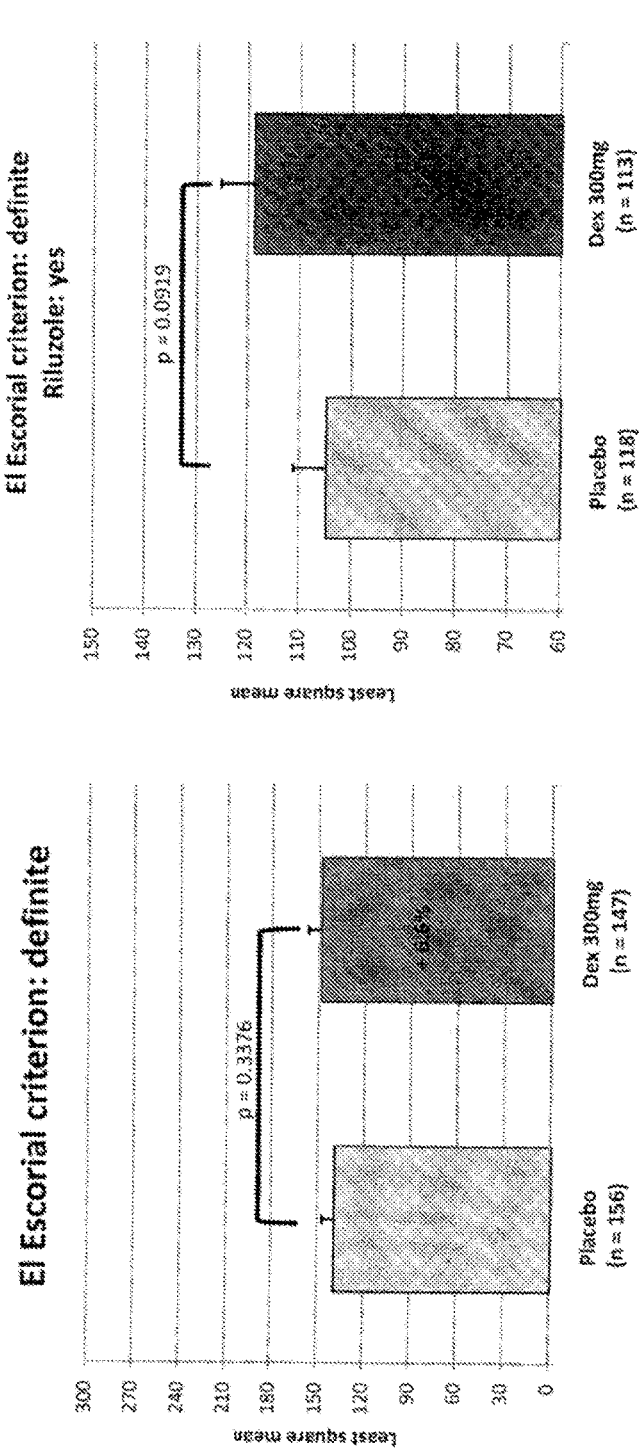
Figure 19:
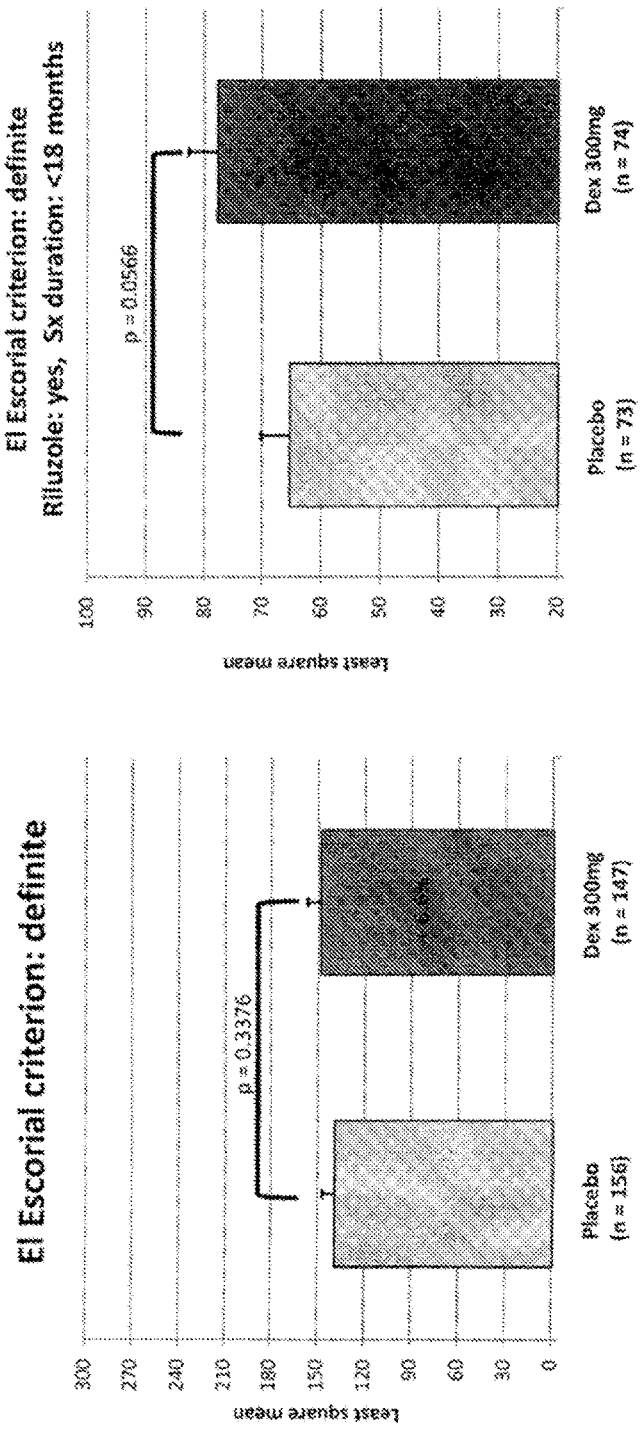
Figure 20:
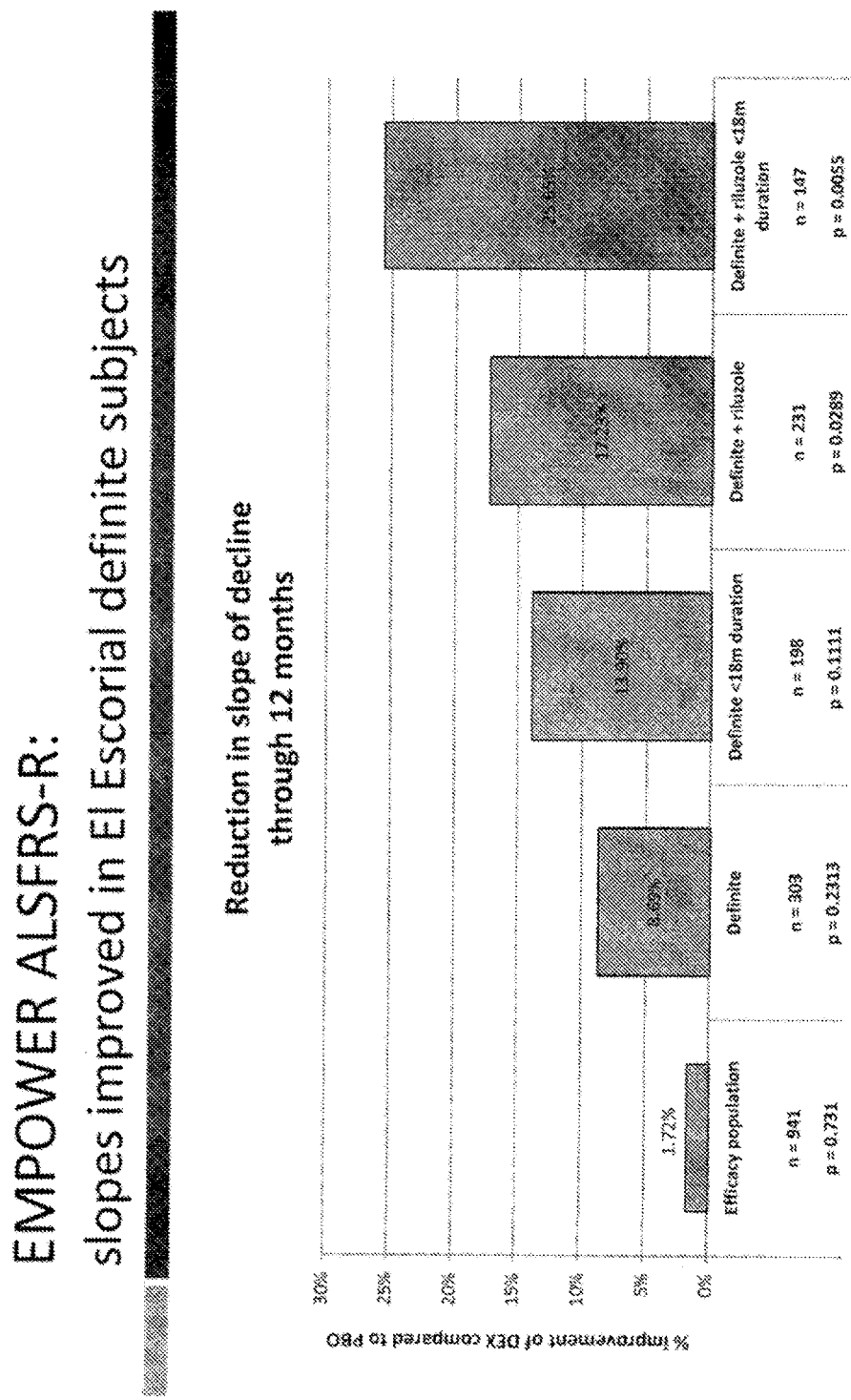
Figure 21:
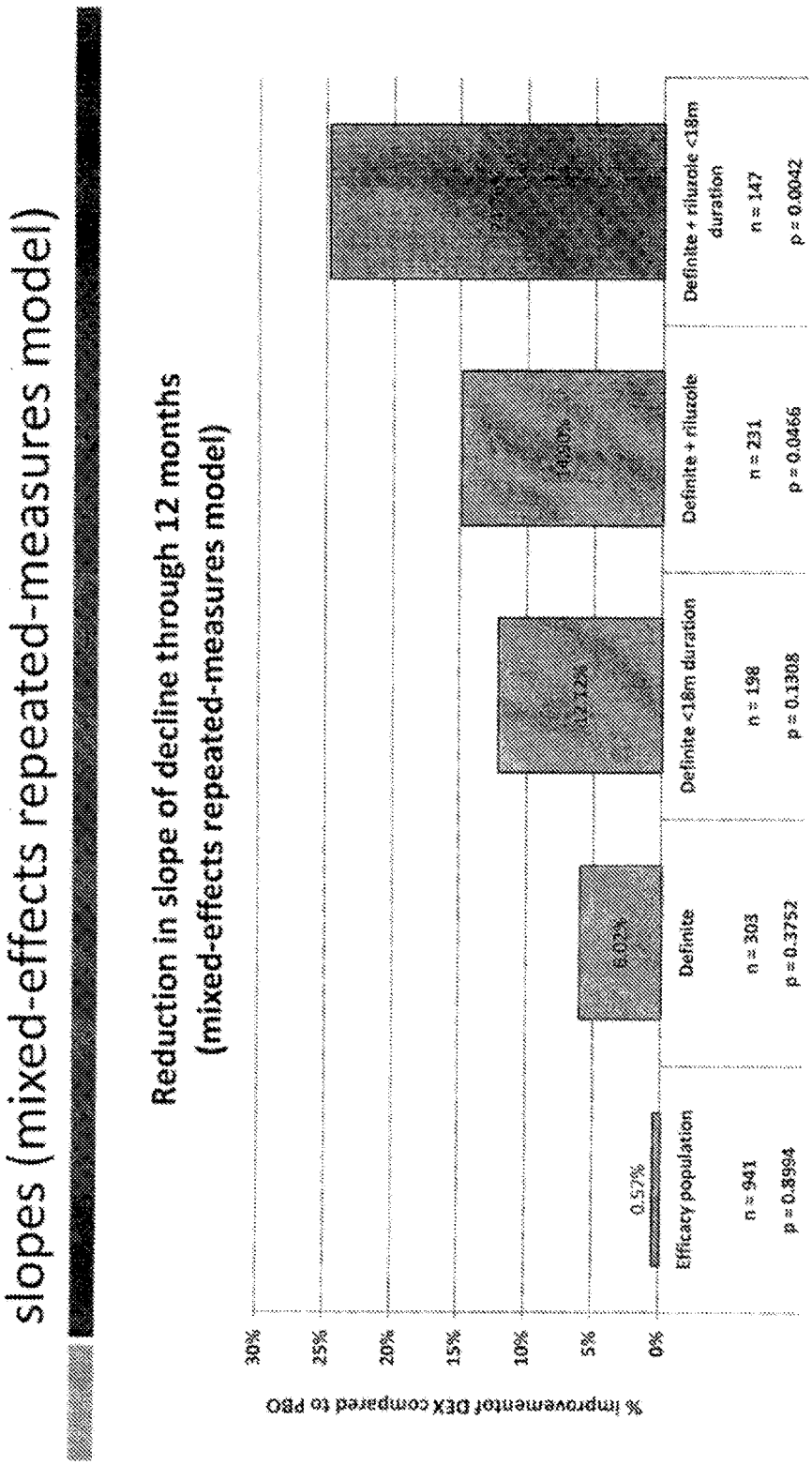
Figure 22:
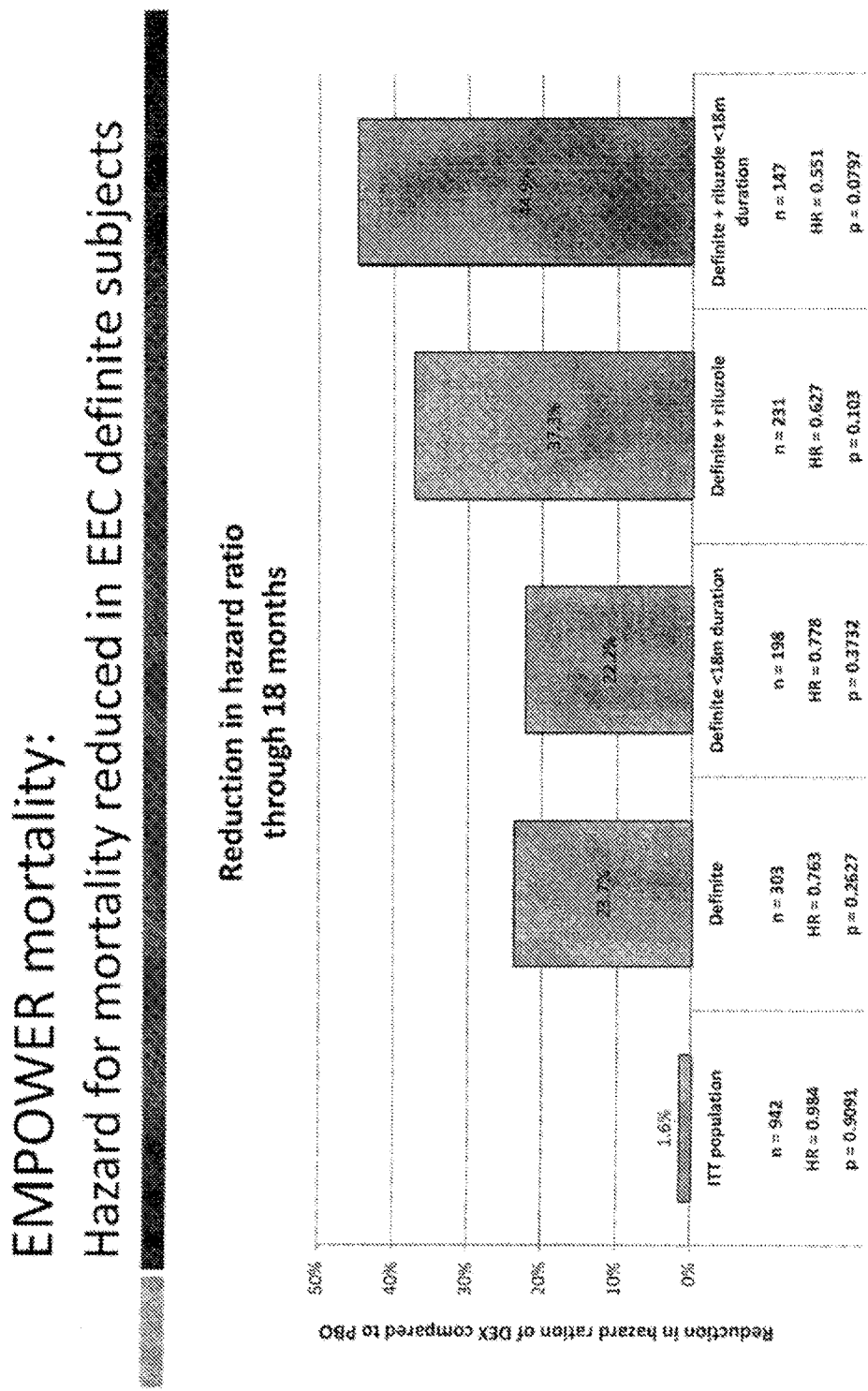
Figure 24:
Figure 26:
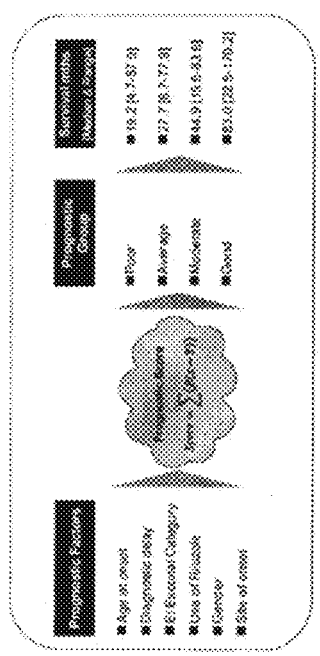
Figure 27:
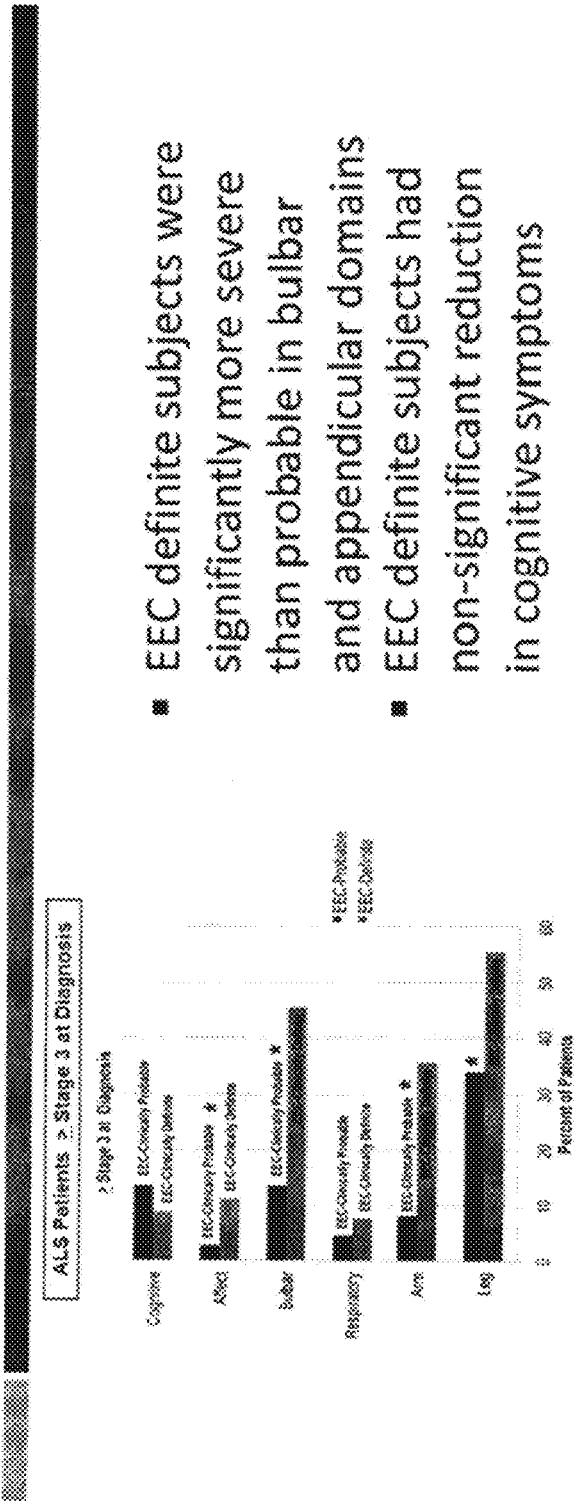
Figure 30:
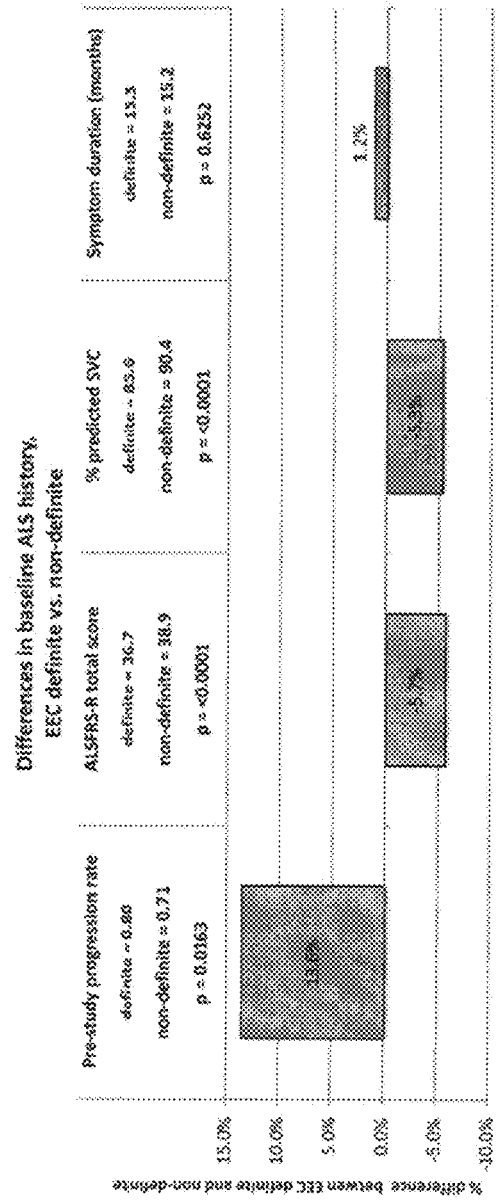
Figure 32:
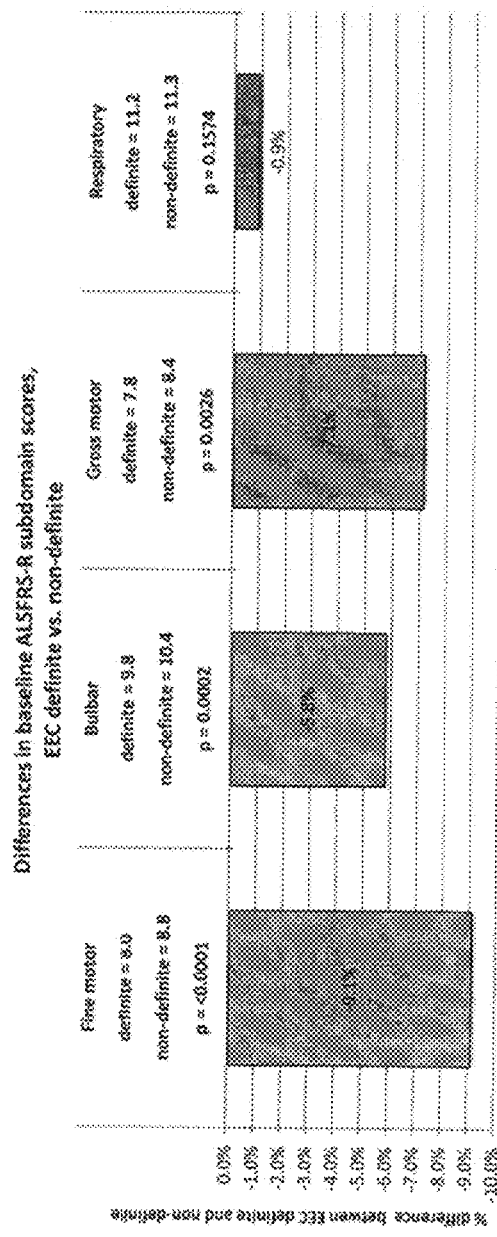
Figure 33:
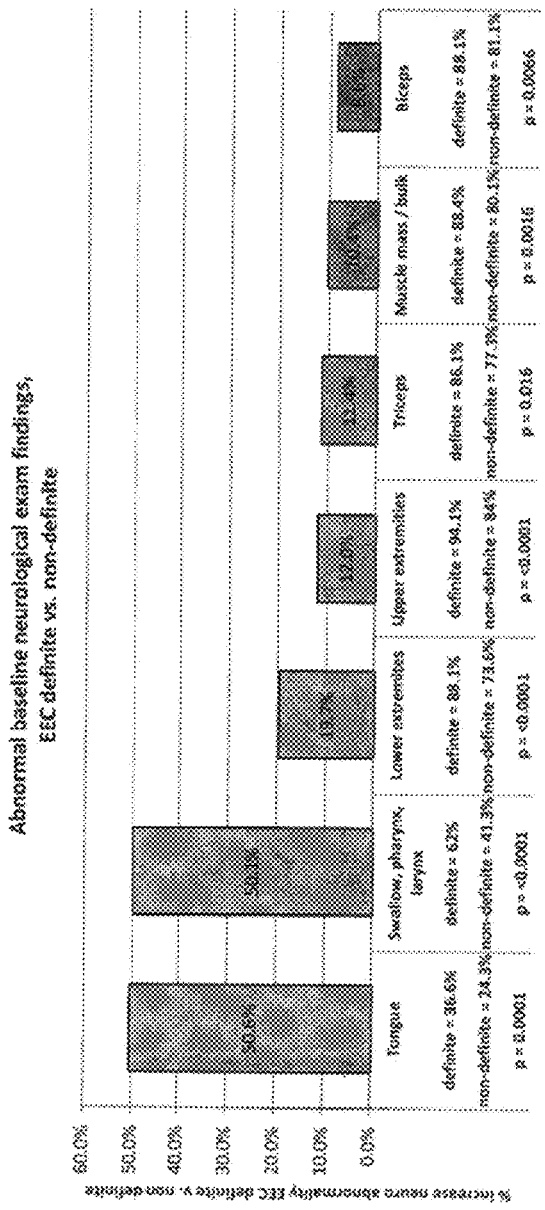
Figure 34:
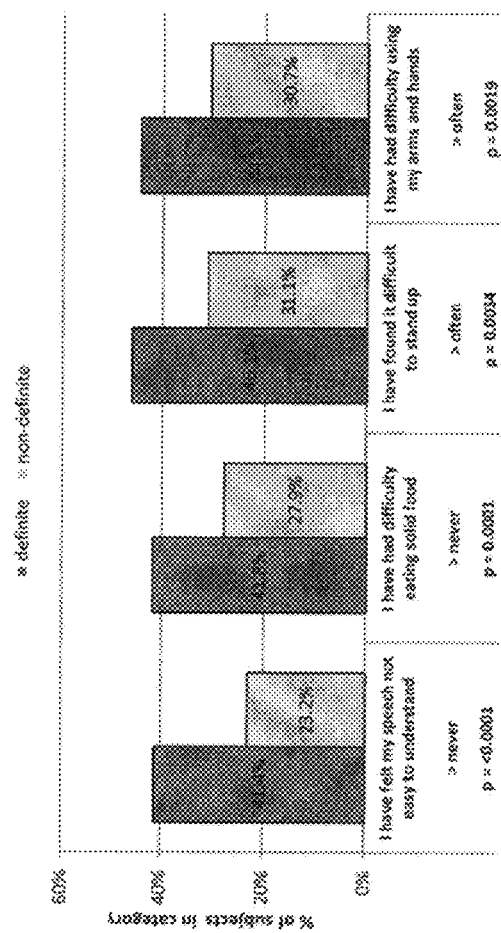
Figure 37:
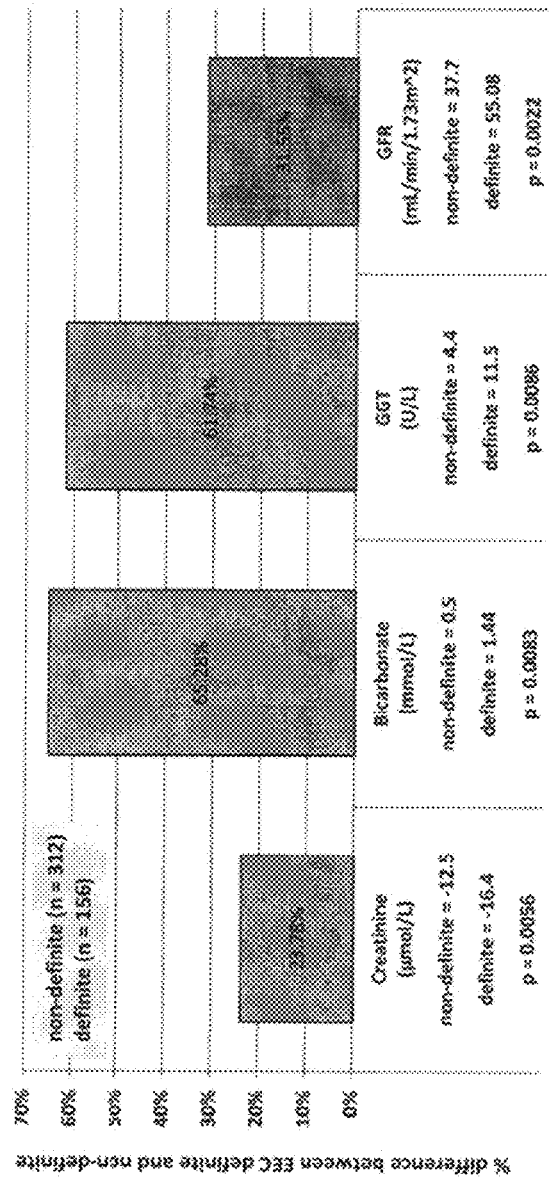
Figure 38:
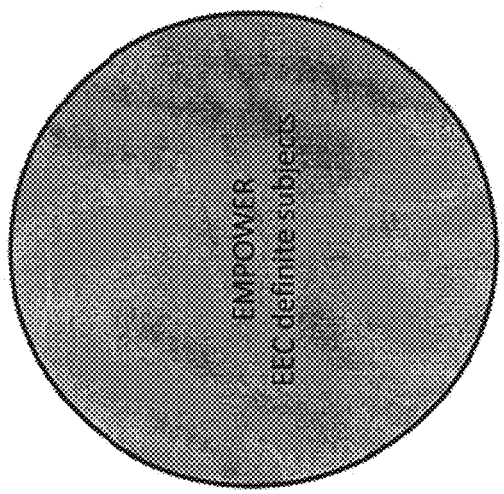
Figure 39:
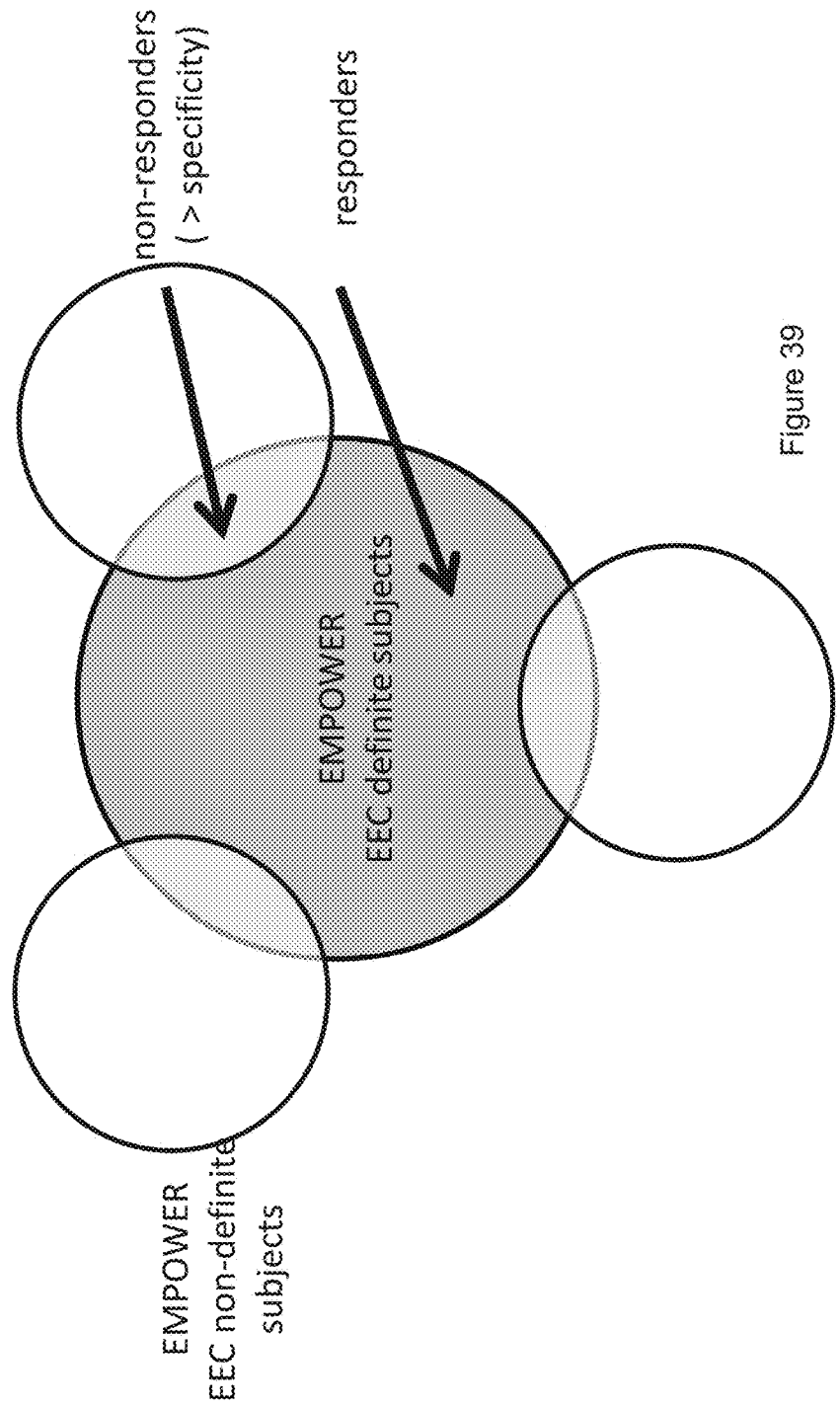
Figure 40:
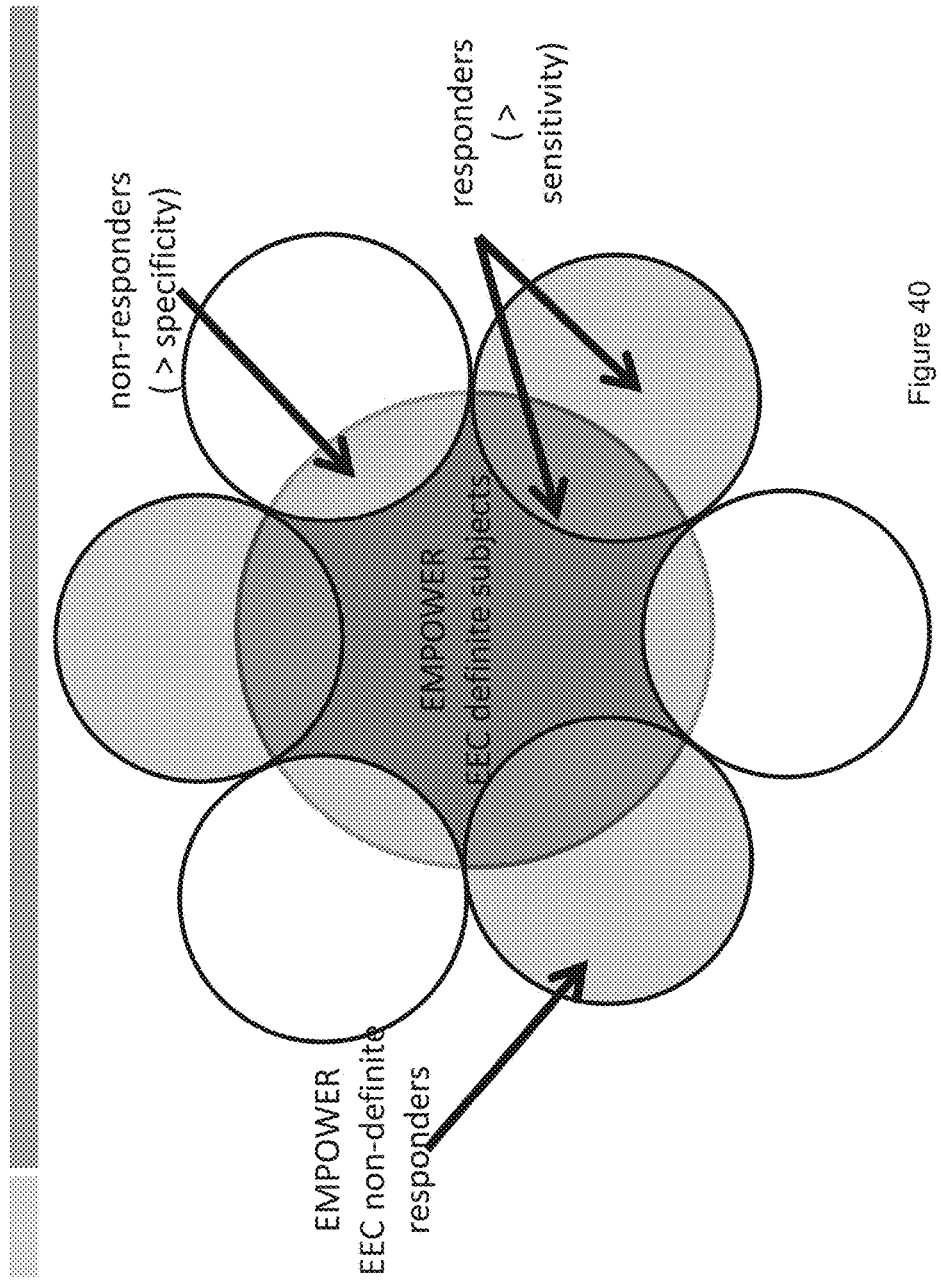
Figure 42:
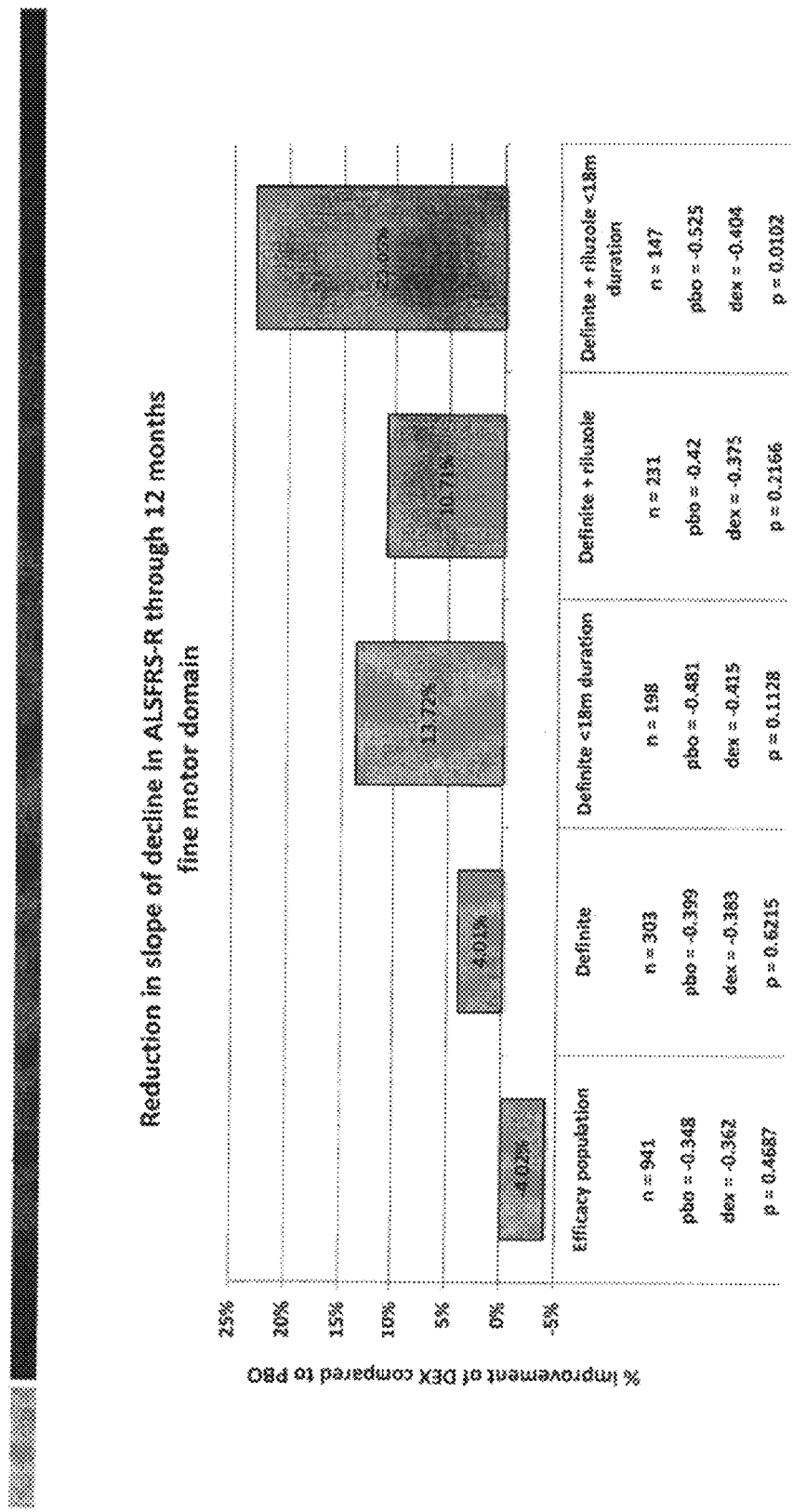
Figure 43:
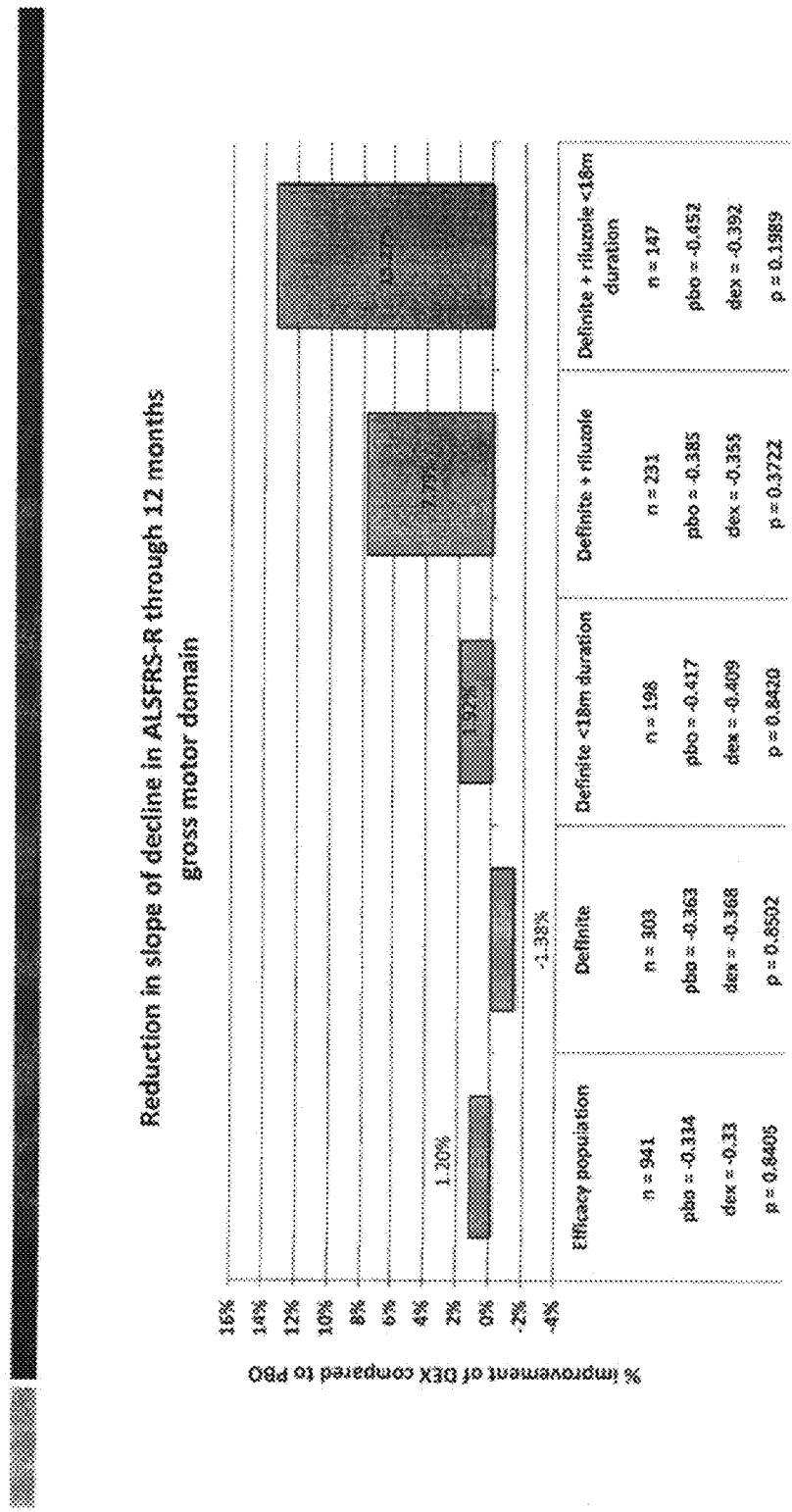
Figure 44:
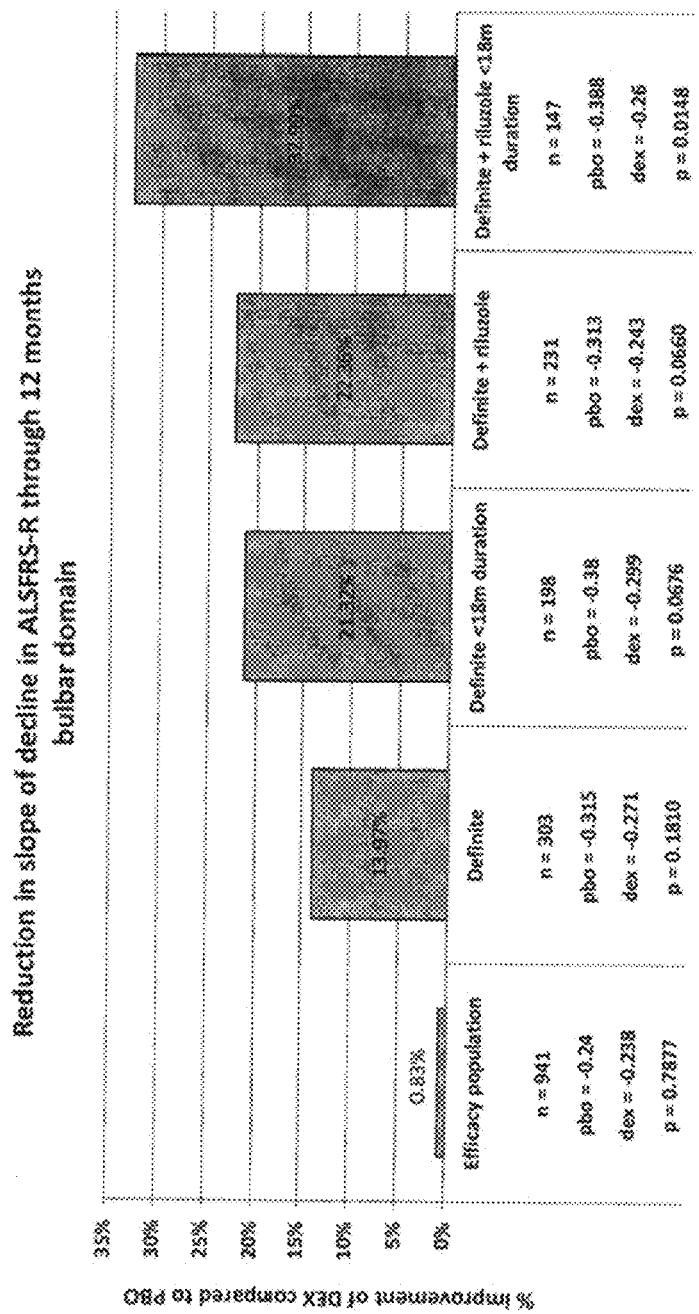
Figure 45:
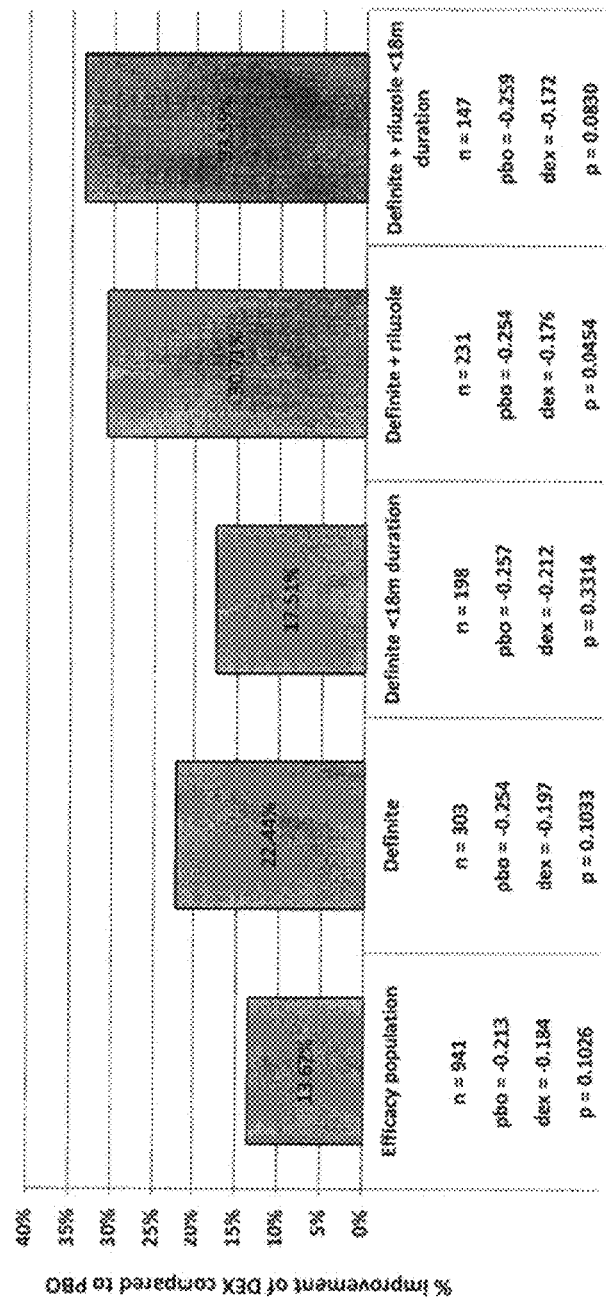
Figure 46:
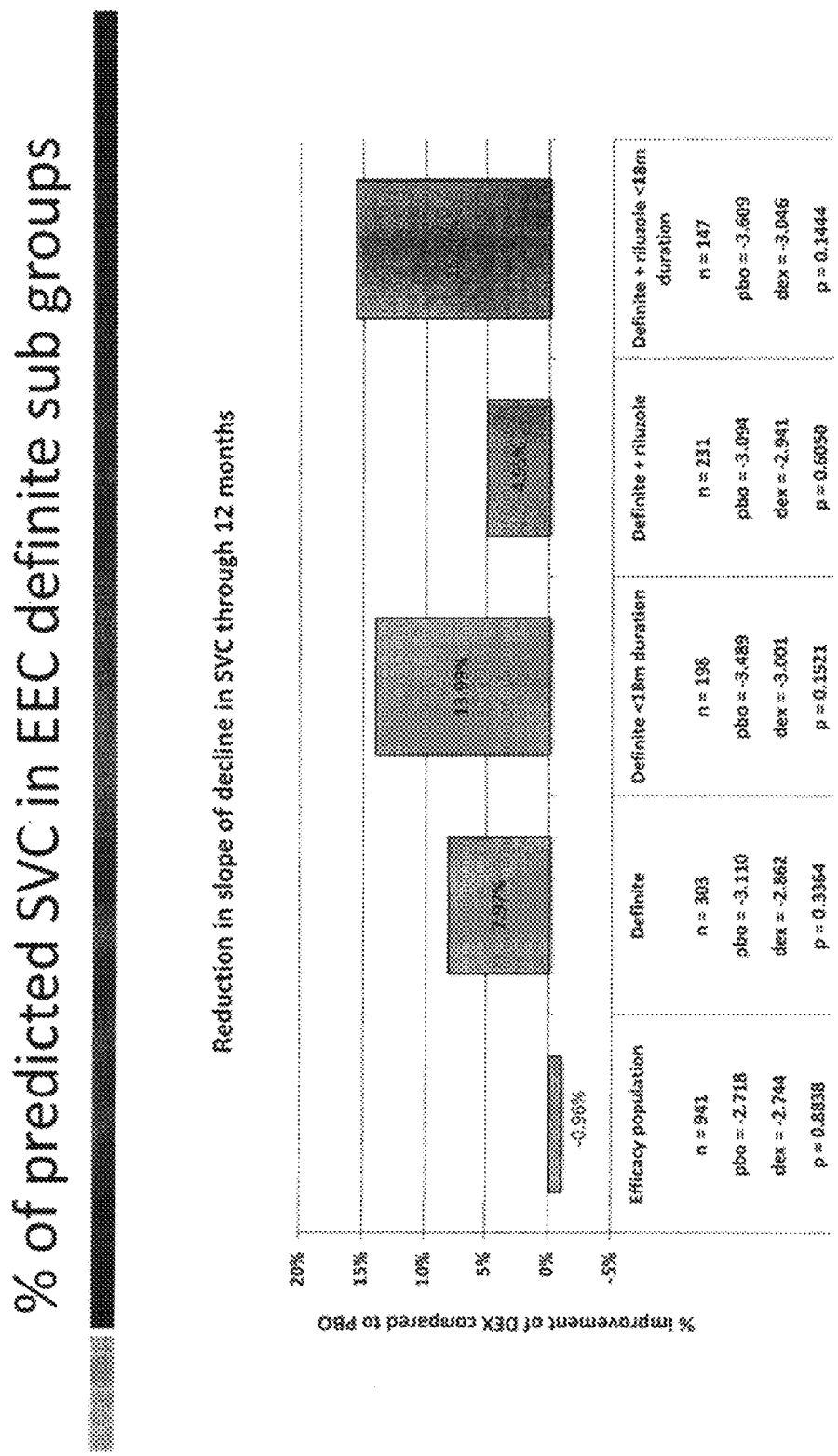
Figure 47:
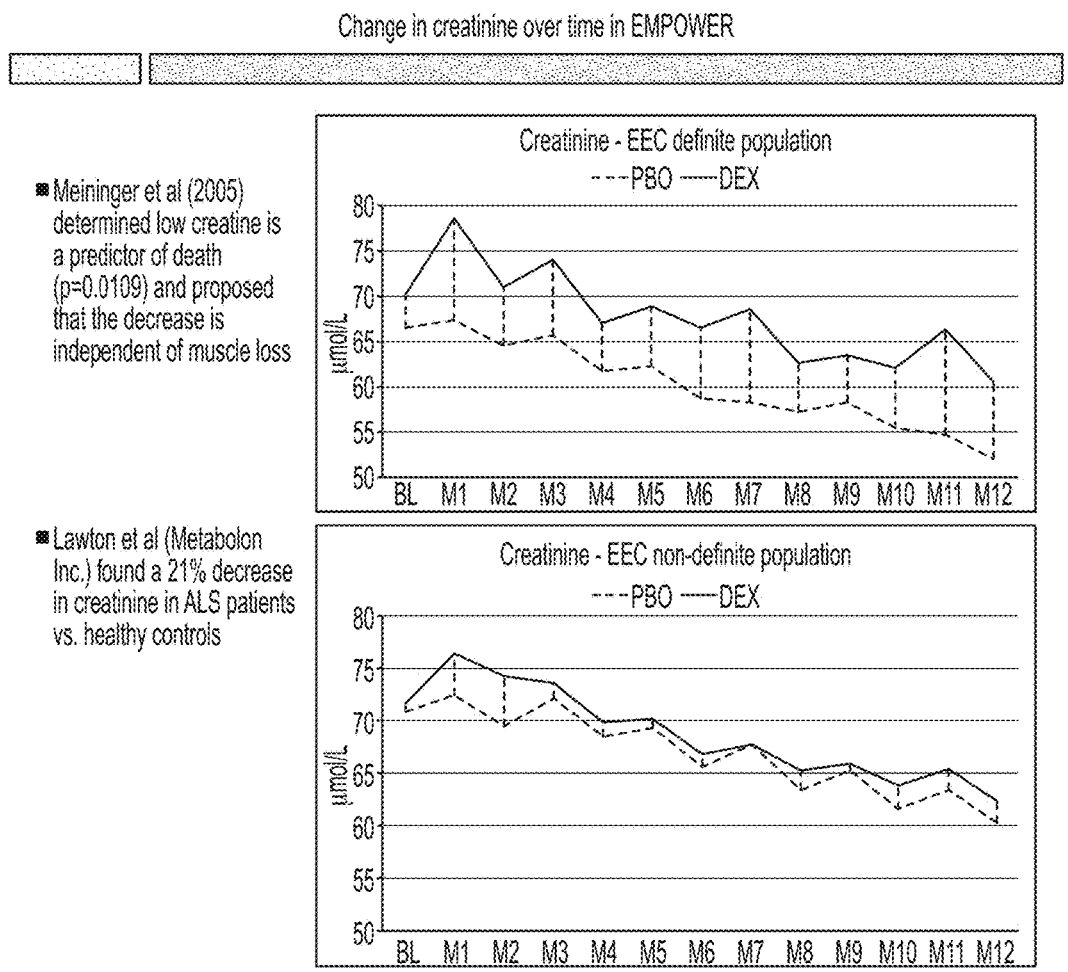
Figure 48:
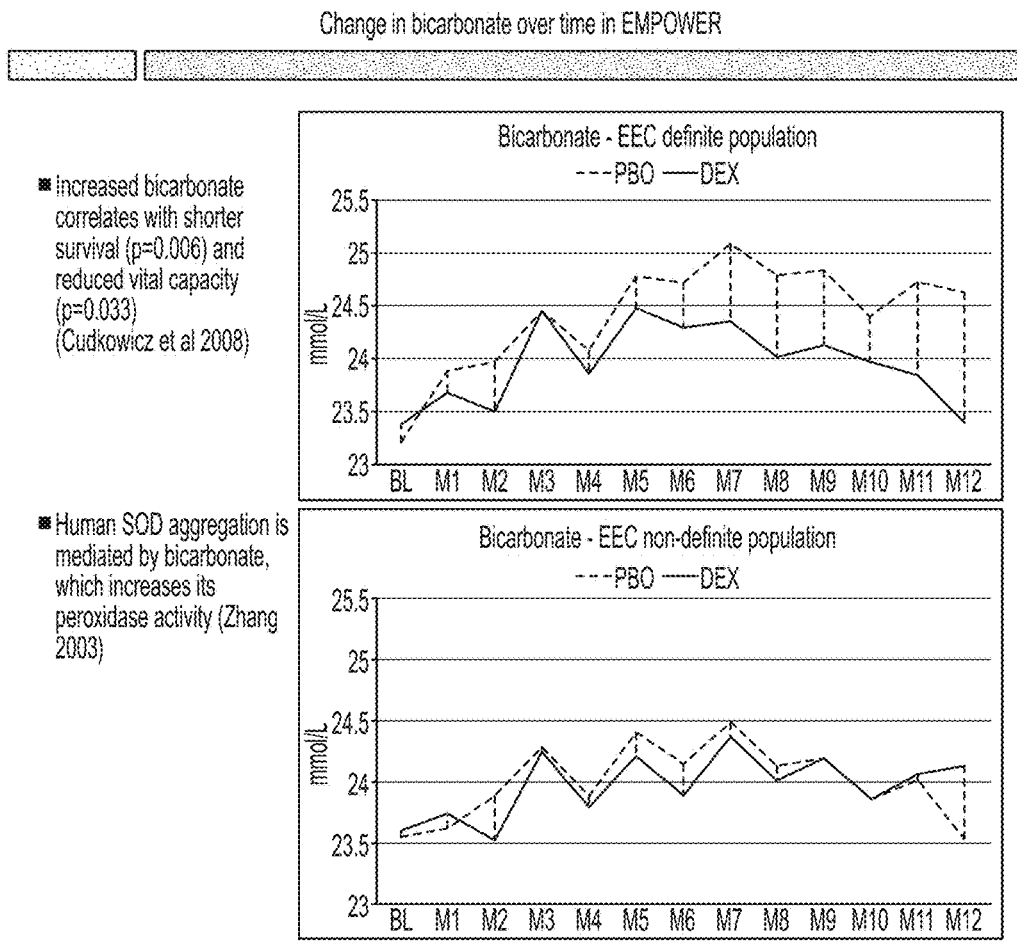
Figure 49:
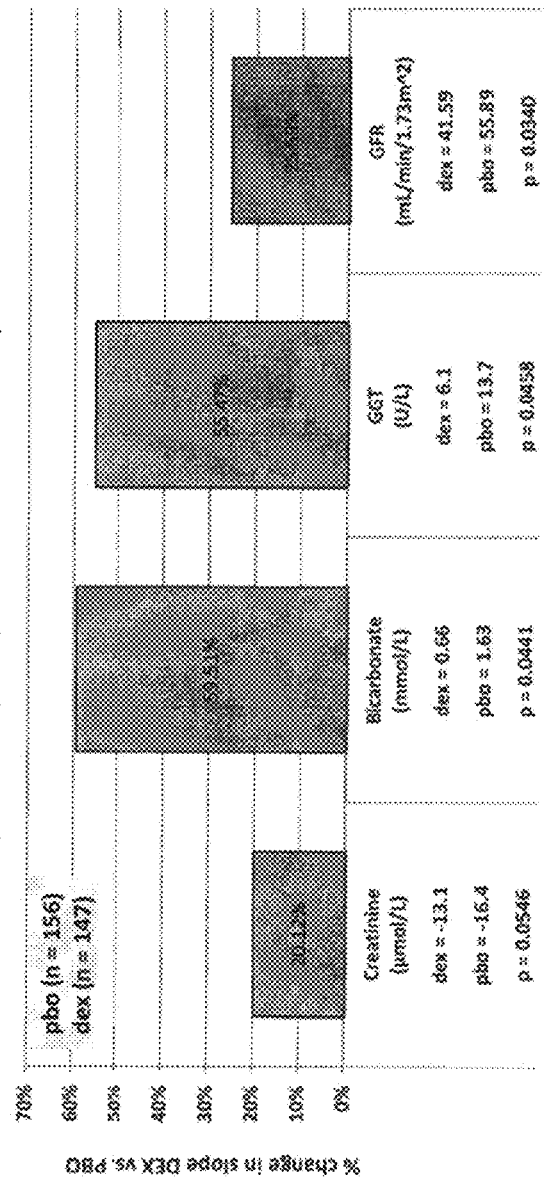
Figure 52:
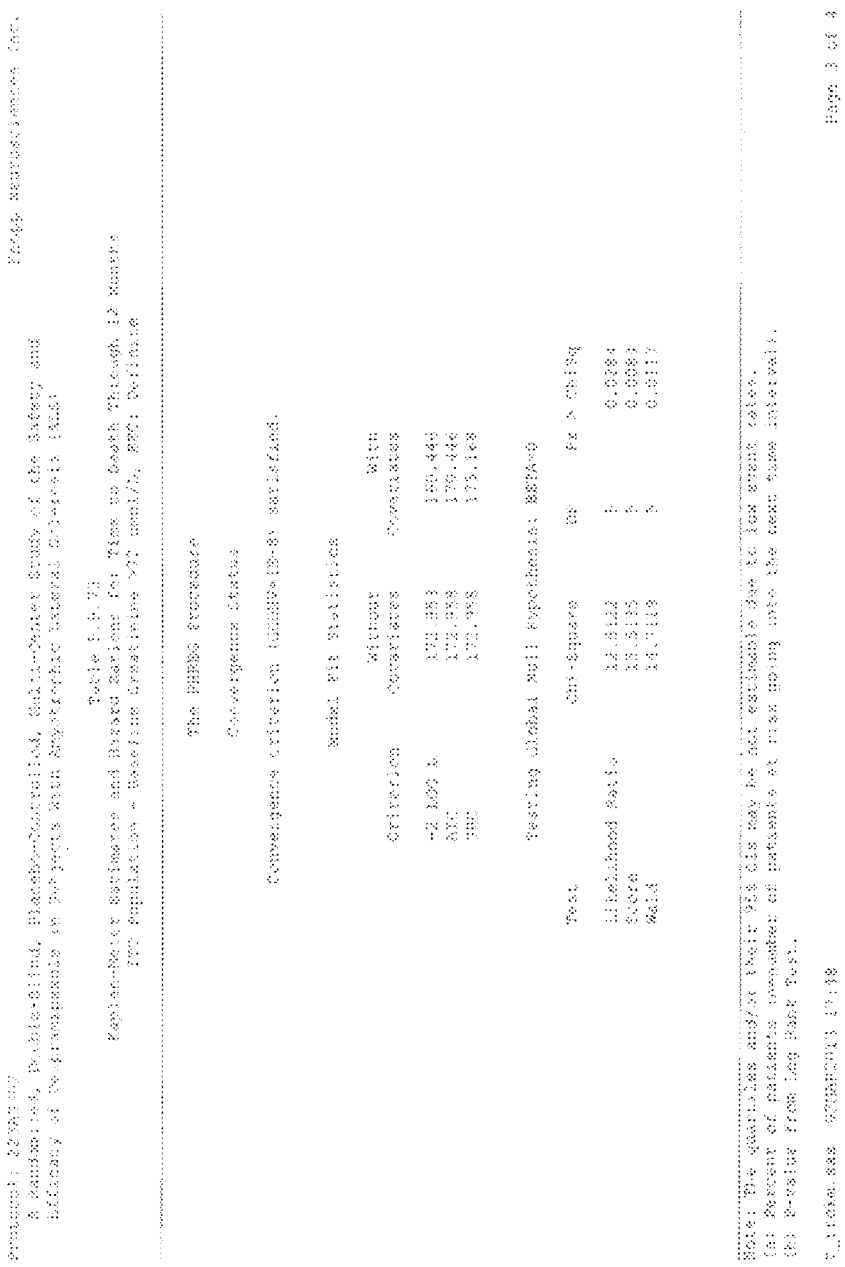

The initial analysis of the results of EMPOWER are set forth in FIG. 6 and FIG. 7. A comparison of the covariate distribution between the phase 2 CL201 and phase 3 EMPOWER studies are set forth in FIGS. 8 and 9. The effect of the EMPOWER enrollment patterns on El Escorial definite subjects is set forth in FIG. 10 and the impact on CAFS rank outcome is set forth in FIG. 11. A post-hoc analysis of the covariate impact on the results of CL201 is set forth in FIG. 12 and in particular the impact of the CAFS score in ALS definite subjects in FIG. 13. FIG. 14 shows the difference in CAFS value, ALSFRS-R scores and mortality in the ALS definite and non-ALS definite subjects in EMPOWER. FIG. 15 summarizes the significant differences in the patient populations and effects on treatment of ALS between the CL201 and the EMPOWER studies not previously identified. FIGS. 16-23 depict the results of dexpramipexole treatment in certain subpopulations of patients studied in EMPOWER. In particular, FIG. 16 depicts the improvement of CAFS rank in ALS definite subjects (as defined by El Escorial criteria). FIG. 17 depicts the improvement in CAFS rank in ALS definite subjects (as defined by El Escorial criteria) with symptom duration of less than 18 months. FIG. 18 depicts the improvement in CAFS rank in ALS definite subjects (as defined by El Escorial criteria) with concomitant riluzole administration. FIG. 19 depicts the improvement in CAFS rank in ALS definite subjects (as defined by El Escorial criteria) with symptom duration of less than 18 months and concomitant riluzole administration. FIG. 20 depicts the percent improvement of dexpramipexole compared to placebo in the reduction in slope of decline in the ALSFRS-R score in ALS definite patients, ALS definite patients with symptom duration of less than 18 months, ALS definite patients with concomitant riluzole administration and ALS definite patients with symptom duration of less than 18 months, as well as concomitant riluzole administration. FIG. 21 depicts the percent improvement of dexpramipexole compared to placebo in the reduction in slope of decline in the ALSFRS-R score (using the mixed-effects repeated-measures model) in ALS definite patients, ALS definite patients with symptom duration of less than 18 months, ALS definite patients with concomitant riluzole administration and ALS definite patients with symptom duration of less than 18 months, as well as concomitant riluzole administration. Further, FIG. 22 depicts the reduction in hazard ratio of dexpramipexole compared to placebo in ALS definite patients, ALS definite patients with symptom duration of less than 18 months, ALS definite patients with concomitant riluzole administration and ALS definite patients with symptom duration of less than 18 months, as well as concomitant riluzole administration.

A Monte Carlo analysis was done to identify characteristics of subjects in the phase 3 EMPOWER studies that were predictive of improved outcomes. Among the baseline characteristics most predictive of outcomes was a serum creatinine level greater than about 72 μmol/L. The analysis identified 369 patients meeting this criterion, of which 174 had been randomized to the placebo group and 195 to the treatment group.

Figure 54:
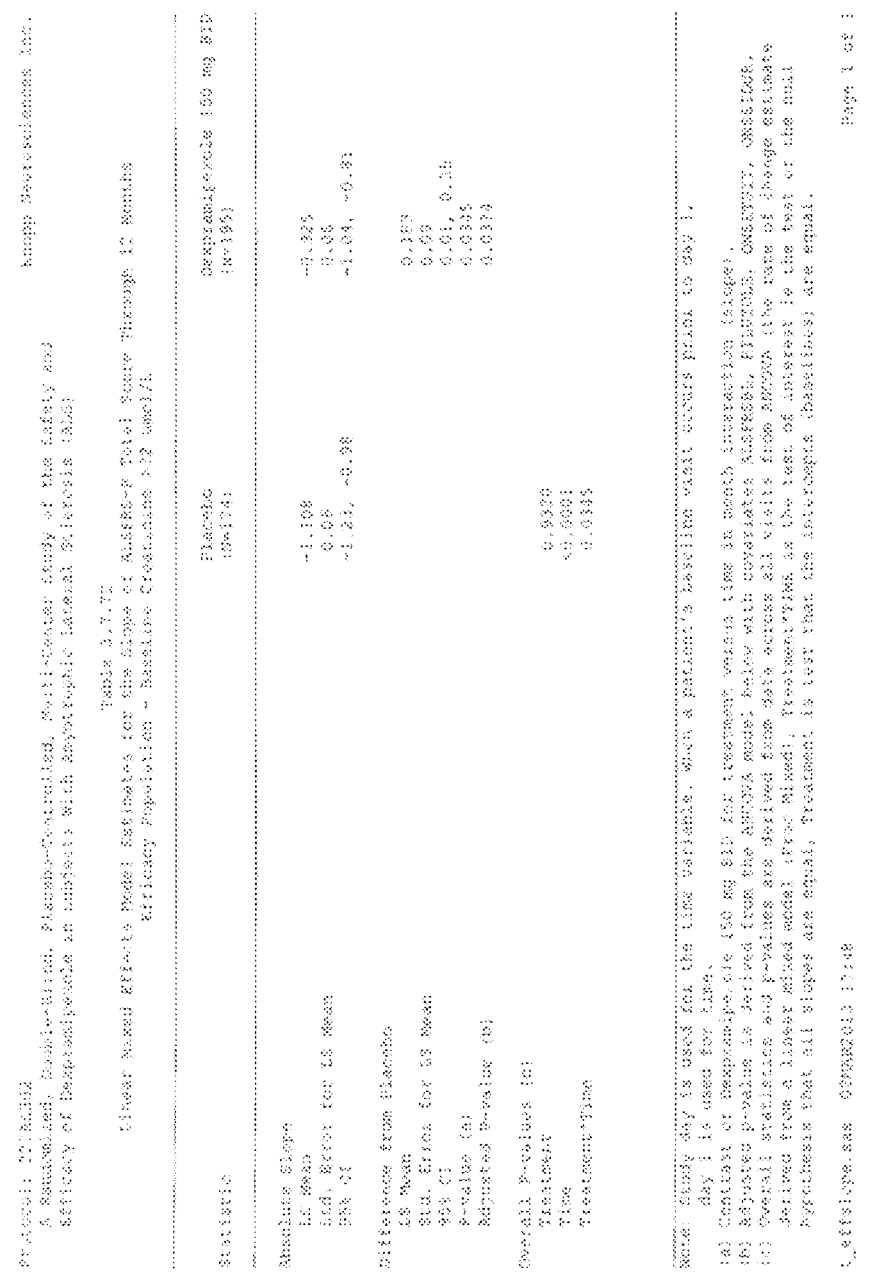
Figure 55:
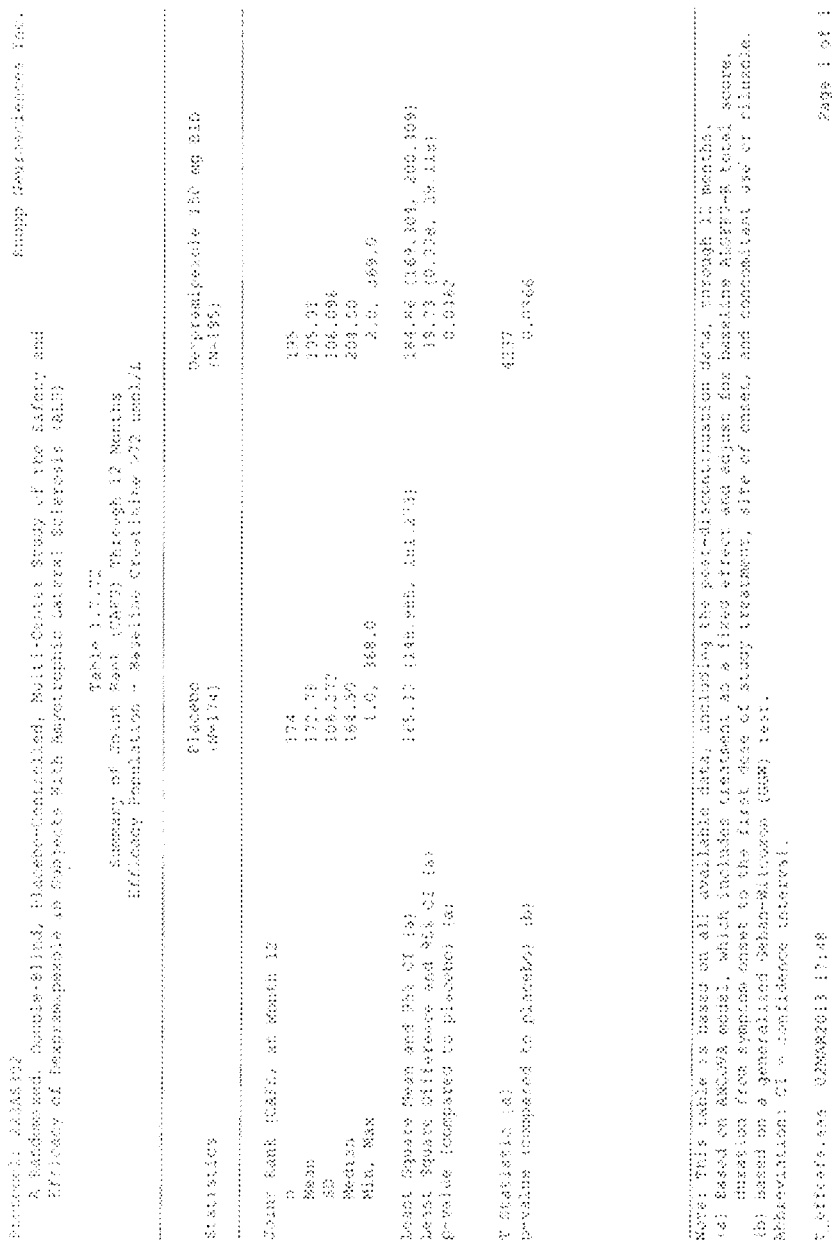

A subsequent statistical analysis (Macrostat Inc., Wilmington, Del.) was directed to treatment effects of dexpramipexole in the above-identified high-creatinine patient group. In a combined assessment of function and survival (CAFS), the high-creatinine group demonstrated a statistically significant 19% improvement in least square means between treatment and placebo (184.86 vs. 165.13, respectively; p=0.0366). See FIG. 55. In a separate analysis of the slope of decline on the ALS Functional Rating Scale (Revised), the high-creatinine group demonstrated a statistically significant 18% improvement in least square means between treatment and placebo (−0.925 vs. −1.108; p=0.0345). See FIG. 54. In a Kaplan-Meier analysis of mortality, the high-creatinine group demonstrated a trend toward improved survival, as demonstrated by a 10.3% rate of mortality in the treatment group at 12 months vs. a 16.1% rate of mortality in the placebo group at 12 months (p=0.1207). See FIGS. 50-53.

The effects of dexpramipexole in simultaneously preserving serum creatinine levels and establishing improved outcomes for ALS subjects was further confirmed in an analysis of laboratory values and outcomes in a separate clinical study. This study has been reported to have shown dose-dependent benefits of twice-daily administration of dexpramipexole across both of the two parts of the study, in which 102 subjects were randomized in Part One to placebo or total daily doses of 50 mg, 150 mg, or 300 mg of dexpramipexole, after which, following a one-month placebo washout for all patients, subjects were randomized in Part Two to total daily doses of either 50 mg or 300 mg of dexpramipexole.

In Part One of the study, subjects receiving the highest daily dose of dexpramipexole experienced both the least disease progression compared to the other groups (data reported elsewhere), and also the least decline in levels of serum creatinine (a decline of 0.0 in the 300 mg group, compared to declines of 0.07, 0.05, and 0.06 in the placebo, 50 mg, and 150 mg groups, respectively). In Part Two of the study, subjects receiving daily doses of 300 mg of dexpramipexole experienced a mean decline in serum creatinine at Week 28 of zero, vs. a mean decline in the subjects receiving daily doses 50 mg of −0.12. Subjects receiving the 300 mg daily dose also experienced a significantly reduced reduction in the combined assessment of function and survival (CAFS; p=0.040).

Treatment with dexpramipexole in both the Phase 2 and Phase 3 studies was associated with a reduction in the decline of serum creatinine levels as well as a reduction in the progression of disease.

Without wishing to be bound by theory, the use of serum creatinine as a biomarker to predict the treatment effects of dexpramipexole in patients with ALS may be related to either or both of at least two mechanisms. First, the biomarker may be based on creatinine as a marker of muscle loss, since levels of serum creatinine are known to be associated with the loss of muscle mass in human subjects. Second, the biomarker may also be a marker of the mechanistic effects of dexpramipexole at its molecular sites of action, including the mitochondria of either nerve cells or muscle cells or both.

An analysis of the results of the EMPOWER study includes the Kaplan-Meier estimates and hazard rations for time to death through twelve months for subjects with a baseline creatinine of greater than about 72 µmol/L is set forth in tables in FIGS. 50-53. Linear mixed effects model estimates for the slope of ALSFRS-R total score through twelve months for subjects with a baseline creatinine of greater than about 72 µmol/L is set forth in a table in FIG. 54. A summary of joint rank (CAFS) through twelve months for subjects with a baseline creatinine of greater than about 72 µmol/L is set forth in a table in FIG. 55. The change from baseline in serum creatinine results by treatment group is shown in tables in FIGS. 56-67.

EXAMPLE 2 UNBIASED IDENTIFICATION OF RESPONDER SUBGROUPS

This analysis seeks to identify subgroups of patients that exhibit strong "response" to treatment based upon the reported results of the EMPOWER clinical trial, as evidenced by comparing statistics of treated and untreated members of these subgroups. Response is defined according to two criteria:

1. reduction of disease symptom progression in treated patients as compared to placebo patients in the same subgroup;

2. reduction of end-of-study mortality in treated patients as compared to placebo patients in the same subgroup.

This analysis examined subgroup definitions based on both single and dual attribute criteria, and evaluated the performance of each subgroup with respect the two criteria above. To facilitate ranking of subgroups, we have defined a scoring metric which aggregates these two-dimensional scores into a single scalar called "score" in our report files. Larger scores are better: scores increase when mortality rates decrease, and when ALSFRS-R changes from baseline become more positive (i.e. score decreases are reduced). This scoring scheme is somewhat arbitrary; it merely serves to guide our maximization process and provide convenient rankings of subgroup quality. The definition of the score could certainly be altered to reflect different priorities on treatment effects with respect to mortality or disease progression. For this reason, we provide a complete spreadsheet of results, which can be re-sorted and re-ordered according to arbitrary balancing criteria.

Assumptions in Calculations:

1. Mortality for patients is defined by the value of the "end_status_study" field. Patients are deemed dead if and only if the value of this field is "DEATH"; any other value is interpreted as survival;

2. Disease symptom progression is measured in terms of the change in total ALSFRS-R score from baseline, as reported in the "change from baseline" attribute of each patient. Specifically, we take the value of "change from baseline" that is reported at the final measurement time for each patient.;

3. We analyze only subgroups which are defined in terms of pre-treatment baseline patient attributes; subgroups based on dynamic time course information have not been examined; and 4. We impose minimum subgroup size filters on our results to exclude promising signals which arise due to sampling artifacts, or which would be too narrow for consideration in future studies. Analyses were run for minimum group sizes of both 50 patients (data not shown) and 100 patients (i.e. for a cutoff of N, we require at least N patients in that subgroup for both the treated and untreated groups).

Results

We find that there are a multitude of subgroups which show very large treatment effects with respect to both response criteria under our assumptions, with a large number of these subgroups showing much higher efficacy than the standard set by the "definite diagnosis" subgroup. Note that smaller subgroups may exhibit stronger signals at the cost of narrower inclusion criteria, engendering a tradeoff between response magnitude and group size. For this reason, subgroup size filters were imposed as described above, and the result spreadsheets report subgroup sizes to allow additional post hoc filtering.

Note that results for both single and dual criteria analyses are included in these spreadsheets for completeness, but we suggest focusing primarily on the single criteria analyses. Dual criteria allow "ands" and "ors" of subgroups, which complicate interpretation and increase the possibility of spurious findings.

For reference, the definite diagnosis subgroup (highlighted in yellow in the single criteria spreadsheets), treatment is associated with a relative change of −8.3% in the mean ALSFRS-R change from baseline, and a −30.9% change in mortality rate. In contrast, the best-scoring single dimensional subgroup with a minimum group size of 50 (the subgroup "min_pr_interval>195") shows a relative change of −26.6% in the mean ALSFRS-R change from baseline, and a −67.9% change in mortality rate. When a minimum group size of 100 is imposed, the best-scoring subgroup (the subgroup "mean_pr_interval>184.5") shows a relative change of −20.5% in the mean ALSFRS-R change from baseline, and a −47.3% change in mortality rate.

Interpretation of Results

Each row of the attached spreadsheet represents a candidate patient subgrouping, and shows the statistics associated with that subgroup. Subgroups are displayed in descending order by effectiveness: better subgroups are listed first. The following page illustrates how to understand the findings in the spreadsheet.

Sample Subgroup Finding

| score | pct_alsfrs_change | pct_mort_rate_change | abs_alsfrs_change | abs_mort_rate_change | trtd_mort_rate | trtd_mean_alsfrs_change |
|---|---|---|---|---|---|---|
| 0.343 | −26.6% | −67.9% | 5.623 | −22.6% | 10.7% | −15.482 |
| score | trtd_count | untrtd_mort_rate | untrtd_mean_alsfrs_change | untrtd_count | label | |
| 0.343 | 56 | 33.3% | −21.105 | 57 | NOT (min_pr interval (msec) <= 195.000) | |

Translation:

The subgroup "min_pr_interval>195" contains 56 treated patients and 56 untreated patients. Treated patients in this group exhibit an overall mortality rate of 10.7% and a mean ALSFRS-R score change of −15.48, while untreated patients in this group exhibit an overall mortality rate of 33.3% and a mean ALSFRS-R score change of −21.1%. This constitutes a relative change of −26.6% change in the ALSFRS-R score change and a relative change of −67.9% in mortality rate which are associated with treatment. In absolute terms, this corresponds to ASLFRS-R scores whose average is 5.623 points higher for treated patients (i.e. negative slope has been reduced), and a mortality rate which is 22.6 percentage points lower for treated patients. The defined combined score for this subgroup is 0.343.

Field Descriptions

The Columns of this File are Briefly Described Below:

pct_alsfrs_change: relative change in mean ALSFRS-R total score between treated and untreated patients in the current subgroup. This corresponds to "percent reduction" in ALSFRS-R scores; the more negative this value is, the better the subgroup is.

pct_mort_rate_change: relative change in mortality rate between treated and untreated patients in the current subgroup; the more negative this value is, the better the subgroup is.

abs_alsfrs_change: absolute difference in mean ALSFRS-R total scores between treated and untreated patients in the current subgroup. This corresponds to the rise in ALSFRS-R associated with treatment; the more positive this value is, the better the subgroup is.

abs_mort_rate_change: absolute difference in mortality rate between treated and untreated patients in the current subgroup. This corresponds to the decrease in mortality associated with treatment; the more negative this value is, the better the subgroup is.

trtd_mort_rate: mortality rate of treated patients in this subgroup.

trtd_mean_alsfrs_change: mean change in ALSFRS-R score from day 1 score to final score over all treated patients in the subgroup; the more positive this value is, the better the subgroup is.

trtd_count: number of treated patients in this subgroup untrtd_mort_rate: mortality rate of untreated patients in this subgroup untrtd_mean_alsfrs_change: mean change in ALSFRS-R score from day 1 score to final score over all untreated patients in the subgroup; the more positive this value is, the better the subgroup is.

untrtd_count: number of untreated patients in this subgroup label: the definition of the subgroup. When the subgroup is described as "NOT(x)", this indicates the negation of the subgroup clause. For example, "NOT(walking<=3)" means "walking>3"

What is claimed is:

1. A method of treating amyotrophic lateral sclerosis in a subject in need thereof comprising administering to the subject a therapeutically effective amount of (6R)-2-amino-4,5,6,7-tetrahydro-6-(propylamino)benzothiazole or a pharmaceutically acceptable salt thereof,
   wherein the subject's creatinine value is greater than or equal to 72.0 µmol/L.

2. The method of claim 1, wherein the subject experiences a reduction in muscle loss.

3. The method of claim 1, wherein the subject is treated and experiences a reduction in the slope of decline of fine motor skills.

4. The method of claim 1, wherein the subject is treated and experiences a reduction in the slope of decline of gross motor skills.

5. The method of claim 1, wherein the subject is a subject with concomitant riluzole administration.

6. The method of claim 1, wherein the subject has an amyotrophic lateral sclerosis symptom onset duration of less than about 18 months.

7. The method of claim 1, wherein the amyotrophic lateral sclerosis is defined by the El Escorial diagnosis criteria.

8. The method of claim 7, wherein the subject further has diagnostic criteria selected from the group consisting of a pulse rate of greater than 81.0 beats per minute, a cholesterol value of less than or equal to 5.3 mmol/L, a creatine phosphokinase value of less than or equal to 184.0 U/L, a bicarbonate value of less than or equal to 21.6 mmol/L, or any combination thereof.

9. The method of claim 7, wherein the subject further has diagnostic criteria selected from the group consisting of an ALSFRS-R score of greater than 36.0, a pre-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a diastolic blood pressure of greater than 82.0 mmHg, a systolic blood pressure of less than or equal to 117.0 mmHg, a phosphorous value of less than or equal to 1.090 µmol, a platelet count of less than or equal to $248.0 \times 10^9$ cells/L, a lactate dehydrogenase value of less than or equal to 161.0 U/L, a triglyceride level of less than or equal to 1.4 mmol/L, a uric acid level of greater than 320.0 µmol/L, a gamma-glutamyltransferase (GGT) level of greater than 37.0 U/L, a total bilirubin level of less than or equal to 6.0 μmol/L, a urine pH of less than or equal to 5.5, and any combination thereof.

10. The method of claim 1, wherein the subject is diagnosed with one of the following diseases: definite amyotrophic lateral sclerosis, probable amyotrophic lateral sclerosis, probable-laboratory supported amyotrophic lateral sclerosis, possible amyotrophic lateral sclerosis, and suspected amyotrophic lateral sclerosis.

11. The method of claim 1, wherein the therapeutically effective amount of (6R)-2-amino-4,5,6,7-tetrahydro-6-(propylamino)benzothiazole or a pharmaceutically acceptable salt thereof is from 150 milligrams to 3,000 milligrams per day.

12. The method of claim 1, wherein the therapeutically effective amount of (6R)-2-amino-4,5,6,7-tetrahydro-6-(propylamino)benzothiazole or a pharmaceutically acceptable salt thereof is from 150 milligrams to 900 milligrams per day.

13. The method of claim 1, wherein the therapeutically effective amount of (6R)-2-amino-4,5,6,7-tetrahydro-6-(propylamino)benzothiazole or a pharmaceutically acceptable salt thereof is from 150 milligrams to 600 milligrams per day.

14. The method of claim 1, wherein the therapeutically effective amount of (6R)-2-amino-4,5,6,7-tetrahydro-6-(propylamino)benzothiazole or a pharmaceutically acceptable salt thereof is from 150 milligrams to 300 milligrams per day.

15. The method of claim 1, wherein the therapeutically effective amount of (6R)-2-amino-4,5,6,7-tetrahydro-6-(propylamino)benzothiazole or a pharmaceutically acceptable salt thereof is 150 milligrams twice daily.

16. The method of claim 1, wherein the therapeutically effective amount of (6R)-2-amino-4,5,6,7-tetrahydro-6-(propylamino)benzothiazole or a pharmaceutically acceptable salt thereof is 300 milligrams twice daily.

17. The method of claim 1, wherein the chiral purity for (6R)-2-amino-4,5,6,7-tetrahydro-6-(propylamino)benzothiazole or a pharmaceutically acceptable salt thereof is about 99% or more.

18. The method of claim 1, wherein the therapeutically effective amount of (6R)-2-amino-4,5,6,7-tetrahydro-6-(propylamino)benzothiazole or a pharmaceutically acceptable salt thereof is administered in a pharmaceutical composition, wherein said pharmaceutical composition further comprises a pharmaceutically acceptable excipient.

19. The method of claim 18, wherein said pharmaceutical composition is chirally pure for (6R)-2-amino-4,5,6,7-tetrahydro-6-(propylamino)b benzothiazole or a pharmaceutically acceptable salt thereof.

20. The method of claim 18, wherein said pharmaceutical composition is selected from the group consisting of a tablet, a capsule, and a liquid.

21. The method of claim 1, wherein said (6R)-2-amino-4,5,6,7-tetrahydro-6-(propylamino)benzothiazole or a pharmaceutically acceptable salt thereof is administered orally.

* * * * *